United States Patent [19]

Blum et al.

[11] Patent Number: 5,550,021

[45] Date of Patent: Aug. 27, 1996

[54] ALLELIC DIAGNOSIS OF SUSCEPTIBILITY TO COMPULSIVE DISORDER

[75] Inventors: Kenneth Blum, San Antonio, Tex.; Ernest P. Noble, Los Angeles, Calif.; Peter J. Sheridan, San Antonio, Tex.

[73] Assignees: Board of Regents, The University of Texas System, Austin, Tex.; Regents of the University of California, Oakland, Calif.

[21] Appl. No.: 299,934

[22] Filed: Sep. 1, 1994

Related U.S. Application Data

[63] Continuation-in-part of Ser. No. 909,383, Jun. 24, 1992, which is a continuation-in-part of Ser. No. 826,222, Jan. 23, 1992, Pat. No. 5,210,016, which is a continuation of Ser. No. 477,057, Feb. 7, 1990, abandoned.

[51] Int. Cl.$^6$ .............................. C12Q 1/68; C12P 19/34; C07H 21/04; C12N 15/00

[52] U.S. Cl. ........................... 435/6; 435/91.1; 435/91.2; 435/810; 536/23.1; 536/23.5; 536/24.31; 536/24.33; 935/76; 935/77; 935/78

[58] Field of Search ............................ 435/6, 91.1, 91.2, 435/810; 536/23.1, 23.5, 24.31, 24.33; 935/76–78

[56] References Cited

U.S. PATENT DOCUMENTS 5,210,016  5/1993  Blum et al. .................. 435/6

OTHER PUBLICATIONS

Sequence Comparison; Registry File; RN 151632-04-1

Suarez et al., *Genomics* 19: 12–20 (1994).

Holden etal., *Science*, vol. 264, pp. 1696–1697, Jun. 1994.

*Primary Examiner*—Gary W. Jones
*Assistant Examiner*—Bradley L. Sisson
*Attorney, Agent, or Firm*—Arnold, White & Durkee

[57] ABSTRACT

In an important embodiment, the present invention concerns a method for diagnosing and detecting compulsive disorder susceptibility of an individual. The method comprises initially obtaining a DNA sample of said individual and then determining the presence or absence of particular human $D_2$ receptor gene alleles in said sample. Detection of said alleles in the sample are indicative of predilection to compulsive disorder. A most preferred embodiment is to detect predisposition to impulsive, addictive, and compulsive disorders such as, but not limited to, alcoholism, obesity, smoking, polysubstance abuse and drug addiction, particularly because said alleles have been found to be present in a majority of individuals clinically diagnosed with these compulsive disorders. The human $D_2$ receptor gene A1, B1, and $^{In6-Ex7}$ haplotype I alleles are most preferably detected in said sample.

34 Claims, 10 Drawing Sheets

ALLELIC DIAGNOSIS OF SUSCEPTIBILITY TO COMPULSIVE DISORDER

BACKGROUND OF THE INVENTION

The United States government has certain rights in the present invention because research relating to its development was partially supported by funds from NIDA (DA 04268 and DA 0146) and the National Institutes of Health (HL 34589).

The present application is a continuation-in-part of U.S. Ser. No. 07/909,383, filed Jun. 24, 1992, which is a continuation-in-part of applications PCT/US91/00855, filed Feb. 7, 1991; and U.S. Pat. No. 5,210,016, Ser. No. 07/826, 222, filed Jan. 23, 1992, issued May 11, 1993; which was a continuation of Ser. No. 07/477,057, filed Feb. 7, 1990, abandoned; the entire text and figures of which disclosure are specifically incorporated herein by reference without disclaimer.

LIST OF ABBREVIATIONS

λ-hD$_2$G1 18 kb probe used to detect A1 allele
λ-hD$_2$G2 probe used to detect B1 allele
A1A1 homozygous for the A1 allele
A1A2 heterozygous for the A1 and A2 allele
A2A2 homozygous for the A2 allele
ADD attention deficit disorder
ADHD attention deficit disorder with hyperactivity
AER auditory evoked response
ANOVA Analysis of Variance
BEAM™ a registered trademark of Nicolet Corporation
B1B1 homozygous for B1 allele
B$_{max}$ Number of receptors
BMI body mass index
C1C1 homozygous for the C1 allele
CCPT contingent continuous performance task
COA children of alcoholics
COKE predominant cocaine
CP1 CP2 centro-parietal 1 and centro-parietal 2
CPT continuous performance task
DA dopamine
dCTP deoxycytosine triphosphate
DRD2=Dopamine D$_2$ Receptor
DSM III-R Diagnostic standard manual criteria, level III
DSM-IV-R Diagnostic standard manual criteria, level IV
DZ dizygotic twins
EDTA ethylenediaminetetraacetic acid
EEG electroencephalogram
EP evoked potentials
ERP event related potentials
ETOH Ethanol
fmol femtomole ($10^{-15}$ mole)
FTC1 FTC2 fronto-temporal
GABA gamma aminobutyric acid
GAMA gamma aminobutyric acid
GAP generalized anxiety disorder
HAD high-alcohol drinking
HEOG Horizontal Extraoculogram
IACD impulsive-addictive-compulsive disorders
IBI International Biotechnologies, Inc.
ISI interstimulus interval
kb=Kb Kilobase or Kilobit
Kd Dissociation constant
LDL low density lipoprotein
LSA least severe alcoholics
MSA most severe alcoholics
MZ monozygotic twins
p Probability
PASA PCR™ amplification of specific alleles
PCR™ Polymerase chain reaction (a registered trademark of Hoffmann-LaRoche)
PIC polymorphic information content—a measure of the probability that informative alleles are segregating in a family
p$^M$ picomolar ($10^{-12}$ M)
PNPS psychiatrically-ill non-polysubstance abusing subjects
PO1 PO2 parieto-occipital
PPS psychiatrically-ill polysubstance abusing subjects
PTSD post traumatic stress disorder
PV+ predicitive value positive
PV− predicitive value negative
QTL quantitative trait CDCl
RDS Reward Deficiency Syndrome
RFLP restriction fragment length polymorphism
RT reaction times
SD standard deviation
SE standard error
SEM standard error of the mean
SOT spatial orientation task
SPM significant probability topographic map
SRA sons of recovering alcoholic fathers
SSA sons of active alcoholic fathers
SSC saline solution containing sodium citrate
SSD sons of social drinking fathers
SSDNA salmon sperm DNA
TBA total brain abnormalities
TCP1 TCP2 tempro-parietal
TE Tris-EDTA Buffer
ug=μg microgram
UV ultraviolet
VETO Vertical Extraoculogram
VER visual evoked response
WISC-R Wechsler Intelligence Scale for Children-Revised
$\chi^2$ Chi Square analysis 1. Field of the Invention The present invention relates to molecular genetic evidence, through the use of RFLP and PASA analyses, that alleles in the human dopamine (DRD2) receptor gene are more significantly associated with compulsive disorders than with controls. The occurrence of these compulsive disorder-associated polymorphisms has a statistically significant predictive value in the classification of subtypes of compulsive disorders.

The identification of genetic markers that are closely linked to compulsivity means that the gene's inheritance can be followed, leading to simple tests for diagnosing vulnerable carriers and potential disorder victims, and may lead to gene therapy. A diagnosed genetic potential susceptibility to substance abuse can encourage behavioral intervention to prevent the onset of disorder on the part of the individual diagnosed or, in the case of adopted children, on the part of the adoptive parents.

Classification on the basis of DRD2 phenotype can be useful in determining treatment regimens most suited for an individual diagnosed with an impulsive, addictive, or compulsive disorder.

2. Description of the Related Art a. The Nature of Impulsive Addictive and Compulsive Behaviors The tendency of certain individuals to display impulsive, addictive or compulsive disorder behavior(s) is well known, and includes individuals with an excessive desire for substances classed as psychoactive drugs including, but not limited to alcohol and opiates. Likewise, addictive behavior such as smoking, polysubstance abuse, nicotine addiction, overeating and the like is well known. Whether alcoholism is a psychiatric illness or a biological disorder has been a controversial question, but there is some agreement that there are probably similar biochemical mechanisms for alcohol and opiates in terms of behavioral and pharmacological activities.

b. The Utility of Restriction Fragment Length Polymorphism in Detecting Genetic Disorder Restriction Fragment Length Polymorphism (RFLP) analysis offers a powerful molecular genetic tool for the direct analysis of the human genome to determine elements that provide predisposition to genetic disorder. This technique has been used to demonstrate a structural mutation in the gene that codes for an enzyme involved in alcohol metabolism (aldehyde dehydrogenase) which leads to the loss of this enzyme's ability to metabolize acetaldehyde. This altered gene is prevalent among Orientals and may explain the well-known alcohol-flush syndrome as a protective factor in this population. Prior to the present inventors' work, no specific gene abnormality had been identified which could regulate compulsive behavior, or was associated with impulsive, addiction, or compulsive disorder in humans.

c. The Role of Neurotransmitters

It is well recognized that neurotransmitter actions form the neurochemical basis of behavior and that derangements of their functioning is central to a variety of psychiatric and behavioral disorders, including addiction to psychoactive drugs and excess food (Blum, 1989). Specifically, dopamine, serotonin, norepinephrine, gamma aminobutyric acid (GABA), glutamine, and opioid peptides are thought to play crucial roles in addictive disorders, particularly as regards to alcohol, heroin, and cocaine abuse (Geller et al., 1972). Recent data suggests a substantive effect of amino acid precursors and enkephalinase inhibitors on recovery from alcohol, cocaine, and food addictions (Blum et al., 1988; Blum et al., 1989a).

One of the most intriguing discoveries of neurobiology is that several neurotransmitters, which play vital roles in brain functioning and in mood regulation, can be dramatically influenced by the circulating levels of their precursor amino acid nutrients (Wurtman, 1983).

It is well known that drugs can induce neurotransmitter deficits in deep limbic structures (Koob et al., 1987; Blum and Kozlowski, 1990), leading to focal electrophysiological deficits. These topographical changes may be an important marker or component which motivates an individual's desire to engage in psychoactive agent-seeking behavior. It has been suggested that "kindling phenomena" of the limbic system may be a factor in both the "craving" and "withdrawal" of substance abusers (Ballenger and Post, 1980).

Evidence has been provided (Gerez and Tello, 1992) that supports the "kindling" model of drug-seeking behavior when it was found that structural abnormalities and/or neuropsychological deficits were observed in only those individuals with focal topographical changes. Moreover, it was found that focal EEG and evoked potential changes predicted good response to anticonvulsants, while the presence of epileptiform (EEG) activity without focal changes did not. Focal evoked potential abnormalities probably have a clinical utility in predicting anticonvulsant responsive treatment in the substance abusers as well. In this regard, over two decades earlier, anticonvulsants were explored as potential withdrawal agents, especially in the treatment of alcoholism. More recently, the iminostilbene derivative carbamazepine has been used to reduce craving response of severe cocaine abusers (Chu, 1979). Carbamazepine (CBZ) may be used as the drug of choice in non-delirious alcohol withdrawal (Stuppaeck et al., 1992). However, the response to CBZ treatment has been variable, which may suggest subpopulations of responsive or unresponsive, possibly based on electrophysiological disturbances which can be identified by standard electrophysiological activity mapping.

Studies using sophisticated techniques in animals, including microdialysis measurements, have demonstrated changes in neurotransmitter output following precursor amino acid loading (Hernandez et al., 1988). In addition, behavioral changes have been demonstrated in animals following systemic and direct central nervous system delivery of precursor amino acids (Blum et al., 1972). While certain L-amino acids are neurotransmitter and neuromodulator precursors, their racemates, the D-amino acids also have biological activity. In particular, D-phenylalanine and D-leucine decrease the degradation of opioid peptides which are central to regulation of mood and behavior (Blum et al., 1977; Carenzie et al., 1980).

Brain electrical activity mapping, including quantitative EEG and cortical evoked potentials, has demonstrated the existence of subtle neurological changes in a wide variety of subjects (Braverman, 1990b), including schizophrenics (Daniels et al., 1988; Stoudemire et al., 1983; Braverman, 1990a; Morstyn et al., 1983; Karson et al., 1987); criminals (Neshige et al., 1991), depressives (Vasile et al., 1992); Alzheimer's (Duffy et al., 1984; deToldeo-Morrell et al., 1991); toxic exposures (Bernad, 1989; Morrow et al., 1992; Knoll et al., 1984); metabolic encephalopathy (Kugler et al., 1992); AIDS (Messenheimer et al., 1992); attention deficit disorder and its response to medication (Buschbaum and Wender, 1973; Halliday et al., Prichep et al., 1976), and alcoholism and drug abuse (Abraham and Duffy, 1991; Begleiter and Porjesz, 1988; Begleiter and Porjesz, 1990; Braverman et al., 1990; Braverman et al., 1990; Cadaviera et al., 1991; Cohen et al., 1991; Ehlers and Schuckit, 1990; Maurer et al., 1990; Noldy et al., 1990; Parsons et al., 1990; Pfefferbaum et al., 1991; Pollock et al., 1983; Struve and Straumanis, 1989; Struve and Straumanis, 1990; Whipple et al., 1988).

Well-developed criteria for brain electrophysiological mapping has therefore been established for psychotic or affective disturbances, impulse control disorders, as well as other organic behavioral disorders (Abraham and Duffy, 1991; Begleieter and Porjesz, 1988; Begleiter and Porjesz, 1990; Bernad, 1989; Braverman, 1990a; Buschbaum and Wender, 1973; Cadaviera et al., 1991; Cohen et al., 1991; Daniels et al., 1988; deToldeo-Morrell et al., 1991; Duffy et al., 1984; Ehlers and Schuckit, 1990; Garber et al., 1989; Halliday et al., 1976; Karson et al., 1987; Knoll et al., 1984; Kugler et al., 1992; Maurer et al., 1990; Messenheimer et al., 1992; Morrow et al., 1992; Morstyn et al., 1983; Neshige et al., 1991; Noldy et al., 1990; Parsons et al., 1990; Pfefferbaum et al., 1991; Pollock et al., 1983; Pollock et al., 1983; Prichep et al., 1976; Stoudemire et al., 1983; Struve and Straumanis, 1989; Struve and Straumanis, 1990; Vasile et al., 1992; Whipple et al., 1988). Moreover, the American Psychiatric Association Task Force (1991) recently embraced the utilization of brain electrical activity mapping as a promising technique to elucidate brain illnesses.

While little is known about the precise neural mechanisms involved in the genesis of the P3 gene, evidence has suggested the involvement of the dopaminergic system (Stanzione et al., 1991). The dopaminergic system, and in particular the $D_2$ receptor gene, plays a major role in the brain-reward mechanisms whereby deficits in dopamine function results in abnormal drug, alcohol-seeking, obesity, and other compulsive behaviors. The $D_2$ receptors have been profoundly implicated (DiChiara and Imperato, 1988a, 1988b). The present inventors have suggested that the $D_2$ dopamine receptor gene (which is known to be localized in the region of chromosome II at the q22–q23 segment), should in fact, be termed a "reward" gene. It is further known to have four different allelic forms, A1, B1, Intron 6-Exon 7 ($^{In6-Ex7}$) and C1 (Grandy et al., 1989a; Hauge et al., 1991; Sakar and Sommer, 1991; Parsian et al., 1992).

d. Familial Inheritance of Compulsive Disorder

Over 103 years ago, a paper appeared in the *Journal of the American Medical Association* which shocked the scientific community. The paper suggested that children born to families with parental alcoholism have a 70% risk of becoming an alcoholic in later life (Suthers, 1890). This finding constituted the first potential evidence for familial alcoholism.

Since that time numerous studies have appeared in the scientific literature, with a general consensus that alcoholism has a familial component (Blum, 1990). In this regard, the work of Popping, Goodwin, Schuckit, Cloninger and Bowman evaluating the potential genetic contribution to alcoholism in twin studies, adoption studies, family linkage studies, in both male and females overwhelmingly suggest that:

1) alcoholism runs in families;

2) if there is at least one alcoholic biological parent, there is a 4 times greater risk for males to become alcoholic relative to siblings of non-alcoholic parents, and a three times greater risk for females;

3) Although still controversial, alcoholics have been classified into two basic types—Type I-milieu-limited-alcoholism—less severe and modest alcoholism occurring in both male and females where environmental factors play a major role with low genetic contribution and the onset of the disorder occurs after twenty-five years of age. Type II- male-limited-alcoholism—the most severe alcoholism affecting mostly males where genetics play a major role and environment plays a less important role and the onset of the disorder occurs prior to twenty-five years of age;

4) the genetic contribution to female alcohol abuse is negligible—0% in one study, whereas male alcohol abuse has an approximate 38% genetic contribution; and 5) severe alcoholism has a 60% genetic contribution in females (Kendler et al., 1992) and in males (Pickens et al., 1991).

e. A Link Between Compulsive Disorder and Genetic Susceptibility

In terms of trying to link lesions in the brain with genetic susceptibility, numerous investigators have found that the brain electrical activity centered on the late positive complex concerned with ERPs, which includes the P300 wave, has been observed to be abnormal in male alcoholics and their sons (Whipple et al., 1988; Begleiter et al., 1987; Elmasian et al., 1982). Most recently, Berman et al. (1993) found evidence that young adolescents of alcoholics having P300 deficits were significantly more vulnerable for substance abuse than adolescents of non-alcoholic parents without P300 deficits. The authors suggested that their work indicates that the P300 wave has utility as a vulnerability marker for substance abuse disorders and its use will depend on combining this marker potential with other measures (i.e., genetic testing).

A progressively reduced number of receptors was found in subjects with A2/A2, A1/A2, A1/A1 genotypes respectively. Moreover, the DRD2 receptor gene A1 allele variant is associated with not only alcoholism and polysubstance abuse but also with other neuropsychiatric disorders including ADHD in children as well as Tourette's syndrome when compared to assessed controls (Comings et al., 1991). In contrast, Gelernter (Gelernter et al., 1991) reported no association between the A1 allele of the DRD2 gene in poorly characterized non-severe alcoholics compared to non-assessed controls. However, a combined analysis of extant studies, showed A1 allele in alcoholics (n=338) and the controls (n=471) to be 45% and 27% respectively; a difference that was highly significant ($p<10^{-7}$) (Cloninger, 1991). According to Cloninger, "this is the first time that multiple independent replications and the totally accumulated data from molecular genetic studies have confirmed that a specific gene influences the development of a common psychiatric disorder."

To more systematically characterize the prevalence of the A1 allele in alcoholics, Blum, Noble and associates reported (Blum et al., 1991) that the A1 allele associated to a much greater degree in severe alcoholics than less severe alcoholics compared to 63% of severe alcoholics. This difference was significant at p=0.007. In fact a Chi-square ($\chi^2$) for linear trend shows that increasing the degree of alcoholism severity corresponds to a significant increase of A1 allele sample prevalence (p<0.001). Moreover, to determine whether children at risk for developing alcoholism have a higher association of the A1 allele compared to a non-alcoholic sample, the presence or absence of this allele in children of alcoholics (COAs) was determined. The A1 allele in the Blum et al. study associated with 55% of COAs compared to only 21% of known controls. Following this study, Turner and coworkers (Turner et al., 1992) found a surprisingly low A1 allele prevalence in a small number of alcoholics from the San Diego Alcoholism Treatment Unit. Scrutiny of the paper reveals that although Turner and associates claimed to assess severity, they excluded from the study all individuals having a record of anti-social personality disorder and severity was poorly determined. Moreover, the age of onset of alcoholism was on the average 35 years suggesting a "milieu-limited" alcoholic type. It was further noted that Turner and associates failed to assess any age matched controls and relied exclusively on general population assessed and unassessed controls taken from other studies.

Following these studies, in 1991 the first technical conference organized by the NIDA was held in Baltimore. This conference concluded that the meta analysis on all extant studies revealed that despite the initial improbability of the finding and the cautions relating to ethnic variables, evidence from a number of different laboratories now appears to support an association between DRD2 alleles marked by TaqI RFLPs and substance abuse. According to a report by Uhl, "... associating a DRD2 variant with substance abuse vulnerability would identify, for the first time, an individual gene which impacts a polygenetic disorder. These are the kinds of disorders that currently challenge the limits of molecular and behavioral genetics (Uhl et al., 1992)."

Given that the A1 allele of the DRD2 varies significantly in frequency from one population to another, (e.g., 9% in Yemenite Jews [known to have very low alcoholism rates] and 74% in Cheyenne American Indians [known to have high alcoholism rates] (Blum et al., 1990 and Goldman et al., 1992) it is possible to mask a real association between alcoholism and this allele or demonstrate an apparent association between the two, simply as a function of the population characteristics of the subject and control groups chosen for the study. The present inventors, therefore, realized the need to test this association in sample groups where assessment of severity is characterized and population heterogeneity was minimized (See FIG. 1 and Table 1).

In a recent study, the A1 allele of the DRD2 gene was once again positively associated with very ill hospitalized severe alcoholics compared to a matched group of very ill hospitalized less severe alcoholics and non-alcoholics (Noble et al., 1994). The prevalence of the A1 allele in this study of 80 non-alcoholics and 73 alcoholic patients was 30.0% and 52.1%, respectively (p=0.0009). In four subgroups of these patients, the prevalence of this allele was: less severe polysubstance abuse (LPSU)=18.2%; more severe polysubstance abuse (MPSU)=34.5%; less severe alcoholic (LSA)=44.4%; and more severe alcoholic (MSA)= 58.3%. Linear trend analysis showed that as the use of substance and severity of alcoholism increases, so does A1 prevalence (p=0.001). Specific group comparisons showed A1 prevalence in MSA to be about 3-fold (p=0.007) and 1.5-fold (p=0.04) higher compared to LPSU and MPSU groups, respectively. In a combined analysis of independent studies, A1 prevalence in MSA was higher when compared to LSA ($p<10^{-2}$), MPSU ($p<10^{-4}$) and LPSU ($p<10^{-8}$) groups. None of the medical or neuropsychiatric complications of alcoholism associated with the A1 allele.

The severity of alcohol dependence in alcoholics and of substance use behaviors in controls are important variables in DRD2 association. The present review and converging lines of evidence suggest that the DRD2 could represent the most prominent single gene determinant of susceptibility to severe alcoholism. In this regard, a relevant meta analysis of the six independent published exant association studies of Caucasians and DRD2 and severe alcoholism, seen in Table 2 (Noble, 1993), revealed a strong positive association. In four studies where alcoholics were excluded from the 148 controls, 34 (23.0%) subjects had the A1 allele, while 144 (77.0%) subjects had the A2 allele. In the same studies of 115 severe alcoholics, 68 (59.1%) subjects had the A1 allele, while 47 (40.9%) subjects had the A2 allele. The difference between these combined groups was significant (Yates $\chi^2$ corrected for continuity=3.79, odds ratio=2.05, 95% confidence interval=1.00–4.21, p=0.052). With regard to 501 total sources, a positive association of the A1 allele of DRD2 with severe alcoholism was obtained with an odds ratio of 3.32 (Yates $\chi^2$ corrected for continuity=36.1, 95% confidence interval=2.20–5.01, $p<10^{-8}$). However, other genes and environmental factors, when combined, still play the larger role.

A major question raised by some investigators focuses on the fact that the A1, A2 polymorphism is at a TaqI restriction site now known to be several thousand base pairs downstream from the protein coding portion of the $D_2$ gene. According to Karp, " . . . it is extremely unlikely that this polymorphism itself results in a functional difference between two alleles. A critical test of the significance of the apparent association between the A1 allele and medical complications of alcoholism would therefore be the demonstration that the chromosome bearing the A1 and A2 alleles actually encode $D_2$ receptors which differ structurally, or that there is some difference in the quantity or tissue distribution of the receptor encoded by the two alleles" (Karp, 1992).

In terms of the comment that the polymorphic loci is in the 3' region downstream from the coding region of the gene has been put aside in part by the recent findings of a second TaqI polymorphism B1 allele between the first and second exon very near to the first coding exon (Hauge et al., 1991), since this new polymorphism associates both with polysubstance abuse (Smith et al., 1992) and severe alcoholism (Blum et al., 1993;). Finally, as previously noted (Noble et al., 1991a, 1991b) the presence of A1 allele is associated with a reduction in the number of DRD2 receptors in non-alcoholic controls, which is exactly what was suggested as a prerequisite for a functional meaning for the A1 allele (Karp, 1992). Furthermore additional polymorphic loci of the DRD2 gene, specifically the D2 $^{In6-Ex7}$ haplotype I was assessed for an association with severe alcoholism and number of DRD2 receptors. In this regard Flanagan and associates found that this polymorphism also associated with not only severe alcoholism, polysubstance abuse, but with a decease in the number of DRD2 receptors as well (Flanagan et al., 1992). Other unpublished work in the laboratories of Blum and Noble also found an association of the B1 allele and reduction of the number of DRD2 receptors independent of alcoholism. In addition, Parsian and associates preliminarily reported (Parsian et al., 1992) a strong association of a polymorphic locus C1, recognizing the region spanning the entire 2 and 3 exons, with severe alcoholism to an even greater degree than the A1 allele. In fact, homogenous copies of the C1 allele were more highly associated with alcoholics than with non alcoholics at a p<0.002 (Suarez et al., 1994).

f. Polysubstance Abuse and DRD2 Gene Variants

Certainly, the DRD2 gene variants are not specific for alcoholism per se but prevails in polysubstance abuse as well. A report similar to the findings by Blum's group showed association of the TaqI A1 and B1 alleles for the DRD2 gene with severe alcoholism, heavy polysubstance users and subjects with DSM-III-R, psychoactive substance use diagnoses, displayed significantly higher TaqI A1 and TaqI B1 frequencies than control subjects (Smith et al., 1992). These results were consistent with a role for a DRD2 variant marked by these RFLPs in enhanced substance abuse vulnerability (Smith et al., 1992). In this regard, Comings et al. also reported an association between A1 allele of the DRD2 gene and the number of neuropsychiatric disorders, including polysubstance abuse. The prevalence of the A1 allele in patients with drug addiction compared to controls known not to be alcoholic yielded a significant difference (p=0.005) (Comings et al., 1991).

Furthermore, other work by Comings et al. found that multiple logistic regression analysis revealed a highly significant association between multiple substance abuse, based on money spent on drugs, and the presence of the $D_2$ A1 allele p=0.0003, and age of onset of drug abuse (p<0.001). $D_2$ A1 carriers exceeded $D_2$ A2A2 subjects for a history of being expelled from school for fighting (p=0.001), and of those ever jailed for violent crimes, 53.1% carried the $D_2$ A1 allele versus 28.8% of those jailed for non-violent crimes (p=0.011). This increased to 69.2% for those who were both jailed for violent crime and expelled from school. They concluded that possession of the $D_2$ A1 allele is significantly associated with the severity of polysubstance abuse and some aggressive behaviors.

Further advancing this possibility, Noble, Blum and associates (Noble et al., 1993) found a strong association of the A1 allele and B1 allele in cocaine dependence. The prevalence of the A1 allele of the DRD2 gene in cocaine dependent subjects (n=53) was 50.9% and was significantly different ($p<10^{-4}$) from the 16.0% prevalence found in non-substance abusing controls (n=100). In a larger control group (n=365) consisting of non-substance abusers and subjects from the general population, 26.8% prevalence of the A1 allele was also significantly different from that of cocaine dependent subjects (p<0.001). The prevalence of the B1 allele of the DRD2 gene in these cocaine dependent subjects (n=52) and in a non-substance abusing group (n=53) was 38.5% and 13.2% respectively (p<0.01). Logistic regression analysis in the cocaine dependent subjects identified potent routes of cocaine use and the interaction of early deviant behaviors and parental alcoholism as significant risk factors associated with the A1 allele.

The A1 allele contributed to 16.7% in the 0-risk score group, 35.0% in the 1-risk score group, 66.7% in the 2-risk group and 87.5% in the 3-risk group. Risk score differences with allelic classification yielded a Pearson Chi-square of 10.9, df=3 with a p=0.012. Verification of the association of the count of risk factors with the allelic classification was made using a Chi-square test for linear trend. Increasing risk scores are positively and significantly related to A1 classification with a Chi-square value of 10.5, df=1, p=0.001. The results indicate that the minor alleles A1 and B1 of the DRD2 gene are strongly associated with cocaine dependence in the samples studied. The polymorphic pattern of this dopamine receptor gene suggests that a gene conferring susceptibility to cocaine dependence is located on the q22–q23 region of chromosome 11.

Uhl and associates accessed the DRD2 locus and substance abuse vulnerability and concluded that:

1) The TaqI A1 and B1 DRD2 RFLPs are interesting reporters for events in significant portions of the DRD2 gene locus in Caucasians. TaqI A and B genotypes could reliably mark a structural or functional gene variant at the DRD2 locus that could be directly involved in altering behavior.

2) A1 and B1 markers appear more frequently in drug abusers than in control populations in each of the four currently-available studies (Smith et al., 1992). Meta analyses of these data suggest that differences between drug abuser and control populations are highly significant for both the four studies examining A1 and the two studies examining B1 frequencies.

3) The most severe abusers of addictive substances may manifest higher A1 and B1 DRD2 gene marker frequencies, while "control" comparison groups are studied carefully to eliminate individuals with significant use of any addictive substance appear to display lower A1 and B1 frequencies than unscreened control populations (Uhl et al., 1993).

4) Current meta analyses based on the three studies reported in full suggest that drug abusers may display an odds ratio of drug abuse likelihood for individuals possessing an A1 allele of 2.4 and 3.3-fold odds ratio for those having a B1 allele (p<0.001) in both cases (calculated per 34).

Failures of Classical Studies in Linking the Dopamine Receptor Gene and Substance Abuse Failure of classical linkage studies may in part be due to an inability to correct for false-positives in non-drug abusing probands. The phenotype of compulsive disorder has a wide array of abnormal behaviors other than drug and alcohol seeking and therefore inclusion/exclusion criteria is quite difficult. Furthermore, researchers agree that vulnerability to drug and alcohol seeking behavior or compulsive disorder is likely to be the result of multiple factors and is polygenic in nature, of which the DRD2 genotype variants are one (Pickens et al., 1991; Uhl et al., 1994; Cloninger, 1991).

Likewise, a number of recent reports have failed to find a strong association of the A1 allele of the $D_2$ dopamine receptor gene and alcohol (Bolos et al., 1990; Cook et al., 1992; Gelernter et al., 1991; Goldman et al., 1992; Goldman et al., 1993; Schwab et al., 1991; Suarez et al., 1994; Turner et al., 1992 and Neiswanger et al., 1993). Two primary reasons for their inability to replicate the present invention have become apparent: first, the inappropriate screening of controls to eliminate existing alcohol, drug and tobacco abuse in the probands studies; and second, sampling errors in terms of characterization of alcoholics for chronicity and severity of the disorder.

h. What is Lacking in the Prior Art

One thing lacking in the prior art is a reasonably reliable method for detecting a genetic susceptibility to compulsive disorders. Also lacking in the prior art is a means of identifying the various types of compulsive diseases. As described herein, aberrations in the DRD2-related dopaminergic system may lead to compulsive disorder. However, not all victims of compulsive disease have such aberrations, nor do all control subject or non-compulsive disorder victims. Thus, a victim of a compulsive disorder may be DRD2 aberrant ($DRD2_{ab}$) or DRD2 normal ($DRD2_{norm}$), with a significant majority being $DRD2_{ab}$.

Such identification potentially allows more effective treatment of victims of impulsive-addictive-compulsive behaviors. For example, it is known that certain $DRD2_{ab}$ mammals contain a lower density of DRD2 receptor in the brain than do control mammals, and that DRD2 receptor densities may be increased by dietary control (e.g., by a high-protein diet or administration of compounds such as Tropogen™). Thus, if a compulsive disorder victim was classified as $DRD2_{ab}$, dietary or psychopharmaceutical manipulations aimed at increasing DRD2 receptor density or making other adjustments in the dopaminergic system would be recommended. For $DRD2_{norm}$ compulsive disorder victims, more traditional psychiatric counseling treatment methods would be appropriate.

Therefore, there still remains a need in the art to detect the genetic predisposition for impulsive-addictive-compulsive (IAC) disorders such as Reward Deficiency Syndrome. Likewise there remains a need for establishing a correlation between the various types of IACD. Moreover, the correlation between DRD2 allele variants and compulsive disorders such as overeating, tobacco abuse, and polysubstance abuse has to be established.

SUMMARY OF THE INVENTION

The present invention overcomes the drawbacks inherent in the prior art by providing a method of detecting a genetic potential susceptibility to IACD in a human subject. IACD may include drug dependence, polysubstance abuse, alcoholism, severe alcoholism, a $DRD2^{In6-Ex7}$ haplotype I subtype of alcoholism, cocaine dependence, compulsive overeating disorder, Tourette's syndrome, tobacco abuse, attention deficit disorder with hyperactivity (ADHD), post-traumatic stress disorder (PTSD), pathological gambling and the like.

The present invention relates to a pioneering discovery of allelic association with compulsive disorder and provides a method for detecting on a molecular basis a genetic potential susceptibility to compulsive disorders such as alcoholism. In particular, the detection of certain alleles associated with the genes encoding the human dopamine $D_2$ receptor protein is an indication of a genetic potential susceptibility to compulsive disorder.

The present invention overcomes the disparity between classical linkage studies and those of association as presented herein. While a number of linkage studies excluded the DRD2 gene with alcoholism (Bolos et al., 1990; Suarez et al., 1994; Neiswanger et al., 1993; Parsian et al., 1992) linkage was found in one report using affected sib-pair analyses in both heavy drinking (p<0.002) and alcoholism (p>0.0002) (Cook et al., 1993). Further support is derived from a variety of independent studies.

The present invention identifies the surprising correlation between the predisposition to IACD and alleles of the human dopamine $D_2$ receptor gene.

The method comprises obtaining DNA from a subject and detecting in said DNA a human dopamine $D_2$ receptor gene allele which indicates a potential susceptibility to IACD. An allele is an alteration in DNA that is correlated with the potential susceptibility to IACD. The human dopamine $D_2$ receptor gene allele may be an A1 allele, a B1 allele, a C1 allele, or a $DRD2^{In6-Ex7}$ haplotype I allele, for example. The detecting method may, for example, involve RFLP or PASA. Other $D_2$ receptor gene alleles useful in this fashion may be found by further exploration using diverse restriction endonucleases, for example.

In a preferred embodiment, the present method comprises the detection of a genetic potential susceptibility to an impulsive, addictive, or compulsive disorder by detecting the presence of a human dopamine $D_2$ receptor gene A1 on B1 alleles. The method also detects a genetic potential susceptibility to IACD by detecting the presence of a human dopamine $D_2$ receptor gene B1 allele in a white population. The method also relates to the detection of a genetic potential susceptibility to a subtype of alcoholism named $DRD2^{In6-Ex7}$ wherein the allele detected is a $DRD2^{In6-Ex7}$ haplotype I allele. The method also relates to the detection of genetic potential susceptibility to IACD, including cocaine dependence, by detecting a human dopamine $D_2$ receptor gene A1 allele, B1 allele, or A1 and B1 alleles.

The detection of said human dopamine $D_2$ receptor gene A1 allele comprises obtaining DNA of a subject, subjecting said DNA to digestion by TaqI restriction enzyme, separating resultant DNA fragments, hybridizing said separated DNA fragments to a labeled recombinant phage $\lambda$-$hD_2G1$ (ATCC#61354 and 61355) or a fragment thereof specifically binding a 6.6 kb A1 allele of the human dopamine $D_2$ receptor, and determining the presence of said A1 allele of the human dopamine $D_2$ receptor. In particular, the fragment of recombinant phage $\lambda$-$hD_2G1$ (ATCC#61354 and 61355) may be a BamHI fragment having an about 1.7 kb size.

In another preferred embodiment, the invention relates to a method of detecting a genetic potential susceptibility to severe compulsive disorder in a human subject, comprising obtaining the DNA from said subject and detecting in said DNA a human dopamine $D_2$ receptor gene B1 allele, wherein said B1 allele indicates a potential susceptibility to severe alcoholism. In particular, the human subject is white. However, it is contemplated that the same genotype would exhibit similar phenotypes in other ethnic groups.

The detection of the B1 allele comprises obtaining DNA from a subject, subjecting said DNA to digestion by TaqI restriction enzyme, separating the resultant DNA fragments, hybridizing said separated DNA fragments to a labeled recombinant phage $\lambda$-$hD_2G2$ or a fragment thereof specifically binding a 4.6 kb B1 allele of the human dopamine $D_2$ receptor, and detecting the presence of said B1 allele of the human dopamine $D_2$ receptor in the DNA fragments. In particular, the fragment of recombinant phage $\lambda$-$hD_2G2$ is a BamHI fragment having an about 3.7 kb size.

The present invention describes the association of a TaqI A1 polymorphism, as well as other variants, of the DRD2 with a number of addictive behaviors (e.g., alcoholism, severe alcoholism, polysubstance abuse, drug addiction, cocaine dependence, nicotine abuse, overeating, and carbohydrate bingeing).

The present invention also provides the first report in healthy humans of the effects of daily ingestion of a specific precursor amino acid supplement having enkephalinase-inhibition properties, Tropogen™, on cognitive event-related potentials (ERP's) associated with performance on neuropsychological tests.

The present invention provides results of cognitive event-related potential (ERP) measured in response to computerized tasks—the spatial orientation task (SOT) and the contingent continuous performance task (CCPT)—in normal young adult volunteers, where each subject acted as his own control for testing before and after 28–30 days of Tropogen™ ingestion. For both tests, statistically significant differences were seen after Tropogen™-enhanced amplitude of the P300 component of the ERP's.

Specifically, the present invention demonstrates late vertex positivity (i.e., P300 component) in the re-test condition was found to be larger in amplitude for both the right facilitated condition [F(1,17)=16.31, p=0.0009] and for the left facilitated condition [F(1,19)=8.53, p<0.005]. Furthermore, in the CCPT parameter, Tropogen™-induced enhanced P300 amplitude when comparing the pre-test to the re-test condition [F(1,15)=7.41, p=0.015]. The changes observed in this study in "normal" controls strongly suggest that the amino acid supplement Tropogen™, which has been shown to facilitate the recovery of known cocaine addicts, enhances neuroelectrophysiologic function consequent to its ingestion.

The present invention identifies for the first time a predisposition towards a condition for which one of the inventors coined the term "Reward Deficiency Syndrome"(RDS) (Kocher, 1994). RDS profoundly implicates the dopaminergic system, and in particular the dopamine $D_2$ receptor as reward mechanisms in the meso-limbic circuitry of the brain. Dysfunction of the $D_2$ dopamine receptors lead to aberrant substance seeking behavior (e.g., alcohol, drug, tobacco and food) and other related behaviors (e.g., Tourette's Syndrome and ADHD). These disorders encompass a broad range of IAC disorders. Surprisingly, RDS involves a number of impulsive, compulsive, and addictive behaviors as well as at least three personality disorders (e.g., conduct disorder, antisocial personality, and aggressive behavior). The surprising breadth of this disorder and its relationship to DRD2 receptor density is summarized in FIG. 2.

The present invention provides the first evidence that polymorphism of the $D_2$ dopamine receptor gene is an important determinant of P3 latency. Equivalent temporal abnormalities were also found when comparing both psychiatrically-ill polysubstance abusing subjects (PPS) and psychiatrically-ill non-polysubstance abusing subjects (PNPS) to controls. In the depressed subjects the most significant exacerbation of brain electrophysiological deficits were found by polysubstance abuse in the temporal and bitemporal regions of the brain (p<0.0000001).

In the present invention, 155 Caucasian male and female diagnosed neuropsychiatrically-ill patients with and without comorbid drug and alcohol/abuse/dependence were genotyped for the presence or absence of the A1 allele of the DRD2 gene. The relationship of the A1 and A2 alleles to P3 amplitude and latency was also determined. The results showed no significant difference in P3 amplitude between all groups studied with A1 and A2 allele carriers. However, prolonged P3 latency in neuropsychiatrically-ill patients (with or without polysubstance abuse) was reported for those carrying two copies of the A1 allele (homozygote) of the DRD2 gene (quadratic trend, p=0.01). The present invention provides an association of polymorphisms of the DRD2 gene and a biological marker previously indicated to have predictive value in vulnerability to substance abuse.

Another aspect of the present invention is a method of detecting a genetic potential susceptibility to a DRD2$^{In6\text{-}Ex7}$ subtype of alcoholism in a human subject. This method comprises obtaining DNA from said subject, and detecting in said DNA a human dopamine DRD2$^{In6\text{-}Ex7}$ receptor gene allele haplotype I. The presence of haplotype I indicates a potential susceptibility to a DRD2$^{In6\text{-}Ex7}$ haplotype I alcoholism subtype. The detecting of a DRD2$^{In6\text{-}Ex7}$ receptor gene allele haplotype I comprises obtaining DNA from a subject, subjecting said DNA to PCR™ amplification of specific alleles (PASA).

A further aspect of the present invention is a method of detecting a genetic potential susceptibility to IACD in a human subject. This comprises obtaining DNA from a subject, and detecting in said DNA a human dopamine $D_2$ receptor gene A1 allele. The presence of said allele indicates a potential susceptibility to cocaine dependence. The method also comprises detection of a B1 allele indicating the same potential susceptibility.

The present invention also provides for a kit for use in genetically detecting potential susceptibility to compulsive disorder in a human subject. The kit comprises a carrier compartmentalized to receive one or more container means in close confinement therein; a first container means including a restriction enzyme capable of cleaving a human dopamine $D_2$ receptor gene, a second container means including a hybridization probe for detecting a human dopamine $D_2$ receptor gene allele whose presence indicates susceptibility to compulsive disorder.

In particular, the kit would include a container holding the restriction enzyme TaqI capable of cleaving a human dopamine $D_2$ receptor gene, and a container holding the hybridization probe for the detection of the A1 allele which is the $\lambda$-hD$_2$G1 (ATCC #61354 and 61355) or a fragment thereof having binding specificity for the A1 allele. Another kit would include the restriction enzyme TaqI, and, for the detection of the DRD2 B1 allele, the hybridization probe of $\lambda$-hD$_2$G2 or an allele-binding fragment thereof.

The alleles described herein could be detected by other methods, for example, the RFLP's detected by Southern hybridization technology. Such alleles are also detectable by PCR™, PASA methodology, or sequence specific antibodies, as well as the use of a "gene reader (sequencer)" to determine actual mutations.

The present invention provides a safe and reliable method to detect susceptibility to an IACD (e.g., alcoholism drug or polysubstance susceptibility) at either the prenatal, or postnatal level.

The above described method may also be of value in genetically detecting vulnerability toward other substance abuse patterns including, but not limited to, nicotine, narcotics and other abused drugs. In a particular embodiment, the above described method may also be used to detect a vulnerability to ADHD in children. In a more particular embodiment, this method may be correlated to the presence of ADHD and/or to detect vulnerability to alcoholism with greater reliability as well as other genetic disorders such as Tourette's Syndrome. This genetic disorder has been linked to a severe form of alcoholism possibly caused by a disinhibition of the limbic system.

In summary, it is clear that alcoholism associated with comorbid disorders such as drug dependence, smoking, conduct disorder, pathological gambling, obesity and PTSD is associated with significant increases in the prevalence of the $D_2$ A1 allele. Among these disorders, individuals with comorbid severe alcoholism tend to show a higher prevalence of the $D_2$ A1 allele than those with lower degrees of alcoholism. However, when those without alcoholism are analyzed separately the prevalence of the $D_2$ A1 allele is still significantly greater than in controls for both groups.

Moreover, it is apparent from this study that ADHD, Tourette's syndrome, pathological gambling, polysubstance dependence, PTSD, obesity, conduct disorder and smoking are also related to a lack of DRD2 binding as evidenced by the differences between $D_2$ A1 and B1 carriers compared to A2 and B2 carriers in spite of the significant reduction in the number of DRD2 receptors in the former group.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

DESCRIPTION OF THE PREFERRED EMBODIMENT

Figure 1:
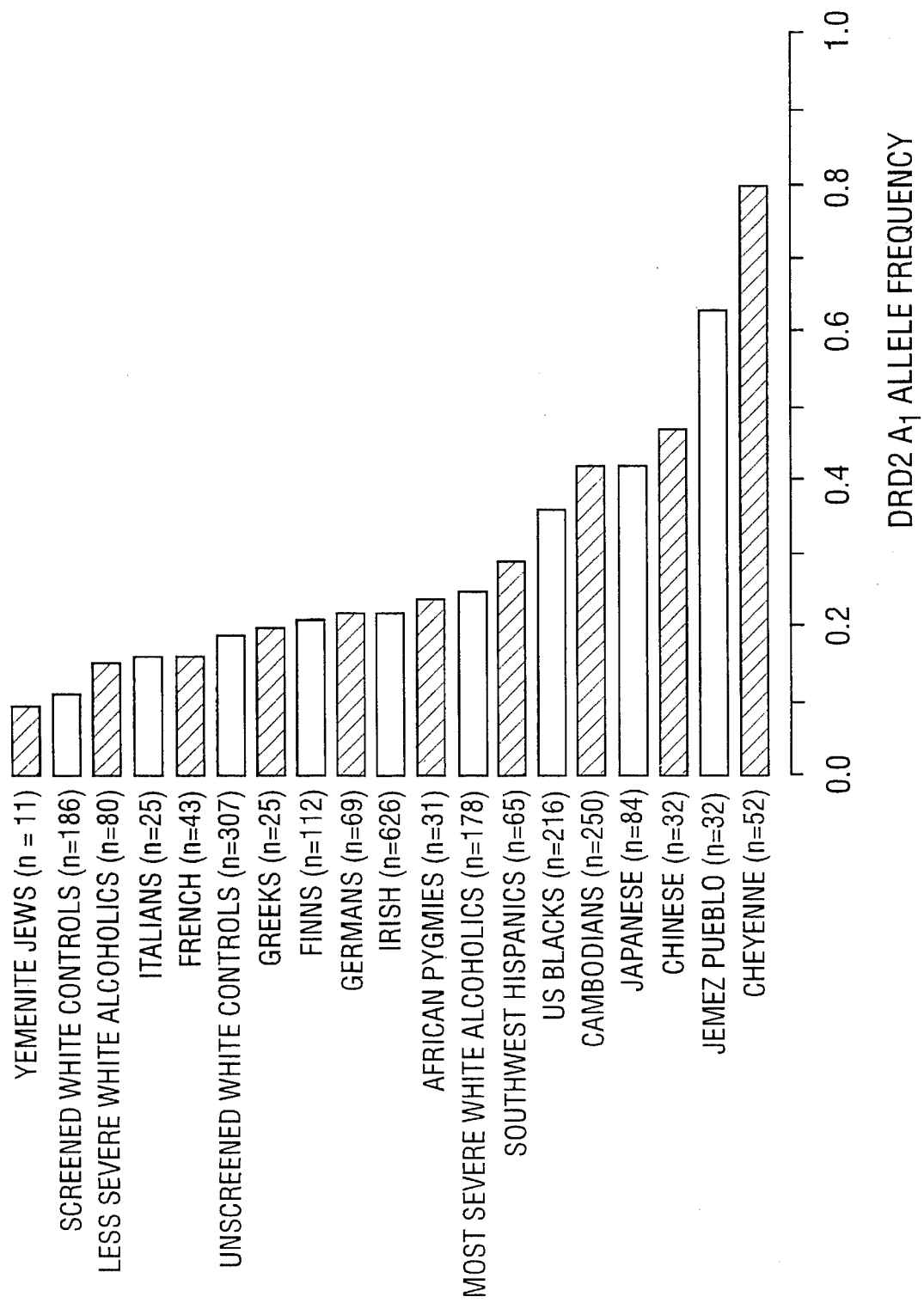
FIG. 1. Distribution of DRD2 TaqI A1 allele frequencies as a function of ethnicity.
Figure 2:
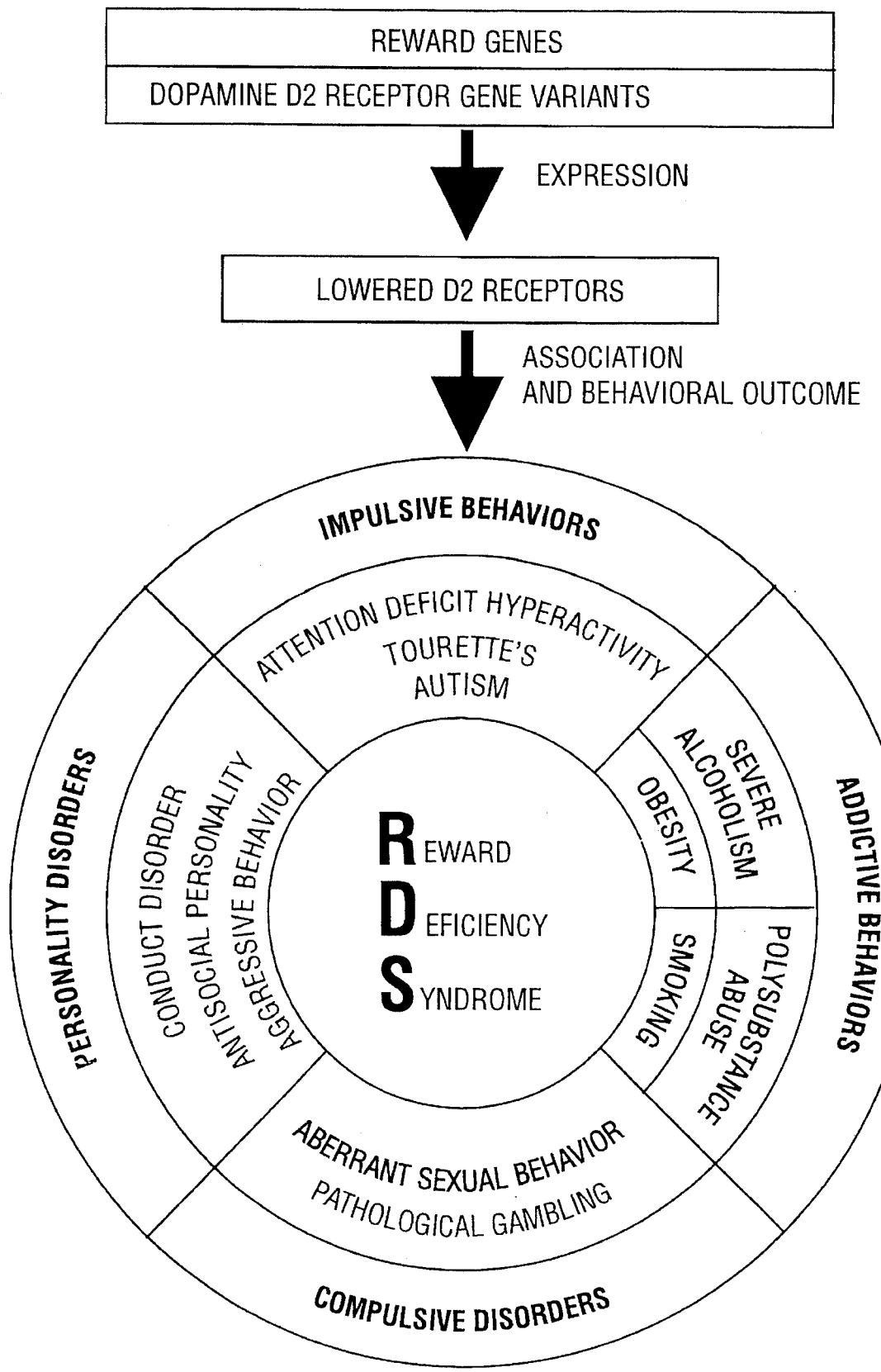
FIG. 2. Relationship between DRD2 receptor variants and Reward Deficiency Syndrome.

1. The P300 Component of the Event-Related Potential

The P300 or P3 component of the event-related potential (ERP) is a late positive waveform elicited during stimulus discrimination (Sutton et al., 1965). In terms of ERP and in particular P3 certain specific levels of electrophysiological activity are involved. Whereas the P3 occurs in response to rare targets (in a stream of frequent stimuli) and may reflect cognitive events of information processing, P3 amplitude, on the other hand, is controlled by the task relevance of the eliciting events and is inversely proportional to the subjective probability of the stimulus (Ritter and Vaughan, 1969; Courchesne et al., 1975; Squires et al., 1977a). However, P3 latency depends on the duration of the stimulus and is increased by the difficulty of the task (Donchin, 1984; Squires et al., 1977b).

Since P300, an event-related cognitive potential, has been shown to change as a consequence of psychoactive substance abuse, bringing about alterations in attention or concentration, this ERP was characterized as a consequence of ingestion of selected nutrients in healthy volunteers (Struve and Straumanis, 1990; Braverman et al., 1990a). In relevant studies, (Blum et al., 1988; Blum et al., 1989b) the use of an amino acid supplement in a 30-day in-patient treatment program of cocaine addicts was examined, with significant facilitation of the recovery process, including decreased agitation, outside focus, and craving. Since these measures are complex, frequently qualitative, subjective, and variable dependent, quantitative neurophysiological observations were correlated with behavioral performance. Therefore, this study addresses the issue of the electrophysiological and performance correlates of chronic administration on normal subjects, especially as it pertains to changes in the P300 component of the cognitive ERP.

Most interestingly, a number of studies reported on the potential heritability of the P3 in humans. Twin studies revealed that P3 latencies in monozygotic (MZ) twins were significantly more alike than those of unmatched controls (Surwillo et al., 1980; Polich et al., 1988). Moreover, in other studies, the within-pair similarity of P3 latency was significantly greater in MZ from dizygotic (DZ) twins. However, it is notable that within-pair similarity of P3 amplitude, this was not different in MZ compared to DZ twins, supportive of the view that P3 component latency has an important genetic component (Polich et al., 1988).

A reduced P3 activity or an enhanced latency has been noted in a wide variety of subjects including schizophrenics (Karson et al., 1987); depressives (Vasile et al., 1992); Alzheimer's (Duffy et al., 1984a); alcoholics (Cohen et al., 1991); drug abuses (Braverman et al., 1990a); ADHD (Prichep et al., 1976); psychiatric disorder (Garber et al., 1989); obesity (Braverman et al., 1994b); and criminals (Nesige et al., 1991). Moreover, abnormal P3 wave activity seemed to have predictive value in children of alcoholics with regard to future vulnerability to drug and alcohol-seeking behavior (Berman et al., 1993).

2. Reward Deficiency Syndrome (RDS) Linked to the $DRD^2$ Gene

In reviewing the entire molecular genetic literature following these initial studies it has become increasingly clear that the overall data supports the association of the $D_2$ dopamine receptor gene with not only alcoholism, but a variety of associated IACDs, including polysubstance abuse, smoking attention deficit hyperactivity disorder, obesity, Tourette's, pathological gambling, as well as other behavioral anomalies. The purpose of this hypothesis is to succinctly point out evidence for the putative association of the DRD2 gene with IACD (herein referred to by the present inventors as Reward Deficiency Syndrome).

RDS causes a number of addictive behaviors including alcoholism, polysubstance abuse, smoking, eating disorders as well as pathological gambling. It is considered by experts to be the number one health concern in the world. In the U.S. alone there are 18 million alcoholics, 6 million cocaine addicts, 14.9 million substance abusers, 8 million people morbidly obese and over 4 million school age children with ADHD (also termed Attention Deficit Disorder with Hyperactivity [ADDH]), and conduct disorder (Biederman et al., 1992; Faraone et al., 1991; Anderson et al., 1987). Twenty-five percent of the US population are smokers or approximately 62 million (1991). The prevalence assumption of Tourette's Syndrome in males runs from 1 in 1200 to 1 in 90 (Comings et al., 1990; Zohar et al., 1992; Caine et al., 1988; Flynn et al., 1988). The prevalence for Tourette's plus chronic tics (motor or vocal) are about 1 in 40. The prevalence for pathological gambling ranges from 0.1% to 2.7% of the population (Comings et al., 1994a; Zohar et al., 1992; Volberg et al., 1988; Volberg et al., 1989). There are an estimated 28 million children of alcoholics (Blum et al. 1990b).

Over 100 years ago, neurologist Giles de la Tourette working at Salpetriere Hospital in France first described a condition characterized by compulsive swearing, multiple muscle tics, and loud vocal noises. This disorder usually appeared in children between 7 and 10 years of age, and males were more often affected than females. Tourette suggested that this condition was inherited, because it seemed to "run in families."

In 1959, L. Eisenberg and his colleagues found that when a child with Tourette's Syndrome was studied, other family members were often found with the same problem. Summaries of large numbers of patients with Tourette's Syndrome showed that one-third had a family history of the disorder.

In 1980, Dr. Arthur Shapiro, a psychiatrist at Mt. Sinai Hospital in New York, studied pairs of identical twins in which at least one of the twins had Tourette's Syndrome. In the pairs studied, 7 pairs had the disorder—78%.

This work was followed up by David E. Comings and his colleagues who carried out a series of studies at the City of Hope Medical Center in Duarte, Calif. In 1984, 246 families were examined in which individual family members had Tourette's Syndrome at different grades of severity. In 65% of the cases there was a clear genetic linkage.

Observing that stress worsens the symptoms of Tourette's Syndrome, Comings suggested in his book "Tourette's Syndrome and Human Behavior" that genetic anomalies in the reward system in the brain—in particular the dopaminergic system—may be responsible for predisposition to and onset of the disorder.

In 1991, following publication of Blum and Noble's work on the A1 allele of the Dopamine $D_2$ receptor gene, Comings and his colleagues reported that 44.9% of individuals diagnosed with Tourette's carried the allele. The prevalence of the A1 allele increased with the severity of the cases.

Comings now sees that "Tourette's Syndrome is a complex, neuropsychiatric spectrum disorder that includes ADHD, obsessive, compulsive behaviors, conduct disorder, and other related disorders. Tourette's is a severe form of ADHD, and may have the same genetic origin."

Early speculation about the non-genetic causes of ADHD focused on such problems as marital disorder, poor parenting, brain damage, or psychiatric illness or alcoholism or drug abuse in the family. To these causes were added behaviors such as conduct disorder and anti-social personality. Later, these behaviors were shown to be linked genetically to drug and alcohol abuse. Most recently, research has begun to show a significant association between these behavioral disorders, ADHD, and genetic anomalies.

a. Attention Deficit-Hyperactivity Disorder

A body of evidence now exists which supports the role of genetics in ADHD. This evidence includes:

1. A number of studies have shown that fathers and/or mothers of ADHD children tend to have antisocial personality and alcoholism. In 1971, for example, James Morrison and Mark Stewart examined parents of 59 hyperactive children and 41 control children. In 21 of the families, at least one parent was alcoholic or had antisocial personality and other related behaviors. By contrast, only four of the control families were so affected.

In a family study of parents and siblings of felons, there was an increased frequency of anti-social personality, alcoholism, and drug addiction in male relatives of hyperactive children.

2. Numerous studies indicate that 20% to 30% of siblings of children with ADHD also have ADHD. This is two to seven times the frequency found in children used for controls. These siblings were five times more likely to have major depression than control children.

Other studies showed that 22% of brothers and 8% of sisters of hyperactive children were hyperactive themselves. However, when Attention Deficit is considered without hyperactivity, the number of brothers and sisters affected were the same.

David Comings suggests that this could explain the reason why clinically boys are more likely to have Attention Deficit with hyperactivity, while girls have Attention Deficit without hyperactivity.

3. In a study of ADHD children it was found that if neither parent had the syndrome, 11% of the siblings had ADHD. If one parent had ADHD, 34% of the siblings had ADHD.

The observed fact that ADHD parents have an ADHD child does not prove that the problem is genetic. The question can be asked, Was the behavior learned? One answer to the question is to look at siblings and half-siblings, both raised in the same environment. If ADHD is learned, the frequency should be the same for both. In actuality, half-siblings who have only half the genetic similarity show a significantly decreased frequency of ADHD.

In one study of twins, if one identical twin had ADHD, the other also had ADHD. If non-identical twins had ADHD, only 17% of the other twins had ADHD. This finding was confirmed in two other independent studies.

Another approach is to look at the parents of ADHD children given up for adoption. If ADHD is a genetic disorder, the parents of children with the problem should show a higher frequency of ADHD, antisocial personality, or alcoholism than the adopting parents. In a study of ADHD children of ADHD parents who gave up their children at birth for adoption, it was found that the rate of antisocial personality, alcoholism, and ADHD was higher in the biological parents than in the adopting parents.

Similar to his study on Tourette's syndrome, Comings' study of ADHD identified a number of children with the disorder and found that the A1 allele of the dopamine $D_2$ receptor gene was present in 49% of the sample compared to only 27% of the controls. In studying children of parents with severe alcoholism, Blum and associates found a similar association with the A1 allele in 55% in the cases studied, compared to 22% of the controls.

The number of people who suffer from one or more forms of RDS is staggering: in the United States alone, there are 18 million alcoholics, 28 million children of alcoholics, 6 million cocaine addicts, 14.9 million who abuse other substances, 25 million addicted to nicotine, 8, million people who are obese, 3.39 million school age children with attention deficit disorder (ADD); 625,000 with Tourette's Syndrome; and 448,000 who have the problem of compulsive gambling.

b. Alcoholism

It is known that P3 abnormalities have predictive value in children of alcoholics with regard to substance abuse vulnerability or prolonged P3 associated with the DRD2 A1 allele in children of active alcoholic fathers. A prolonged P3 latency in mixed (with or without polysubstance abuse) neuropsychiatrically-ill patients is reported with the $D_2$ dopamine receptor A1 allele. Previously it has not been known whether P3 latency was significantly longer in homozygote A1 carriers compared to homozygote A2 carriers.

Noble et al. (1994) recently observed children of active alcoholics to have prolonged P3 latency and this deficit was strongly associated with the A1 allele of the $D_2$ dopamine receptor gene. Support of their findings is derived from the work of Howard and Polich (1985) and Courcheene et al. (1975) who found decreasing P3 latency in children during maturation, whereas increased latency has been observed with advanced age, suggesting age-related ERP changes. This latter finding coupled with reports of reduced $B_{max}$ of the $D_2$ dopamine receptors with advanced age provides a possible mechanism for heritability of prolonged P3 latency in children with the $D_2$ dopamine receptor A1 allele (Morelli et al., 1990).

While a number of studies demonstrated P3 changes in alcohol and drug dependent subjects, two recent studies found an association of P3 latency in children of active alcoholic fathers with the A1 allele of the DRD2 gene, which also correlates with the presence of parental history of obesity post-puberty onset of obesity, as well as carbohydrate preference (Rajput-Williams et al., 1988), and in a psychiatric population having two copies of the A1 allele of the DRD2 gene as will obese patients with two or more copies of the A1 allele (Blum et al., 1994a, 1994b). Surprisingly, no electrophysiological data to date has implicated P3 abnormalities in a subtype of obesity.

Many studies on the P3 have treated alcoholism as if it were a single discrete entity. However, Jellinek (1960) has emphasized the distinction between alcoholics who had persistent alcohol-seeking behaviors (i.e. "inability to abstain entirely") and others who could abstain from alcohol for prolonged periods. If P3 characteristics vary in these two types of alcoholics, then it is possible that the divergent P3 findings in alcoholics and their children found in the literature may, in part, be related to the various admixtures of type 1 and 2 alcoholics studied.

c. Cocaine Addiction

In a recent paper on genetic animals models of alcohol and drug abuse, clear evidence was found that several response to alcohol (sensitivity to ataxia, tolerance to hypothermic and ataxia effects, preference drinking, and conditioned place preference) indicate the effects of QTLs influence all these phenotypes in the middle portion of chromosome 9 (Crabbe et al., 1994). In fact, four of the five traits showed their highest association with the same marker, Cyp1a 1, at 9:31. This strongly suggests, but does not prove, that a single locus accounts for all these associations. Consumption of methamphetamine (in saccharin), methamphetamine-stimulated activity, and haloperidol-induced Straub tail maps nearby.

Moreover, the ethanol preference and haloperidol catalepsy associations with markers near DRD2 have been verified in F2 mice with PCR™ genotyping. In summary, the potential interest of this synthetic approach is a cluster of four ethanol, one morphine, and one cocaine response mapping to chromosome 9. Finally, the authors point out that in the mouse, chromosome 9 maps to the DRD2 gene and suggests that interest in this region therefore is due to the interest of the gene coding for the dopamine $D_2$ receptor. It is believed that these findings in the animal model support the proposal that variants of the $D_2$ dopamine receptor gene are important common genetic determinants in predicting addictive behaviors.

It is important to note that while it is difficult to calculate it is true a number of these impulsive-addictive-compulsive behaviors overlap and therefore the prevalence numbers may be inflated. However, it is also equally true that to date there is no sufficient data on adequately assessed controls since comorbid behaviors related to RDS have not been well characterized and therefore this would obscure true specificity as well as sensitive numbers. Nevertheless, according to preliminary analyses, the DRD2 gene screening test would have predictive value.

d. Compulsive Overeating and Obesity

Obesity is a heterogeneous and prevalent disorder having both inheritable and environmental components once considered to be essentially determined by environmental factors (Stunkard et al., 1986). In the Danish adoption study, the weight of adult adoptees was strongly related to the body mass index (BMI) of the biological parents and to the BMI of their adoptive parents (Stunkard et al., 1990). Other twin and adoption studies are also pointing to heredity as an important contributor to the development of obesity while childhood environment has little or no influence (Laskarzenslci et al., 1983; Macdonald and Stunkard, 1990; Zonta et al., 1987). Moreover, the topographical distribution of fat has also been found to have inheritable elements (Bouchard et al., 1988). In studies of families and Mz twins, researchers (Bouchard et al., 1990) found internal fat to be influenced more by heredity than is the amount of subcutaneous fat.

Recently, it has been suggested that in obesity there is evidence for both polygenic and major gene inheritance in the mode of transmission, therefore suggesting molecular genetic representation (Price et al., 1990).

Given the complex array of metabolic systems that contribute to obesity, it is not surprising that several have already been implicated in disorders linked to compulsive overeating, including the DRD2 variants.

The relationship between macroselection of various foods and familial polysubstance abuse has been documented throughout the literature. Neurochemical studies have supported the commonality of reinforcement through dopaminergic systems by alcohol, cocaine, and carbohydrates.

If a diathesis toward obesity is in part determined by heredity, then it should have a molecular genetic representation. Given the complex array of metabolic systems that contribute to obesity, it would not be unexpected that several genes will be implicated in this disorder. Indeed, already, polymorphisms in the genes for apolipoprotein-B (Rajput-Williams et al., 1988), apolipoprotein-E (Fumeron et al., 1988; Pouloit et al., 1990), low density lipoprotein (LDL) receptor (Zee et al., 1992), glucocorticoid receptor (Weaver et al., 1991a), and insulin (Weaver et al., 1991b) have been associated with obesity.

Food, like a variety of reinforcing substances such as alcohol and other drugs of abuse, when consumed can produce euphoria or pleasure. Although the precise localization and specificity of the reinforcing properties of these substances are under debate, there is general accord that they are manifested in the dopaminergic reward pathways of the brain (For reviews see Hoebel, 1985; Koob, 1992; Wise and Rompre, 1989). Evidence that the dopaminergic system may be implicated in obesity is suggested from studies showing the effectiveness of amphetamine-like drugs in weight loss (Scoville, 1975). However, the abuse potential of these drugs has limited their use.

Furthermore, neuroleptics, which block DRD2, have been shown to lead to body weight gain in clinical (Caffey, 1961; Doss, 1979) and animal studies (Baptist et al., 1987). In view of observations suggesting that obesity is in part determined by heredity and because the dopaminergic system may be involved in eating behavior, the question raised herein is whether a dopamine receptor gene is implicated in some forms of obesity. In the present report, the prevalence of TaqI A DRD2 alleles was determined in obese subjects. Moreover, the relationships of these alleles to anthropomorphic and metabolic parameters as well as to parental history and onset of obesity and food preference were ascertained.

While a complex array of metabolic systems contribute to obesity among individuals, it is surprising that a variety of polymorphisms of DRD2 have been found to be associated with not only obesity, but also a number of other addictive behaviors including alcoholism, cocaine dependency, and carbohydrate bingeing. (Blum et al., 1990; Comings et al., 1990b; Noble et al., 1993a). Indeed several genes have already been implicated in this disorder (Rajput-Williams et al., 1998; Weaver et al., 1991a, 1991b; Poulot et al., 1990).

e. Pathological Gambling

Pathological or compulsive gambling has been termed "the pure addiction" since it is not associated with the intake of drugs (Rosenthal, 1992). Both the DSM-III-R and DSM-IV criteria draw upon many similarities with psychoactive substance abuse including a preoccupation with gambling, development of tolerance with a need to gamble progressively larger amounts of money, withdrawal symptoms, and continued gambling despite the severe negative effects on family and occupation (Rosenthal, 1992). Because of its relevance to the question of the role of the DRD2 gene in addictive behaviors, Comings and co-workers initiated a study of pathological gamblers. Of 171 non-Hispanic Caucasian subjects meeting the DSM-IV criteria for pathological gambling, 50.9% carried the $D_2$ A1 allele ($\chi^2$ versus non-substance abusing controls=41.96, df=1, p<0.00000001). To evaluate severity, the subjects were asked 15 questions relating to severity and number of DSM-IV criteria met. Of those in the lower half of severity, 40.9% carried the $D_2$ A1 allele. Of those in the upper half, 63.8% carried the $D_2$ A1 allele. For males, the comparable figures were 42.9% and 67.4%. The Mantel-Haenszel ($\chi^2$ for a progressive trend (controls→less severe→more severe) for the total group, and males only, was 41.26 and 35.09 respectively, p<0.00000001. Of the males without alcohol abuse or dependence, 49.1% carried the $D_2$ A1 allele. Of the males with alcohol abuse or dependence 76.2% carried the $D_2$ A1 allele (Mantel-Haenszel $\chi^2$=33.4, p<0.00000001). Despite this strong association of the prevalence of the $D_2$ A1 allele with alcoholism, substance abuse did not explain the association with pathological gambling. A logistic regression analysis showed that the presence or absence of the $D_2$ A1 allele showed a greater correlation with the severity of pathological gambling than any of 12 other variables including age of onset, sex, substance abuse, depression, and childhood conduct disorder. These studies indicate that the $D_2$ A1 allele plays a major role as a risk factor in a pure addictive behavior such as pathological gambling.

f. Tobacco Abuse, Nicotine Addiction, and Smoking

While environmental factors may be important determinants of cigarette and other nicotine-containing product use, results from adoption, association, family, trait marker and twin studies indicate that acquisition and maintenance of tobacco abuse are also influenced by heredity (Hughes, 1986). Of particular relevance are studies of twins which show that concordance rates for smoking are consistently higher in MZ than DZ twins (Mangan and Golding, 1984; Heller, et al., 1988; Hannah, et al., 1985). Although increases in concordance rates for MZ twins are quite reliable, other factors, such as interactions between twinning conditions and personality in MZ and DZ twins, may account for some of the differences in concordance rate. In order to examine this issue, adjustments were made for shared variance in a recent analysis of MZ and DZ twins (Swan, et al., 1990). Before and after adjustments for covariates, heritability for tobacco abuse and smoking was unchanged and remained highly significant, accounting for 52% of the variance.

The present invention describes the correlation between smoking behavior and a genetic factor: the DRD2 gene. Rat complementary DNA (cDNA) of the DRD2 gene has been cloned and expressed (Bunzow, et al. 1988). Rat cDNA was use to clone a human genomic fragment and mapped the DRD2 gene to the q22–q23 region of chromosome 11 (Grandy, et al., 1989b). Moreover, they identified two alleles in TaqI digests of human DNAs: A1, a less frequent allele, and A2, a more frequent allele. The role of this dopaminergic system was examined in current smokers, past smokers and nonsmokers by their association with the DRD2 alleles.

g. Polysubstance Abuse

The present invention clearly demonstrates the surprising finding that DRD2 gene variants are not only specific for individual RDS behaviors such as alcoholism, compulsive overeating, or tobacco abuse per se but also prevail in polysubstance abuse as well. This result has been confirmed by Smith et al. (1992), when they reported results similar to those presented herein by the inventors which showed association of the TaqI A1 and B1 alleles of the DRD2 receptor gene with not only severe alcoholism (Blum et al., 1993), but also heavy polysubstance users, and subjects with DSM-III-R. Subjects having diagnoses of psychoactive substance use displayed significantly higher TaqI A1 and TaqI B1 frequencies than control subjects. These authors confirmed the work of the present invention by reporting a role for a DRD2 gene variant marked by these RFLPs in enhanced substance abuse vulnerability (Smith et al., 1992).

In similar fashion, the work of other authors has confirmed the present findings. For example, Comings et al., (1991) reported an association between A1 allele of the DRD2 gene and a number of neuropsychiatric disorders, including polysubstance abuse. The prevalence of the $D_2$ A1 allele in patients with drug addiction compared to controls known not to be alcoholic yielded a significant difference (p=0.005) (Comings et al., 1991).

Likewise, in other work by Comings et al. (1994a) 200 subjects on an addiction treatment unit were divided according to diagnosis. Of the 19 with alcohol abuse, only 21% carried the $D_2$ A1 allele. Of 75 with alcohol dependence (severity not characterized), 32% carried the $D_2$ A1 allele. Neither of these was significantly different from controls, and the prevalence in those with alcohol abuse was lower than in the controls. By contrast, of 104 subjects with drug and alcohol dependence 42.3% carried the $D_2$ A1 allele. This was significantly higher than in the 29% in 763 controls consisting of screened and unscreened subjects ($\chi^2$=7.68, df=1, p=0.0056). In this study logistic regression analysis revealed a highly significant association between multiple substance abuse, based on money spent on drugs, and the presence of the $D_2$ A1 allele p=0.0003, and age of onset of drug abuse (p<0.001). $D_2$ A1 carriers exceeded $D_2$ A2A2 subjects for a history of being expelled from school for fighting (p=0.001), and of those ever jailed for violent crimes, 53.1% carried the $D_2$ A1 allele versus 28.8% of those jailed for non-violent crimes (p=0.011). This increased to 69.2% for those who were both jailed for violent crime and expelled from school. They concluded that possession of the $D_2$ A1 allele is significantly associated with the severity of polysubstance abuse and some aggressive behaviors.

The A1 allele contributed to 16.7% in the 0-risk score group, 35.0% in the 1-risk score group, 66.7% in the 1-risk group and 87.5% in the 3-risk score group. Risk score differences with allelic classification yielded a Pearson $\chi^2=10.9$, df=3, with a p=0.012. Verification of the association of the number of risk factors with the allelic classification was made using a Chi-square test for linear trend. Increasing risk scores are positively and significantly related to A1 classification with $\chi^2=10.5$, df=1, p=0.001. The results indicate that the minor alleles A1 and B1 of the DRD2 gene are strongly associated with cocaine dependence in the samples studied. The polymorphic pattern of this dopamine receptor gene suggests that a gene conferring susceptibility to cocaine dependence is located on the q22–q23 region of chromosome 11.

4. Dopamine $D_2$ Receptor Densities and DRD2 Alleles

Dopamine $D_2$ receptors densities are lower in brain tissue obtained from patients carrying the A1, B1, and $DRD2^{In6-Ex7}$ haplotype I alleles of the DRD2 gene (Flanagan et al., 1992; Noble et al., 1991; Blum et al., 1994). Similar reduced DRD2 densities have also been found in alcohol preferring rodents compared to alcohol-non-preferring inbred animals (Mcbride et al., 1993; Stefanini, 1992; Boehme et al., 1981). Moreover, $D_2$ receptor agonists significantly reduce alcohol intake in high alcohol preferring rats, whereas $D_2$ receptor antagonists increase alcohol intake in these inbred rodents (Dyr et al., 1993).

5. The Polygenic Nature of IACDs

Researchers agree that vulnerability to drug and alcohol seeking behavior or IACD is likely to be the result of multiple factors and is polygenic in nature, of which the DRD2 genotype is one key factor (Pickens et al., 1991; Pato et al., 1993; Conneally, 1991; Cloninger, 1991). In order to further shed light on this subject, Bayes' Theorem was utilized as a mathematical model to assist in evaluating the predictive value of the A1 allele of the DRD2 gene in compulsive disorder (Rosner, 1986). The results of these analyses have been summarized in Tables 1–3.

TABLE 1

POSITIVE ASSOCIATIONS OF VARIANTS OF THE DOPAMINE $D_2$ RECEPTOR GENE IN "REWARD DEFICIENCY SYNDROME"

| INVESTIGATOR(S) | POLYMORPHIC LOCI | TYPE OF STUDY | PARAMETER TESTED | POPULATION STUDIED |
|---|---|---|---|---|
| Blum et al. | A1 | Association | Alcoholism | Deceased Non-Alcoholics/Severe Alcoholics |
| Blum et al. | A1 | Association | Severity | Living Non-Alcoholics Less/Severe Alcoholics |
| Blum et al. | B1 | Association | Severity | Living Non-Alcoholics Less/Severe Alcoholics |
| Noble et al. | A1 | Association | Severity and Medical Complications | Hospitalized Living Non-Alcoholics Less/Severe Alcoholics |
| Noble et al. | A1 | Association | Dopamine $D_2$ Receptor Density | Deceased Non-Alcoholics/Severe Alcoholics |
| Noble et al. | A1/B1 | Association | Cocaine Abuse and Behavioral Risks | Living Cocaine Abusers and Behavioral Risks Factors |
| Parsian et al. | A1 | Association | Alcoholism and Severity | Living Non-Alcoholics and Subcategorized Alcoholics |
| Comings et al. | A1 | Association | Polysubstance Abusers and Alcoholism | Living Non-Alcoholics/Alcoholics and Drug Abusers |
| Smith et al. | A1/B1 | Association | Severe Polysubstance Abusers | Living Non-Polysubstance Abusers and Polysubstance Abusers |
| Arinami et al. | A1 | Association | Alcohol Severity in a Homogenous Population | Living Japanese Non-Characterized Controls/Sub-Characterized Alcoholics |
| Flanagan et al. | $DRD2^{In6-Ex7}$ | Association | Dopamine $D_2$ Receptor Density | Deceased Non-Alcoholics/Severe Alcoholics |
| Blum et al. | B Alleles of the DRD2 Gene and DRD1 Alleles | Association | Dopamine D1 and $D_2$ Receptor Density and Alcohol Severity | Deceased Non-Alcoholics/Severe Alcoholics |
| Blum et al. | A1 | Association | Children of Alcoholics | Children of Alcoholics with at Least One Biological Parent Severe Alcoholic |
| Comings et al. | A1 | Association | ADDH | Characterized Non- |

TABLE 1-continued
POSITIVE ASSOCIATIONS OF VARIANTS OF THE DOPAMINE $D_2$ RECEPTOR GENE IN "REWARD DEFICIENCY SYNDROME"

| INVESTIGATOR(S) | POLYMORPHIC LOCI | TYPE OF STUDY | PARAMETER TESTED | POPULATION STUDIED |
|---|---|---|---|---|
| | | | | Attention Deficit-Hyperactivity (ADDH) Controls/Characterized ADDH Subjects |
| Comings et al. | A1 | Association | Tourett's | Characterized Tourett's Subjects/Characterized Controls |
| Comings et al. | A1 | Association | PTSD | Characterized Post-Traumatic (PTSD) Stress Disorder/Characterized Controls |
| Devors | A1 | Association | Severe Tourette's | Characterized Tourett's Subjects/Characterized Controls |
| Flanagan et al. | DRD2$^{In6-Ex7}$ | Association | Polysubstance Abuse Without Alcoholism | Characterized Non-Substance Abuser/Polysubstance Abusers |
| Arinami et al. | B1 | Association | Alcohol Severity in a Homogenous Population | Living Japanese Characterized Controls/Sub-Characterized Alcoholics |
| Amadeo et al. | A1 | Association | Alcoholism in a Homogenous Population | Living French Alcoholics Hospitalized and Non-Alcoholics |
| Comings et al. | A1 | Association | Polysubstance Abuse and Associated Behaviors | Polysubstance Abusers Including Alcoholics/Non-Substance Abusers |
| O'Hara et al. | A1/B1 | Association | Comparative Association Studies in White and Black Polysubstance Abusers | Living White and Black Polysubstance Abusers and Non-Substance Controls |
| Cook et al. | A1 | Affected-Sib Pair Linkage | Varying Degrees of Alcoholism | Three Groups of Affected Sib-Pairs Including Heavy Alcohol Abusers, Alcoholism and Severe Dependent Alcoholics |
| Suarez et al. | DRD2 A Alleles and C Alleles- Including Other Polymorphic Markers | Association and Linkage | Alcoholism | Unclassified Alcoholics and Non-Alcoholic Controls |
| George et al. | A Alleles of DRD2 and Alleles of DRD4 | Association | Alcoholism and Nicotine Abuse | Severe Alcoholism with Mixed Nicotine Abuse |
| Neiswanger et al. | A1 | Association | Alcoholism | Living Well Characterized Non-Alcoholic Controls and Unclassified Alcoholics |
| Noble et al. | A1 | Association | P-300 Amplitude and Latency | Well Characterized Children of Alcoholics with P-300 Latency Deficits and Their Fathers (Non-Alcoholics and Active Alcoholics) |
| Blum et al. | A1 | Association | P-300 Latency Amplitude and Latency | Well Characterized Neuropsychiatric Population With or Without Co-Morbid Polysubstance Abuse and Well Characterized Controls |
| Comings et al. | DRD2$^{In6-Ex7}$ Haplotypes | Association | Obesity | Overweight Subjects and Controls Subcategorizing by BMI |
| Noble et al. | A1 | Association | Obesity/Carbohydrate Bingeing | Characterized Overweight Obese Patients and Non- |

TABLE 1-continued

POSITIVE ASSOCIATIONS OF VARIANTS OF THE DOPAMINE $D_2$ RECEPTOR GENE IN "REWARD DEFICIENCY SYNDROME"

| INVESTIGATOR(S) | POLYMORPHIC LOCI | TYPE OF STUDY | PARAMETER TESTED | POPULATION STUDIED |
|---|---|---|---|---|
| Parsian et al. | C1/C2$^{In2-Ex3}$ | Association | Alcoholism | Obese Controls and Associated Risk Factors Alcoholics and Non-Alcoholic Controls |
| Noble | A1 | Association | Smoking | Characterized Severe Smokers |
| Blum | A1 | Association | Obesity | Characterized Overweight Obese patients with or without Co-Morbid Chemical Dependency |
| Comings | A1 | Association | Pathological Gambling | Well-Characterized Severe Pathological Gambling |
| Comings | A1 | Association | Smoking | Severe Smokers and Non-Smokers |
| Comings | A1 | Association | Post-Traumatic Stress Disorder (PTSD) | Well-Characterized PTSD Probands and Non-PTSD Controls |
| Crabbe and Belkap | Chromosome 9 (in mouse) | Quantitative Trait CDC1 (QTL) | Association with Number of Behavioral Responses | Variants on Chromosome 9 (DRD2) Associate with Four Ethanol Related Behaviors, One Morphine and one Cocaine Responses |
| Giejer et al. | A1 and B1 | Association | Scandinavian Alcoholism (Severe) | Positive Association with Severe Alcoholism but Not Less Severe Alcoholism |
| Hietala et al. | A1 | Association | Alcoholism | Positive Association Between Finnish Alcoholics and Non-Alcoholics |
| Christian et al. | A1 | Association | Adult Caucasian Twins | Association of A1 with a Number of Electrophysiological Parameters (delta band, N1 and P300 Deficits |
| Johnson et al. | A1 | Association | Substance Abusers | Association of A1 or P300 Deficits in Substance Abusers |

TABLE 2

THE DOPAMINE $D_2$ RECEPTOR GENE AS A PREDICTOR OF COMPULSIVE DISORDER UTILIZING BAYES' THEOREM

| RISK BEHAVIOR[1] | BAYES' THEOREM (F) | PREDICTIVE VALUE (%) |
|---|---|---|
| Alcoholism (Severe)[2] | 0.1433 | 14.3 |
| Cocaine Dependence (Severe)[3] | 0.1235 | 12.3 |
| Polysubstance Abuse[4] | 0.1218 | 12.8 |
| Chemical Dependency[5] | 0.2836 | 28.3 |
| Overeating (Severe)[6] | 0.1860 | 18.6 |
| Ingestive Behavior[7] | 0.3500 | 35.0 |
| ADHD[8] | 0.1602 | 16.0 |
| Smoking[9] | 0.415 | 41.5 |
| Pathological Gambling[10] | 0.046 | 4.6 |
| Tourette's Syndrome[11] | 0.055 | 5.5 |
| Total Addictive Behavior | 0.744 | 74.4 |

1. To calculate Bayes' theorem the following formula was utilized:

$$\text{predictive value} = \frac{(\text{prevalence})(\text{sensitivity})}{(\text{prevalence})(\text{sensitivity}) (1-\text{prevalence})(1-\text{specificity})}$$

To calculate the specificity, very well-characterized accessed controls screened for alcohol, drug and tobacco use were utilized (in some samples).

a) Alcoholism-prevalence-0.055, sensitivity=0.5632, specificity =0.804 b) Cocaine-prevalence=0.0285, sensitivity=0.8750, specificity =0.804 c) Polysubstance Abuse-prevalence =0.06, sensitivity= 0.4260, specificity =0.804 d) Food-prevalence=0.04, sensitivity =0.8460, specificity =0.804 e) ADHD-prevalence=0.075, sensitivity=0.4615, specificity =0.804 f) Smoking-prevalence=0.25, sensitivity =0.419 g) Pathological Gambling-prevalence=0.0185, sensitivity=0.0508 h) Tourette's Syndrome-prevalence=0.025, sensitivity=0.448

Impulsive-Addictive-Compulsive Behaviors-prevalence=0.552, sensitivity 0.462

2. To calculate the sensitivity of severe alcoholism proband genotyping was utilized from the following studies where the proband was characterized for chronicity or severity of the disorder: Blum et al. 1992; Blum et al., 1993; Bolos et al., 1990; Parsian et al., 1992; Gelernter et al., 1993; Noble et al., 1993; Amadeo et al., 1993.

3. To calculate the sensitivity of severe cocaine dependence Noble et al., 1993(probands with 3 risk factors) was utilized.

4. To calculate the sensitivity to polysubstance abuse a number of studies were utilized (Smith et al., 1992; Noble et al., 1993; Comings et al., 1993; and Gelernter et al., 1994 (unpublished), reviewed by Uhl et al., 1994.

5. Chemical dependency is the combination of alcoholism, cocaine dependence and polysubstance abuser probands.

6. To calculate the sensitivity of severe overeating Noble et al., 1993(probands with 3 risk factors) was utilized.

7. Ingestive behavior is the combination of alcoholism, cocaine dependence, polysubstance abuse and overeating probands.

8. To calculate the sensitivity of ADHD, the method of Comings et al., 1994 was utilized.

9. To calculate the sensitivity of smokers, the method of Comings et al., 1994 was utilized.

10. To calculate the sensitivity of pathological gambling, the method of Comings et al., 1994 was utilized.

11. To calculate the sensitivity of Tourette's Syndrome, the method of Comings et al., 1991 was utilized.

To calculate the sensitivity of Impulsive-Addictive-Compulsive Behavior, a composite of all available data was utilized.

To calculate prevalence the following assumptions were made:

a) Severe alcoholics in the U.S. population constitute an estimated 11 million out of 200 million adults.

b) Severe cocaine addicts in the U.S. population constitute an estimated 5.7 million out of 200 million adults.

c) Morbidly obese food addicts in the U.S. population constitute 8 million out of 200 million adults.

d) Polysubstance abusers in the U.S. population constitute an estimated 14.9 million out of 200 million adults.

e) Attention-deficit hyperactivity disorder (ADHD) in the U.S. population constitute an estimated 7.5% of 45,250,000 school age children between the age of 6 and 17 or 3.39 million out of 249 million people.

f) The prevalence of smoking the US population has been estimated at 25% or 62 million.

g) The prevalence of pathological gambling in the US population is approximately 1.8%.

h) The prevalence of severe Tourette's Syndrome in the US population is 1 out of 40 or 2.5%.

i) The prevalence of total impulsive-Addictive-Compulsive Behavior is 55.2%. This estimate may vary as a function of overlap among these spectrum disorders.

TABLE 3

SUMMARY OF DOPAMINE $D_2$ RECEPTOR GENE VARIANTS IN IMPULSIVE-ADDICTIVE-COMPULSIVE BEHAVIORS

| Substance Abuse | Allele | | % Prevalence Disordered Controls | p Value | Ref |
|---|---|---|---|---|---|
| Alcoholism | D2 | A1 | 69  20 | .001 | 1 |
| Alcoholism (Less Severe) | D2 | A1 | 30  19 | NS | 2 |
| Alcoholism (Less Severe) | D2 | B1 | 17  13 | NS | 3 |
| Alcoholism[a] | D2 | C1 | 57  33 | .002 | 4 |
| Severe Alcoholism | D2 | A1 | 47  17 | .001 | 2 |
| Severe Alcoholism | D2 | B1 | 47  13 | .008 | 3 |
| Severe Alcoholism | $D_2^{In6-Ex7}$ Haplotype 1 | | 39  16 | .02 | 5 |
| Cocaine Dependence | D2 | A1 | 51  18 | .0001 | 6 |
| Cocaine Dependence | D2 | B1 | 39  13 | .01 | 6 |
| Polysubstance Abuse | D2 | A1 | 44  20 | 025 | 7 |
| Polysubstance Abuse | D2 | B1 | 33  28 | .001 | 7 |
| Smoking[b] | $D_2$ | A1 | 49  28 | $10^{-8}$ | 8 |
| Obesity Carbohydrate Bingeing | D2 | A1 | 46  19 | .003 | 9 |
| Obesity | D2 | A1 | 51  20 | .000019 | 10 |
| Obesity[c] | $D_2^{In6-Ex7}$ Haplotype 4 | | 88  55 | .0057 | 11 |
| ADHD | D2 | A1 | 46  25 | .0001 | 12 |
| Pathological Gambling | D2 | A1 | 51  28 | $10^{-8}$ | 13 |
| Tourette's Syndrome | D2 | A1 | 45  26 | .0001 | 14 |

[a]A1 allele denoted only with regard to homozygote genotype. Alcoholics (47/82); Controls (29/87), ($X^2 = 9.8$, df = 1, p = .002)
[b]D. E. Comings et al. (personal communication)
[c]Percentage of subjects in class 0 (normal weight-control) who carried the 4 haplotype was compared to class 4 (very high risk obese-disordered) who also carried the 4 haplotype
1. Blum, K., et al., 1990.
2. Blum, K., et al., 1991.
3. Blum, K., et al., 1993.
4. Suarez et al., 1994.
5. Flanagan et al., 1992.
6. Noble et al., 1993.
7. O'Hara et al., 1993.
8. Comings et al., 1994 (Personal communication);
9. Noble et al., 1994;
10. Blum et al., 1994.
11. Comings et al., 1993.
12. Comings et al., 1991.
13. Comings et al., 1994 (Personal communication);
14. Devor and Comings, 1992.

6. Heritability of the P300

Several studies have addressed the issue of heritability of the P3 in humans. MZ twins showed P3 latencies that were significantly more alike than those of unrelated matched control subjects (Surwillo, 1980; Polich and Burns, 1987). In another study comparing MZ and DZ twins (Rogers and Deary, 1991), the within-pair similarity of P3 latency was significantly greater in MZ than in DZ twins. However, in this same study, within-pair similarity of P3 amplitude was not significantly greater in MZ than in DZ twins. These findings support the view that P3 latency has an important genetic component.

7. P300 in Normative and Clinical Populations

It has been found that P3 latency decreases in children during maturation (Courchesne, 1984; Howard and Polich, 1985), whereas increased latency of this endogenous component has been observed in the aged P300 (Goodin et al., 1978; Brown et al., 1983; Picton et al., 1984), as well as in dementia (Goodin et al., 1979; Syndulko et al., 1982; Neshige et al., 1988), Parkinson disorder (Hansch et al., 1982; O'Donell et al., 1987; Stanzione et al., 1991), multiple sclerosis (Newton et al., 1989), and other organic brain dysfunctions (Papanicolaou et al., 1984; Morrow et al., 1992). P3 characteristics have also been studied in alcoholics and their children; however, the findings have not always been consistent. Thus, in alcoholics, increased latency (Pfefferbaum et al., 1979; Polich, 1984; Steinhauer et al., 1987), decreased amplitude (Porjesz and Begleiter, 1981; Ciesielski et al., 1985) of the P3, or both (Porjesz and Begleiter, 1985; Pfefferbaum et al., 1987) have been described. Similarly, children of alcoholics were reported to display increased latency (Schmidt and Neville, 1985; Steinhauer et al., 1987; Hill et al., 1988), decreased amplitude (Begleiter et al., 1984; O'Connor et al., 1986), increased latency and decreased amplitude (Elmasian et al., 1982; Whipple et al., 1988, 1991; Hill et al., 1990), or no changes in either of these two P3 measures (Polich and Bloom, 1987, 1988; Polich et al., 1988).

In one study, the A1 allele was present in 69% of deceased severe alcoholics (Blum et al., 1990) compared to 20% of controls. In another study, the gene frequency of the A1 allel of the DRD2 gene in unclassified alcoholics was 0.27 compared to a gene frequency in well-characterized non-alcoholic controls of 0.07. This later finding suggests a 3.85 fold risk in these probands (Neiswanger et al., 1993).

The overwhelming evidence supports an association of variants of the DRD2 gene with risk in developing IACD. Specifically, variants of the DRD2 gene have been correlated with increased risk of severe alcoholism (Blum et al., 1990; Blum et al. 1992; Parsian et al., 1991; Flanagan et al., 1992; Blum et al., 1991; Noble et al., 1994; Cook et al., 1993) crack/cocaine dependence (Noble et al., 1993; O'Hara, 1993; Comings, 1994) carbohydrate bingeing (Noble et al., 1994), obesity (Comings et al., 1993; Blum et al., 1994), ADHD (Comings, 1991), Tourette's syndrome (Devor et al., 1992), pathological gambling (Comings et al., 1994), and smoking (Noble et al., 1994; Comings et al.; George et al., 1993), among other compulsive behaviors.

The National Institute of Drug Abuse (NIDA) reported that the A1 and B1 alleles of the DRD2 gene accounts for 27% of the variance of drug dependence, independent of the environment and/or other gene defects (Uhl et al., 1993). Calculations based on data from twin studies indicate that genes may influence up to 60% of the vulnerability to severe substance abuse (Uhl et al., 1993). Taking these two findings together, the DRD2 variants could represent one of the most prominent single-gene determinants of susceptibility to severe substance abuse. However, other genes and the environment when combined, still may play the largest role.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

BRIEF DESCRIPTION OF THE EXAMPLES

1. Example 1 presents evidence describing a potential treatment for humans suffering from IACD using high-protein diet as a means of affecting P300 processing.

2. Example 2 describes the abnormalities observed in P300 latency in humans who are compulsive overeaters.

3. Example 3 presents evidence that polysubstance abuse also results in electrophysiological brain abnormalities.

4. Example 4 details the relationship between P300 latency and the $D_2$ dopamine receptor A1 allele in IACD subjects.

5. Example 5 describes the relationship between P300 latency and the $D_2$ dopamine receptor A1 allele in children having at least one parent who was an alcoholic.

6. Example 6 identifies the defect in DRD2 in human subjects who are compulsive overeaters.

7. Example 7 provides data showing increased prevalence of the DRD2 A1 allele in humans suffering from compulsive overeating and polysubstance abuse.

8. Example 8 details the relationship between occurrence of specific DRD2 alleles in persons who are addicted to cigarette smoking.

9. Example 9 describes the utility of the present invention in predicting Reward Deficiency Syndrome as a function of DRD2 receptor gene alleles using Bayes' Theorem.

EXAMPLE 1

ENKEPHALINASE-INHIBITION AND PRECURSOR AMINO ACID LOADING ENHANCES ATTENTION PROCESSING AT P300 IN HEALTHY HUMANS

A. METHODS

1. Subjects

This study involved 20 normal volunteer subjects free of psychological, neurological, or psychiatric conditions. Each subject performed the test battery twice as a test-retest paradigm, thus acting as his or her own control. Initial testing was done on day zero (pre-test) and then again after 28–30 days (retest). The subject consumed six Tropogen™ capsules daily for 28–30 days.

2. Performance Paradigms

Two performance paradigms were utilized as behavioral probes for the electrophysiological studies. The probes are:

a. Spatial Orientation

This is a reaction time-based task, championed by Posner et al., (Posner et al., 1988) where priming cues are presented in different portions of the visual field (Carenzie et al., 1980).

b. Contingent Continuous Performance (CCPT)

This task is a variant of Rosvold (Rosvold et al., 1956). This version of the task had a constant interstimulus interval (ISI) of 0.8 sec and comprises 500 trials. Three ERP's are constructed according to one of three conditions: distractor ERP's are constructed according to one of three conditions: distractor (any letter other than a 'T', warning signal (the first 'T' in a pair), and target (the second 'T' in a pair).

3. Electroencephalographic Analysis

The EEG was recorded from 28 active recording sites referenced to linked earlobes (A1-A2). The montage was based on the international 10–20 system, with additional electrodes placed in the fronto-temporal (FTC1, FTC2), centro-parietal (CP1, CP2), temporo-parietal (TCP1, TCP2), and parieto-occipital (PO1, PO2), temporo-parietal (TCP1, TCP2), and parieto-occipital (PO1, PO2) regions. Electrode impedances were kept at less than 5kΩ.

The EEG and EOG were amplified with a 32-channel NeuroScience Brain Imager (0.1–40 Hz, 6 dB/octave lowpass, 36 dB/octave highpass). The raw EEG was sampled for 2.56 seconds by 16-bit analogues-to-digital converters (TECMAR Labmaster DMA) under control of the SCAN EP/EEG acquisition and analysis system (NeuroScan, Inc.).

A total of 200 sweeps were recorded for the Spatial Orientation, and 500 sweeps were recorded for the Contingent Continuous Performance Test. There were three parameters examined, each of which may vary according to the efficiency of an individual's attentional processing. These parameters were: (1) latency, (2) amplitude, and (3) symmetry (spatial distribution) of components of the ERP's.

4. Statistical Analysis

In terms of data analysis, first T-test statistical maps were generated for all 28 electrode sites at each point in time. The $P_z$ was selected as the site for statistical analysis, and the peak latency past peak amplitude within a 275–325 msec interval was determined. The second stage of statistical analysis employed a paired T-test model, comparing the Baseline and Treatment conditions.

B. RESULTS

An overlay of the electrode array, with ERP's from the CCPT task superimposed for the 28 scalp recording sites revealed patterns for the right visual field which mirrored those of the left. There are no significant treatment effects associated with this N2 component [F(1,17)=2.30, p=0.0259]. Nevertheless, late vertex positivity (i.e., P300 component) in the retest condition was found to be larger in amplitude for both the right facilitated condition [F(1,17)= 16.31, p=0.0009]and for the left facilitated condition [F(1, 17)=8.53, p<0.005]. That is, the group average P300 component after Tropogen™ administration was found to be significantly enhanced when orienting to the right and left visual fields. The spatial distributions, as well as the amplitude changes of the P300 components, can be better appreciated in a topographical fashion for the right facilitated condition.

For the interval 300–400 msec, the topographical features of the component remain the same, although the peak amplitude was enhanced with Tropogen™ treatment. On the other hand, analysis of the reaction time data did not approach statistical significance. With respect to the CCPT, the average target waveforms at $P_z$ were determined and topographical maps were generated for the 300–400 msec interval for the target conditions before (Baseline) and after (Treatment) Tropogen™. While the topographical features of the P300 component were the same in both instances, the amplitude showed a significant enhancement when comparing the pre-test to the retest condition [F(1,16)=7.4, p=0.015]. That is, in both the Baseline and Treatment conditions, the P300 component occupied a posterior central distribution and was symmetric, but the amplitude of the P300 component was enhanced in the Treatment condition.

While electrophysiological changes were seen after approximately four weeks of treatment, there were no significant differences in any of the performance measures for either behavioral probe. While there were trends toward improvement with respect to reaction times, the changes were not statistically significant in the paired T-Test model. Perhaps this is due to the fact that the subjects were normals and near the ceiling with respect to processing speeds and consistency of performance. A more complex task may elucidate benefits in performance with increases in P3 amplitude even in normals.

EXAMPLE 2

P300 (P3) ABNORMALITIES IN COMPULSIVE OVEREATING

A. METHODS

1. Subjects

A total of 53 obese subjects (Table 4) were analyzed by a BEAM™ device (a registered trademark of Nicolet Corporation). For P3 control group, 15 of 800 patients were selected who were a) drug, alcohol, and food addiction free; b) without psychiatric disorder and/or a medical diagnosis not related to CNS; or c) staff volunteers.

TABLE 4

DEMOGRAPHIC CHARACTERISTICS OF CONTROLS AND AN OBESE POPULATION

| Group | No. | Mean Age[1] ± S.D. | Gender[2] Male (%) | Female (%) |
|---|---|---|---|---|
| Control | 15 | 51.1 ± 9.3 | 33 | 67 |
| Obese | 53 | 51.1 ± 13.4 | 21 | 79 |

[1]Student T-test, p = 1.0
[2]Pearson's $\underline{X}^2$, p = 0.31
[3]Student T-test, p = .001

2. Electroencephalographic Measurements

A 24 channel EEG recorder was utilized incorporating the standard 10/20 system of electrode placement, plus two earlobe and supraorbital electrodes. Digitized EEG was recorded in monopolar and bipolar montage for one hour. Digitized EEG and EP's were stored on optical disk of the BEAM™ Nicolet System. Although this study focuses on the P3 only, eye, EMG and EKG monitors were employed throughout the recording. Grass photic stimulation (model PS22C) and 0.5 Hz was performed. The tracing captured wakefulness and drowsiness.

3. P3 Analysis

P3 tests were accomplished by standard auditory oddball paradigm of burst tones. P300 was analyzed at $F_z$, $C_z$ and $P_z$, and max (maximum voltage regardless of electrodes most commonly $P_z$) for time and voltage (differential voltage).

4. Statistical Methods

A Chi-square linear trend analysis (Cochran, 1954) was used to test if increasing risk factors for obesity are associated with electrophysiological abnormalities.

B. RESULTS

Of the total of 53 patients who volunteered for the study, 21% were males and 79% were females. With regard to demographics, 29.5% had a parental history of chemical dependency, 20.5% were carbohydrate bingers, and 27.3% had comorbid drugs and/or alcohol dependence. The age (mean±SE) of the 53 obese individuals was 51.1±13.4 years. Of the total of 15 control patients, 33% were males and 67% were females. The age (mean±SE) of the 15 control subjects was 51.1±7.3 years.

Between these two groups, the age and sex were not significant, whereby p=1.0 and p=0.31, respectively. As seen in Table 5, the BMI of both males and females in the obese group was 34.6±8.2, and in the control group it was 22.3±3.0. The difference between these two groups was significant, whereby p=0.001.

Figure 3:
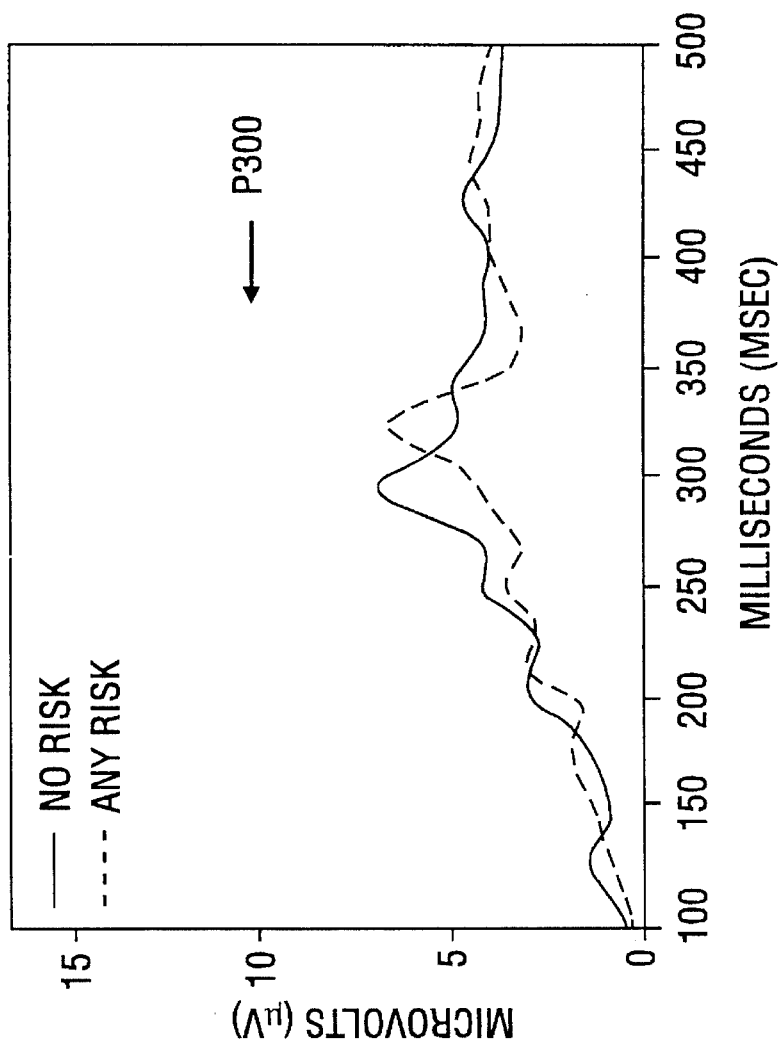
FIG. 3. P300 latency as a function of risk factors in obese patients. A shift is observed (i.e., a reduced P300 latency) in obese patients having at least one risk factor (e.g., parental history of alcoholism, carbohydrate bingeing, or comorbid chemical dependency) when compared to non-obese controls.
Figure 3:
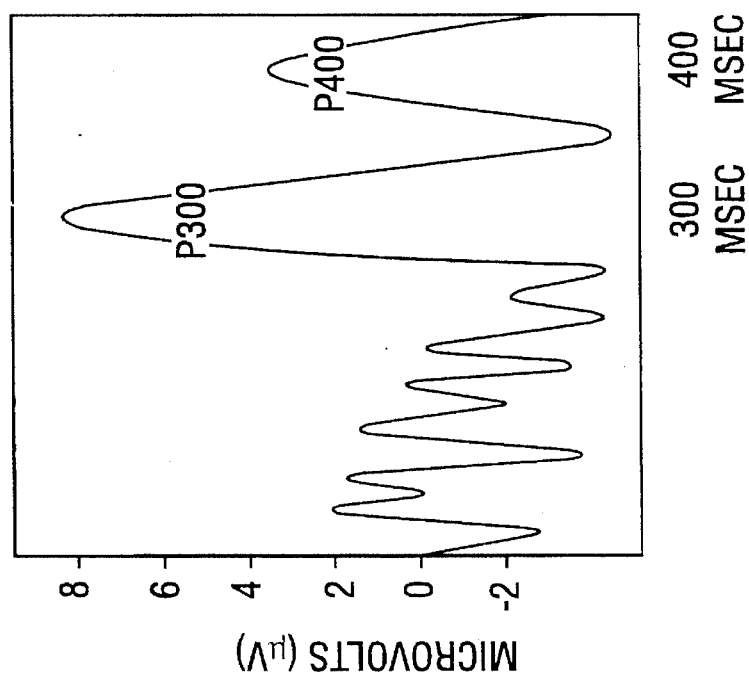

The P3 amplitude at average P3 time in obese and control subjects was 7.07±2.3 uV at 320±28.8 msec and 10.9±4.4 uV at 306±27.0 msec, respectively (Table 6). The P3 amplitude was significantly different (two-tailed, t=3.24, df=16.2, p=0.005), whereas P3 latency was not significant. Preliminarily, a significant correlation of prolongation of P3 latency was correlated with the three risk factors of parental substance abuse, chemical dependency, and carbohydrate bingeing (p<0.03) (FIG. 3). A decreased P3 amplitude correlated with family history of alcoholism and drug abuse (p<0.049).

Age, gender, and psychiatric diagnosis were matched. Generally, the mean age between all groups was assessed and did not significantly differ (p=0.756). The mean age of men (44.7±1.32) and the mean age of females (46.8±15.4) were not statistically different (p=0.835). For this investigation, in 16 controls, sexual selection included 63 percent females and 37 percent males; in 34 PNPS probands, 62 percent females and 38 percent males; and in 61 matched, PPS, 48 percent females and 52 percent males. Pearson $\chi^2$

TABLE 5

RISK FACTOR(S) CHARACTERISTICS OF CONTROLS AND AN OBESE POPULATION

| Group | No. | Mean Body Mass Index$^3$ ± S.D. | Parental Chemical Dependency (%) | Proband Chemical Dependency (%) | Proband Carbohydrate Bingeing (%) | Any Risk (Total) |
|---|---|---|---|---|---|---|
| Control | 15 | 22.3 ± 3.0 | 0 | 0 | 0 | 0 |
| Obese | 53 | 34.6 ± 8.2 | 29.5 | 27.3 | 20.5 | 55 |

$^1$Student T-test, p = 1.0
$^2$Pearson's $X^2$, p = 0.31
$^3$Student T-test, p = .001

TABLE 6

P300 AMPLITUDE AND LATENCY AT $V_{pz}$ IN DIAGNOSED OBESE AND CONTROL POPULATIONS UTILIZED IN THIS STUDY

| Group | Number | Mean Amplitude$^1$ (µV) ± S.D. | Mean Latency$^2$ (msec) ± S.D. |
|---|---|---|---|
| Control | 15 | 10.9 ± 4.4 | 306 ± 27.0 |
| Obese | 53 | 7.07 ± 2.3 | 320.4 ± 28.8 |

$^1$Standard T-test, p = .005
$^2$Standard T-test, p = .093

EXAMPLE 3

POLYSUBSTANCE ABUSE EXACERBATES BRAIN ELECTROPHYSIOLOGICAL DEFICITS IN A PSYCHIATRICALLY-ILL POPULATION

A. METHODS

1. Subjects

A total of 111 subjects (107 white, 2 Asian, and 2 black) were selected for study from approximately 5,000 visits from 800 patients to an outpatient private clinical practice in Princeton, N.J., in a one-year period. The subjects entered assessment through word of mouth, physician referral, and media announcements. These patients were highly motivated, since services provided by the clinic were costly, and each was informed that results and future treatment were dependent on a drug-free brain map. The demographic breakdown of the sample base is described in Table 7.

revealed a non-significant difference between groups in terms of gender (p=0.835).

In order to further characterize the severity of polysubstance abuse, 61 PPS subjects were subdivided into 19 least severe alcoholics (LSA), 23 most severe alcoholics (MSA), and 19 predominant cocaine abusing subjects (COKE).

2. Assessment Methods

The following selection criteria and assessment instruments were utilized: (1) DSM III-R Axis I diagnoses of a psychiatric disorder; (2) when necessary the Millon Clinical Multiaxial Inventory II was utilized to clarify the diagnosis; (3) clear predominance of one symptom type; (4) absence of neurological symptoms as identified by history, physical examination, a well as, in some cases, neurological examination at the time of the brain map study; (5) medication-free or drug-free at least 24 hours prior to the brain map; (6) Holmes Rahe Life Events Scale (Holmes and Rahe, 1967); (7) at least one initial psychiatric structured interview drawn from DSM III-R and a comprehensive psychiatric history, a modified Brief Psychiatric Rating Scale and a modified Hamilton Depression and Anxiety Scale, and a blind confirming follow-up evaluation by a board certified or eligible psychiatrist; (8) in select patients the Minnesota Multiphasic Personality Inventory-2 as well as Neuropsychological Assessment; (9) All subjects also filled out a Medical History and Brain Mapping Assessment Inventory; (10) follow-up consisted of one or more interviews within two to four weeks of initial entry into the study.

TABLE 7

DEMOGRAPHIC AND DIAGNOSTIC CHARACTERISTICS OF CONTROLS, PSYCHIATRICALLY ILL PATIENTS, AND CATEGORIZED POLYSUBSTANCE ABUSERS WITH EVIDENCE OF CO-MORBID PSYCHIATRIC PROBLEMS

| GROUP | NUMBER | AGE ± S.D.[1] | SEX[2] | | DYSTHYMIA[3] | GAD (%) | UNIPOLAR (%) | BIPOLAR (%) | ADD (%) | SCHIZOPHRENIA (%) |
|---|---|---|---|---|---|---|---|---|---|---|
| CONTROL | 16 | 48.9 ± 3.9 | 37.5 | 62.5 | 0 | 0 | 0 | 0 | 0 | 0 |
| PSYCHIATRIC PNPS | 34 | 45.5 ± 2.4 | 38.2 | 61.8 | 35.3 | 3.9 | 35.3 | 2.9 | 20.6 | 2.9 |

TABLE 7-continued

DEMOGRAPHIC AND DIAGNOSTIC CHARACTERISTICS OF CONTROLS, PSYCHIATRICALLY ILL PATIENTS, AND CATEGORIZED POLYSUBSTANCE ABUSERS WITH EVIDENCE OF CO-MORBID PSYCHIATRIC PROBLEMS

| GROUP | NUM-BER | AGE ± S.D.[1] | SEX[2] | | DYSTHYMIA[3] | GAD (%) | UNIPOLAR (%) | BIPOLAR (%) | ADD (%) | SCHIZOPHRENIA (%) |
|---|---|---|---|---|---|---|---|---|---|---|
| LSA (a) | 19 | 46.1 ± 3.2 | 47.4 | 52.6 | 52.7 | 5.3 | 10.5 | 0 | 21.1 | 10.5 |
| MSA (b) | 23 | 47.1 ± 2.8 | 52.2 | 47.8 | 43.5 | 0 | 17.4 | 0 | 34.8 | 4.3 |
| COKE (c) | 19 | 42.5 ± 3.9 | 42.1 | 57.9 | 26.3 | 0 | 26.3 | 21.1 | 21.1 | 5.3 |
| MSA + COKE | 42 | 45.0 ± 3.3 | 47.6 | 52.4 | 35.7 | 0 | 21.4 | 9.5 | 28.6 | 4.8 |
| PPS (d) | 61 | 45.3 ± 3.3 | 47.5 | 52.5 | 41.0 | 1.6 | 18.0 | 6.6 | 26.2 | 6.6 |

(a) LSA = Least Severe Alcoholic
(b) MSA = Most Severe Alcoholic Predominant
(c) COKE = Predominant Cocaine
(d) PPS = Psychiatrically ill Polysubstance Abusers consist of a, b, c
1. Analysis of variance p = .756
2. Pearson $X^2$ p = .835
3. All diagnosis match Pearson $X^2$ = .117; 3 major diagnoses (ADD, Unipolar Depression, Dysthymia) Pearson $X^2$ (p = .46).

All patients met the minimum DSM III-R criteria of at least one of six psychiatric diagnoses: dysthymia, generalized anxiety disorder (GAD), bipolar affective disorder, undifferentiated attention deficit disorder (ADD) (with or without hyperactivity), major unipolar depression, and schizophrenia (paranoid type) (Table 8).

All subjects and PPS subjects were assessed by similar instruments as described above, were free from significant lifetime substance abuse, and were matched for major psychiatric diagnoses and medically evaluated as free from neurological disorder.

To assess alcohol and drug abuse/dependency patterns, each patient received an extensive structured interview; a follow-up unstructured interview by a certified drug and alcohol counselor; and a conferring blind psychiatric review by a consulting board certified psychiatrist.

For 111 of the subjects, substance use was assessed according to the following: (1) DSM III-R lifetime psychoactive substance use disorder; (2) DSM III-R alcoholism; and (3) utilization of the alcohol and drug use history inventory—an 18-page questionnaire developed by Dr. Ernest Noble at the University of California-Los Angeles (UCLA). Validity of the UCLA questionnaire was further verified by SADQ analysis as observed in previous studies (Blum et al., 1990a; Blum et al., 1991a; Blum et al., 1990a, 1990b). This last instrument assessed family history of alcohol/drugs, frequency and quantity of peak psychoactive lifetime use, as well as clinical history of treatment. This quantity-frequency approach was chosen because of evidence that heavy use of alcohol may display significant heritability.

TABLE 8

SIGNIFICANT BEAM COMPARISONS IN CONTROLS VS MATCHED PSYCHIATRICALLY-ILL SUBJECTS LEAST SEVERE ALCOHOLICS, MOST SEVERE ALCOHOLIC AND PREDOMINANT COCAINE ABUSING GROUPS

| PARAMETERS TESTED | CONTROL GROUP (a) Mean ± S.E. | PSYCHIATRIC GROUP (b) Mean ± S.E. | LEAST SEVERE ALCOHOLIC (c) Mean ± S.E. | MOST SEVERE ALCOHOLIC (d) Mean ± S.E. |
|---|---|---|---|---|
| TBA | 36.2 ± 6.6 | 62.7 ± 6.1 | 72.2 ± 7.7 | 72.9 ± 7.7 |
| ECLA | 65.4 ± 4.8 | 57.9 ± 1.9 | 69.5 ± 6.7 | 56 ± 0 |
| ECLT | 53.0 ± 0 | 60.7 ± 3.7 | 59.5 ± 4.5 | 66.8 ± 5.2 |
| ECLG | 53.4 ± 6.9 | 58.2 ± 5.4 | 65.0 ± 7.6 | 64.2 ± 7.6 |
| ECLST | 56.5 ± 0 | 58.5 ± 1.2 | 52.8 ± 3.3 | 64.8 ± 4.6 |
| ECLTCV | 59.5 ± 0 | 59.5 ± 0 | 59.5 ± 0 | 62.19 ± 2.7 |
| EOPT | 49.5 ± 0 | 62.2 ± 4.3 | 62.0 ± 5.7 | 65.6 ± 5.8 |
| EOPBCV | 60.5 ± 0 | 60.5 ± 0 | 60.5 ± 0 | 60.5 ± 0 |
| VER | 37.0 ± 5.6 | 65.5 ± 5.8 | 65.6 ± 9.0 | 61.2 ± 6.9 |
| VCZ | 73.6 ± 5.7 | 50.6 ± 5.7 | 42.4 ± 6.8 | 53.7 ± 6.1 |

| PARAMETERS TESTED | PREDOMINANT COCAINE (e) Mean ± S.E. | ONE TAILED ANOVA p Value | WEIGHTED LINER TREND p Value | PAIRED COMPARISONS OF MEANS DUNCANS RANGE TEST AT 0.05 |
|---|---|---|---|---|
| TBA | 76.6 ± 8.9 | .0002 | .0001 | 1 < 2, 3, 4, 5 |
| ECLA | 62.2 ± 4.3 | .035 | .710 | 3 < 4 and 2 < 3 |
| ECLT | 72.4 ± 6.8 | .060 | .010 | 1 < 5 |
| ECLG | 76.7 ± 8.6 | .09 | .015 | NS |
| ECLST | 72.0 ± 6.1 | .024 | .0034 | 1, 2, 3 < 5 |

TABLE 8-continued

| | | | | |
|---|---|---|---|---|
| ECLTCV | 6S.7 ± 4.4 | .094 | .029 | 1, 2 < 5 |
| EOPT | 69.8 ± 7.0 | .115 | .038 | 1 < 5 |
| EOPBCV | 66.9 ± 4.4 | .025 | .029 | 1, 2, 3, 4 < 5 |
| VER | 68.5 ± 7.7 | .030 | .075 | 1 < 4, 2, 3, 5 |
| VCZ | 53.3 ± 9.0 | .046 | .154 | 3, 2 < 1 f | a. The control group consisted of 16 subjects and for the Duncans Range Test it is categorized as group 1.

b. The psychiatric group without comorbid polysubstance abuse consisted of thirty-four subjects and for the Duncans range test it is categorized as group 2.

c. The least severe alcoholic group consisted of 19 subjects and for the Duncans Range Test it is categorized as group 3.

d. The most severe alcoholic group consisted of 23 subjects and for the Duncans Range Test it is categorized as group 4.

e. The predominant cocaine group consisted of 19 subjects and for the Duncan Range Test it is categorized as group 5.

f. In P300 the higher voltage relates to a more normal value.

DEFINITION OF PARAMETERS:
A=Alpha
D=Delta
S=Symmetry
EOP=Eyes opened
$P_Z$=Parietal Central
CZ=Central Electrode
CV=Coefficient of Variation
V=Differential voltage of P300
G=All bands added-general
AER=Auditory Evoked Response
AERT=AER Temporal
AERBI=AER Bitemporal
AERBIT=AER Bitemporal & Temporal
AVT=AER & EVER Bitemporal & Temporal
VER=Visual Evoked Response
VERBI=VER Bitemporal
VERT=VER Temporal
VERBIT-BER Bitemporal & Temporal
AVBI=VER Bitemporal & Temporal
EP=AER+VER Evoked Potentials
TBA=Total BEAM Abnormalities-all parameters except P300
MAX=Maximum Voltage or Latency Time of P300 at any electrode
B=Beta
T=Theta
T=TIME
ECL=Eyes closed This instrument also provided an assessment of drug/alcohol severity use patterns. Selection mandated that the drug use was not active for at least one week prior to the brain map as assessed by history. There was a 100% agreement on drug use history between two independent clinical raters. Additionally, to subdivide each polysubstance abusing subject, their first drug of choice was assessed. All subjects were part of a catchment study involving $D_2$ dopamine receptor genotyping which received IRB approval from the University of Texas Health Science Center at San Antonio, whereby each subject filled out an approved consent form.

3. Electrophysical Methods

A total of 111 subjects were analyzed by BEAM™, a device which is a registered trademark of Nicolet Instruments Corporation. A 24-channel EEG recorder was utilized using the standard 10/20 system of electrode placement, plus two earlobe and supraorbital electrodes. Our group used electrocap and found no difference between BEAM™ with or without electrocap. Electrocap has been used effectively at major centers in epilepsy research (Treiman et al., 1990; Blom and Anneveldt, 1982; Blom and Mechelse; 1980). Digitized EEG was recorded in monopolar and bipolar montage for one hour.

Digitized EEG's, spectral analysis, and EP's (evoked potentials) were stored on optical disk of BEAM™ Nicolet System. Eye, EMG, and EKG monitors were employed throughout the recording. Grass photic stimulation (model PS22C) at 0.5 hertz was performed. The tracing captured wakefulness and drowsiness. In sum (see Table 8), the BEAM™ procedure consists of an EEG, eyes open and eyes closed, spectral analysis, Visual Evoked Response (EVER) (3 runs of 100 flashes at 0.5 hertz), Auditory Evoked Response (AER) (3 runs of 100 clicks by earphone), and P300 tests done by standard auditory oddball paradigm of burst tones (1 KHz frequent, 2 KHz rare tone, 85 db SPL [Sound Pressure Level] with analysis of difference between frequent and rare tone).

Significance for spectral analysis was 2 or more SD (standard deviations) after analysis of 10 or more 2-second epochs of EEG. For evoked potentials, significance of EVER and AER was 2.5 SD and reoccurrence of deficits in all three files at the same location of 2.5 or more SD. Interobserver reliability was 100% for topographical changes and for EEG. EEG was read by an independent electroencephalographer without knowledge of subject diagnosis and a conferring physician trained in EEG.

Encephalographers rated each EEG study, using conventional EEG criteria to assess the degree of cerebral dysrhythmia, including estimated posterior dominant frequency and amount of slow wave activity in the theta and delta frequency ranges (scored as 0=none, 1=minimal amount, 2=moderate amount, 3=large amount). In addition, the May Clinic classification criteria (Kalss and Sharborough, 1981), were used to assign an overall dysrhythmia score to each EEG study. Both the EVER and AER were analyzed at 20 msec, and power, symmetry, and coefficient of variation were done for spectral analysis in all bands. P300 was analyzed at $C_Z$, $P_Z$, and $P_{Max}$ (maximum voltage regardless of electrode) for time and voltage (differential voltage) (Table 8).

A severity scale was designed which consisted of the addition of abnormal quadrant sites plus standard deviations. For example, if an evoked potential map was abnormal to a max of 2.8 SD in both frontal temporal and parietal regions or two quadrants, the severity of this abnormality was rated as 4.8. All excesses or deficiencies in spectral analysis, or positive or negative EP abnormalities, were assigned a positive number. In sum, this is a rating system based on the addition of SD's modified only by differential weighing the area involved to each topographic abnormality with quadrants emphasized rather than electrodes (personal communication, Leslie Kelman, M.D., director of Nicolet BEAM™ Training) because of the clinical significance of one temporal electrode abnormality compared to 2–3 parietal, frontal, or occipital area abnormalities—area was therefore generalized to quadrant.

In order to compare electrophysiological parameters in probands and controls, a control group data base (n=60) of the Nicolet BEAM™ II System provided by Frank Duffy at Harvard (Duffy et al., 1984a) was used. All groups described above underwent total brain map analysis which consisted of spectral analysis of six bands of hertz: δ0–3.5, θ4–7.5, α8–11.5, β1, 12–15.5, β2, 16–19.5; and β3, 20–24. An average AER and EVER was calculated after three runs. VER was read for N (negative peak)$_1$, P (positive peak)$_1$, P$_2$, N$_2$ and AER N$_1$, P$_1$, N$_2$-values were normalized and color coded topographically according to the BEAM™ system (Garber et al., 1989). The total number of parameters measured, excluding the artifact files (β2, β3, and figure of merit) and EEG, was 40 (see Table 8).

4. Measurement of Temporal Lobe Localization Data

Abnormalities of electrophysiology of temporal lobes were measured at F8, T4, T6 (right temporal) and F7, T3, T5 (left temporal). If one or more temporal lobe electrodes was abnormal at 2.5 SD or more, it was counted as abnormal with each time epoch (25 over 500 msec) being evaluated. Bitemporal abnormalities were defined as one or more abnormalities occurring at both temporal lobes in the same epoch. Such measurements were done for VER and AER only. Similar evaluations were done for frontal, parietal, and occipital regions.

5. Statistical Analysis

Measures of EEG were analyzed as BEAM™ scores and also were dichotomized into abnormal or normal. Composite measures, or the sum of the abnormal measures within a class of measures, were calculated for eyes open and closed, power, symmetry, coefficient of variation, evoked potentials and P300, and the total of all abnormal measures (see Table 8).

Between-group comparisons for EEG measures were calculated with the Oneway procedure for Analysis of Variance and cross tabulation procedure for chi square tests in the SPSS computer program (Statistical Package for the Social Sciences, SPSS, Inc., Version 4.0). One-tailed alpha probability criteria were used for those group comparisons which involved an a priori direction of the means. Linear trends were examined in both the ANOVA's and chi square tables. A linear increase in abnormal values was predicted going from control to psychiatrically-ill to alcoholic and then cocaine abuse.

The variances of EEG measures between the groups of control, psychiatric, alcohol, and cocaine patients were not homogeneous. Thus, statistical procedures which relied on the assumption of homogeneity of variance, i.e. Analysis of Variance, could only be employed after transformation of the dependent measures. The dependent measures were transformed into ranks and analyzed using Analysis of Variance with Duncan post hoc group mean comparisons (Conover and Iman, 1981).

B. RESULTS

Table 9 shows the mean differences, standard errors, tail probabilities, linear trends, and paired comparisons of the means in 16 assessed CS, 34 PNPS, 19 LSA, 23 MSA, and 19 COKE subjects. The table includes only those parameters which were either significant at an 0.05 α level utilizing a one-tailed ANOVA or a linear trend analysis. Comparison between these five groups yielded significant ANOVA differences in 10 (TBA, ECLA, ECLT, ECLG, ECLST, ECLTCV, EOPT, EOPBCV, VER, and VCZ) of 40 brain map parameters tested, or 25 percent overall differences in brain topography. In terms of increased abnormalities, it is noteworthy that in the above 10 tested parameters, eight out of 10 measures, or 80 percent, resulted in a worsening effect in the polysubstance abusing subjects (PPS) compared to either the PNPS or CS groups utilizing the Duncans range test. Moreover, it appears that the effect worsened in the COKE group compared to either LSA, MSA, and PNPS groups. Out of the 10 parameters found to be significant, seven (TBA, ECLT, ECLST, ECLTCV, EOPT, EOPBLV, and VER), or 70 percent, worsened in the COKE group. Further support is derived from the weighted linear trend analysis which revealed a significant difference in the same parameters (TBA, ECLT, ECLST, ECLTCV, EOPT, and EOPBCV) excluding the VER for a total of 60 percent.

As revealed in Table 10, the composite of total brain abnormalities, or TBA, was significantly worse ($p<0.0002$) in the polysubstance abusing groups (LSA, MSA, and COKE) as well as in the PNPS group compared to CS. Moreover, a weighted linear trend was significant ($p=0.001$).

Table 10 illustrates statistical comparisons of the means in 16 CS, 34 PNPS, and 42 PPS (combination of both MSA and COKE groups) subjects. The table includes only those parameters which were significant (as described for Table 9). Comparison between these three groups yielded significant differences in ANOVA and linear trend analysis in nine (TBA, ECLT, ECLST, ECLSG, EOPL, EOPT, VER, EP, and VCZ) out of 40 brain map parameters tests or 22.5 percent overall differences in brain topography. As previously noted in Table 9, increased abnormalities were observed in eight out of nine measures or 88.8 percent in the PPS group compared to the PNPS and 100 percent when compared to CS in the ANOVA and Duncans range test, excluding linear trend. Unlike the findings observed in Table 10, a PPS subgroup was not significantly different in terms of P300 compared to the PNPS group. Moreover, the composite of total brain abnormalities (TBA) was significantly worse in PPS and PNPS groups ($p<0.0003$) compared to CS, with a significant weighted linear trend at $p=0.0002$.

In order to further characterize the data, the PNPS and PPS groups were further subdivided into only those patients diagnosed with major depressive illness. Table 11 shows statistical comparisons of the means in 16 CS, 12 PNPS, and 9 PPS (combined MSA and COKE) subjects. As previously stated, the only parameters cited in Table 11 are those which were significant (see Tables 8 and 9). Comparison between these three yielded significant differences in ANOVA and linear trend analyses in 10 (TBA, ECLT, ECLST, EOPG, EOPT, EOPB, EOPSA, VER, AERS, EP) out of 40 brain map parameters assessed, or 25 percent overall differences in brain topography. With this depressed subgroup, once again increased abnormalities were observed in 9 out of 10

TABLE 9

SIGNIFICANT BEAM COMPARISONS IN CONTROLS VS MATCHED PSYCHIATRICALLY-ILL AND POLY-SUBSTANCE ABUSING SUBJECTS

| PARAMETER TESTED | CONTROL GROUP (a) Mean ± S.E. | PSYCHIATRIC GROUP (b) Mean ± S.E. | POLY-SUBSTANCE ABUSE GROUP (c) Mean ± S.E. |
|---|---|---|---|
| TBA SPECTRAL ANALYSIS | 36.2 ± 6.6 | 62.7 ± 6.1 | 73.8 ± 4.4 |
| ECLT | 53.0 ± 0 | 60.7 ± 3.7 | 68.8 ± 4.2 |
| ECLST | 56.5 ± 0 | 58.5 ± 2.0 | 68.1 ± 3.7 |
| ECLSG | 53.4 ± 6.8 | 56.2 ± 5.2 | 70.2 ± 4.4 |
| EOPG | 45.3 ± 6.3 | 65.4 ± 5.9 | 70.1 ± 4.4 |
| EOPT | 49.5 ± 0 | 62.2 ± 4.3 | 67.5 ± 4.5 |
| EVOKED POTENTIALS | | | |
| VER | 37.0 ± 5.6 | 65.5 ± 5.8 | 64.5 ± 5.1 |
| EP | 36.5 ± 6.1 | 66.38 ± 6.2 | 72.0 ± 5.3 |
| VCZ | 73.6 ± 5.7 | 50.5 ± 5.6 | 53.5 ± 5.3 |

| PARAMETER TESTED | ONE-TAILED ANOVA (p VALUE) | WEIGHTED LINEAR TREND p VALUE | PAIRED COMPARISONS OF MEANS DUNCAN RANGE TEST OF 0.05 |
|---|---|---|---|
| TBA SPECTRAL ANALYSIS | .0003 | .0002 | 1 < 2, 3 |
| ECLT | .003 | .02 | 1 < 3 |
| ECLST | .015 | .01 | 2 < 3 |
| ECLSG | .004 | .032 | 1 < 3 |
| EOPG | .016 | .018 | 1 < 3 |
| EOPT | .035 | .03 | 1 < 3 |
| EVOKED POTENTIALS | | | |
| VER | .005 | .03 | 1 < 2, 3 |
| EP | .001 | .002 | 1 < 2, 3 |
| VCZ | .02 | .06 | 2, 3 < 1 d |

(a) The control group consisted of 16 subjects and for the Duncans Range Test it is categorized as group 1.
(b) The psychiatric group without comorbid polysubstance abuse consisted of 34 subjects and for the Duncans Range Test it is categorized as group 2.
(c) The polysubstance abuse (combined most-severe alcoholics and predominant cocaine subjects) consisted of 42 patients and for the Duncans Range Test it is categorized as group 3.
(d) In P300 the higher voltage relates to a more normal value.

measures, or 90 percent in the PPS group compared to the PNPS and CS groups as depicted by the Duncans range test. The depressed subdivided groups (PNPS and PPS) were not significantly different in terms of the P300 component compared to CS.

In general, the dominant abnormal spectral band was increased theta abnormalities in both PPS and PNPS groups compared to CS. Specifically, with LSA, MSA, and COKE, theta abnormalities occurred in ECLT, ECLST, ECLTCV, and EOPT (see Table 9); with PPS (MSA and COKE), theta abnormalities occurred in ECLT, ECLST, and EOPT (see Table 10); and with the depressed PPS (MSA and COKE), theta abnormalities similarly occurred in ECLT, ECLST, AND EOPT (see Table 11). Notable there were no significant differences in EEG between any of the groups.

It is notable that out of all brain map parameters tested, the EP data, as depicted in Table 10, reveals the most severe abnormalities with a p value of 0.0003 (ANOVA) compared to both spectral analysis and P300. Moreover, as the severity of polysubstance abuse seeking was characterized as well as type of psychiatric problem, an increasing percentage abnormality was found in the EP. The order of EP abnormalities increased accordingly, whereby LSA<(see Table 8), MSA<COKE (see Table 9),<depressed MSA plus COKE (see Table 10). More specifically, it was found that total evoked potentials (which includes VER, AER, VERS, AERS, and EP) increased accordingly, whereby Table 8 had 20 percent abnormalities, Table 9 had 40 percent abnormalities, and Table 10 had the largest percentage deficit at 60 percent.

TABLE 10

SIGNIFICANT BEAM COMPARISONS IN CONTROLS VS PSYCHIATRICALLY-DEPRESSED PATIENTS AND DEPRESSED POLYSUBSTANCE ABUSING SUBJECTS

| PARAMETER TESTED | CONTROL GROUP (a) Mean ± S.E. | PSYCHIATRIC GROUP (b) Mean ± S.E. | POLY-SUBSTANCE ABUSE GROUP (c) Mean ± S.E. |
|---|---|---|---|
| TBA SPECTRAL ANALYSIS | 36.2 ± 6.6 | 62.7 ± 8.5 | 83.2 ± 11.7 |
| ECLT | 53.0 ± 0 | 58.5 ± 5.5 | 73.3 ± 10.2 |
| ECLST | 56.5 ± 0 | 56.0 ± 0 | 70.4 ± 9.2 |
| EOPG | 45.7 ± 6.3 | 63.4 ± 8.0 | 79.2 ± 12.8 |
| EOPT | 49.5 ± 0 | 54.5 ± 5.0 | 78.7 ± 11.7 |
| EOPB | 51.5 ± 0 | 51.5 ± 0 | 65.0 ± 8.9 |
| EOPSA | 58.0 ± 0 | 58.0 ± 0 | 71.1 ± 8.7 |
| EVOKED POTENTIALS | | | |
| VER | 37.0 ± 5.6 | 61.8 ± 11.0 | 74.3 ± 10.8 |
| AERS | 47.6 ± 4.6 | 75.9 ± 9.9 | 75.4 ± 10.4 |
| EP | 36.5 ± 6.1 | 74.0 ± 11.8 | 88.6 ± 8.9 |

| PARAMETER TESTED | ONE-TAILED ANOVA p VALUE | WEIGHTED LINEAR TREND p VALUE | PAIRED COMPARISONS OF MEANS DUNCAN RANGE TEST OF 0.05 |
|---|---|---|---|
| TBA SPECTRAL ANALYSIS | .0005 | .0003 | 1 < 2, 3 |
| ECLT | .027 | .020 | 1 < 3 |
| ECLST | .023 | .036 | 1, 2 < 3 |
| EOPG | .016 | .009 | 1 < 3 |
| EOPT | .003 | .003 | 1, 2 < 3 |
| EOPB | .023 | .036 | 1, 2 < 3 |
| EOPSA | .023 | .036 | 1, 2 < 3 |
| EVOKED POTENTIALS | | | |
| VER | .009 | .006 | 1 < 2, 3 |
| AERS | .009 | .013 | 1 < 3, 2 |
| EP | .0003 | .002 | 1 < 2, 3 |

(a) The control group consisted of 16 subjects and for the Duncans Range Test it is categorized as group 1.
(b) The psychiatric group without combined polysubstance abuse consisted of 12 subjects and for the Duncans Range Test it is categorized as group 2.
(c) The polysubstance abuse (combined most-severe alcoholics and predominant cocaine subjects) consisted of 9 patients and for the Duncans Range Test it is categorized as group 3.

Keeping the data in mind, a systematic evaluation of the location of evoked potential abnormalities in AER and VER files was performed. Table 11 shows increased temporal lobe abnormalities in 16 CS, 34 PNPS, 19 CSA, 23 MSA, and 19 COKE subjects. The table includes only those parameters which were significant at a 0.05 α level utilizing a one-tailed ANOVA or a linear trend analysis. Comparison between these five groups yielded significant ANOVA differences in eight (AERBI, VERBI, VERT, AERBIT, VRBIT, AVBI, AVT, and AVBIT) of nine temporal lobe parameters tested, or 88.8% overall differences in brain topography. Notably, bitemporal regions, particularly in the VER parameter, are significantly more affected in the PPS group, whereas AERT is not significant. In terms of increased abnormalities, seven out of eight measures, or 87.5%, resulted in a worsening effect in the polysubstance abusing subjects compared to either the PNPS or CS groups utilizing the Duncans range test. For temporal lobe abnormalities, it appears that the effect worsened in the MSA group compared to either LSA or COKE and PNPS groups. Out of the eight parameters found to be significant, five (VERBI, VERT, AVBI, AVT, and AVBIT) or 62.5%, worsened in the MSA group. When both alcohol groups were combined, i.e., LSA and MSA, the total temporal abnormalities increased to 87.5%. Further support is derived from the weighted linear trend analysis showing a significant difference in six out of nine parameters (VERBI, VERT, BERBIT, AVBI, AVT, and AVBIT) for a total of 66%.

abnormalities were observed in six out of eight measures, or 75% in the PPS group compared to the PNPS. Most notably, and in opposition to Table 12, VERT and AVT regions are worse in PNPS compared to PPS by weighted linear trend ($p=0.0135$), and Duncan's range test. However, when comparing PPS to CS, there are 100 percent abnormalities worse than controls. Specifically, in all bitemporal parameters, when comparing PPS to PNPS, six out of six files, or 100 percent of the time, the PPS group has significantly greater abnormalities than the PNPS group by Duncan range test.

In order to further characterize the data, both PNPS and PPS groups were subdivided into those patients having a diagnosis of major depressive illness.

TABLE 11

INCREASED TEMPORAL LOBE ABNORMALITIES IN CONTROLS VS MATCHED PSYCHIATRICALLY-ILL PATIENTS,
LEAST SEVERE ALCOHOLICS, MOST SEVERE ALCOHOLICS, AND PREDOMINANT COCAINE ABUSING GROUPS

| PARAMETERS TESTED | CONTROL GROUP MEAN ± S.E. | PSYCHIATRIC MEAN ± S.E. | LEAST SEVERE MEAN ± S.E. | MOST SEVERE MEAN ± S.E. |
|---|---|---|---|---|
| AER BITEMPOPAL | 49.5 ± 0 | 52.77 ± 2.28 | 64.36 ± 5.88 | 58.82 ± 4.33 |
| VER BITEMPORAL | 38 ± 0 | 56.14 ± 4.35 | 58.57 ± 7.19 | 61.82 ± 5.99 |
| AER TEMPORAL | 45.81 ± 3.31 | 58.08 ± 4.2 | 62.73 ± 6.28 | 55.19 ± 5.17 |
| VER TEMPORAL | 38.23 ± 4.23 | 59.97 ± 4.94 | 45.68 ± 5.49 | 65.8 ± 6.15 |
| AER BITEMPORAL & TEMPORAL | 41.59 ± 3.09 | 56.53 ± 4.3 | 68.63 ± 6.9 | 56.28 ± 5.8 |
| VER BITEMPORAL & TEMPORAL | 32.28 ± | 59.17 ± 4.77 | 55.10 ± 7.66 | 63.91 ± 6.43 |
| AER & VER BITEMPORAL | 35.0 ± 0 | 53.1 ± 4.5 | 61.79 ± 7.67 | 65.04 ± 5.86 |
| AER & VER TEMPORAL | 34.28 ± 4.76 | 60.16 ± 5.11 | 51.47 ± 6.51 | 65.48 ± 6.37 |
| AER & VER BITEMPORAL & TEMPORAL | 27.23 ± 3.67 | 57.39 ± 4.88 | 62.58 ± 7.49 | 66.86 ± 5.96 |

| PARAMETERS TESTED | ONE TAILED ANOVA p VALUE | WEIGHTED LINER TREND p VALUE | PAIRED COMPARISONS OF MEANS DUNCANS RANGE TEST AT 0.05 |
|---|---|---|---|
| AER BITEMPORAL | .0457 | .1468 | 1, 2 3 |
| VER BITEMPORAL | .025 | .0147 | 1 < 2, 3, 5, 4 |
| AER TEMPORAL | .834 | .5505 | NS |
| VER TEMPORAL | .0037 | .0184 | 1 < 2, 5, 4 + 3 < 4 |
| AER BITEMPORAL & TEMPORAL | .025 | .2921 | 1 < 3 |
| VER BITEMPORAL & TEMPORAL | .0056 | .0103 | 1 < 3, 2, 4, 5 |
| AER & VER BITEMPORAL | .0045 | .0028 | 1 < 2, 5, 3, 4 |
| AER & VER TEMPORAL | .0065 | .0242 | 1 < 5, 2, 4 |
| AER & VER BITEMPORAL & TEMPORAL | .0005 | .0039 | 1 < 2, 5, 3, 4 | a. The number of subjects utilized in this study included: 16 non-psychiatrically diagnosed controls, 46 total psychiatrically diagnosed group; LSA = 19; MSA = 23; Cocaine = 19
b. Denotes pairs of groups significantly different designated as control = 1; psychiatric = 2; least severe alcoholic = 3; most-severe alcoholic = 4; and predominant cocaine = 5.

Since it was previously found that when all alcoholic groups were combined together (LSA plus MSA) there is an enhanced number of temporal lobe abnormalities (see Table 11), the LSA group was included in the PPS group to more completely evaluate alcohol's effects on their parameters.

Table 12 illustrates statistical comparisons of the means in 16 CS, 34 PNPS, and 61 PPS (LSA plus MSA and COKE) groups. Comparison between these three groups yielded significant differences in ANOVA and linear trend analysis in eight (AERBI, VERBI, VERT, AERBIT, VERBIT, AVBI, AVT, and AVBIT) out of nine parameters tested, or 88.8% overall differences in temporal lobe abnormalities. Increased

TABLE 12

INCREASED TEMPORAL LOBE ABNORMALITIES IN COMBINED POLYSUBSTANCE ABUSING
SUBJECTS COMPARED TO BOTH THE TOTAL PSYCHIATRIC GROUP AND CONTROLS[a]

| PARAMETER TESTED | CONTROL GROUP (a) Mean ± S.E. | PSYCHIATRIC GROUP (b) Mean ± S.E. | POLYSUBSTANCE ABUSE GROUP (c) Mean ± S.E. |
|---|---|---|---|
| AER BITEMPORAL | 49.5 ± 0 | 52.8 ± 2.3 | 59.5 ± 2.7 |
| VER BITEMPORAL | 38 ± 0 | 56.1 ± 4.3 | 60.6 ± 3.7 |
| AER TEMPORAL | 45.8 ± 3.3 | 58.1 ± 4.2 | 57.5 ± 3.3 |
| VER TEMPORAL | 38.2 ± 4.2 | 60.0 ± 4.9 | 58.4 ± 3.6 |
| AER BITEMPORAL & TEMPORAL | 41.6 ± 3.1 | 56.5 ± 4.3 | 59.5 ± 3.7 |
| VER BITEMPORAL & TEMPORAL | 32.3 ± 3.3 | 59.2 ± 4.8 | 60.4 ± 4.0 |
| AER & VER BITEMPORAL | 35.0 ± 0 | 53.7 ± 4.5 | 62.8 ± 3.8 |
| AER & VER TEMPORAL | 34.3 ± 4.8 | 60.2 ± 5.1 | 59.4 ± 3.8 |
| AER & VER BITEMPORAL & TEMPORAL | 27.2 ± 3.7 | 57.4 ± 4.9 | 62.8 ± 4.0 |

| PARAMETER TESTED | ONE-TAILED ANOVA p VALUE | WEIGHTED LINEAR TREND p VALUE | PAIRED COMPARISONS OF MEANS DUNCAN RANGE TEST OF 0.05 |
|---|---|---|---|
| AER BITEMPORAL | .031 | .0209 | 1, 3 |
| VER BITEMPORAL | .0045 | .0047 | 1 < 2, 3 |
| AER TEMPORAL | .093 | .166 | NS |
| VER TEMPORAL | .0106 | .0407 | 1 < 3, 2 |
| AER BITEMPORAL & TEMPORAL | .0259 | .027 | 1 < 3 |
| VER BITEMPORAL & TEMPORAL | .0010 | .0035 | 1 < 2, 3 |
| AER & VER BITEMPORAL | .005 | .0004 | 1 < 2, 3 |
| AER & VER TEMPORAL | .0031 | .0135 | 1 < 3, 2 |
| AER & VER BITEMPORAL & TEMPORAL | .0001 | .0001 | 1 < 2, 3 |

(a) The number of subjects utilized in this study included: 16 non-psychiatrically diagnosed controls, 34 total psychiatrically diagnosed group; 63 combined polysubstance abusing subjects (Combined Least Severe Alcoholic, Most Severe Alcoholic or Cocaine Groups).
(b) Denotes pairs or groups significantly different designated as control = 1; psychiatric = 2; polysubstance abusing group = 3

Table 13 shows the means of temporal lobe abnormalities in 16 CS, 12 PNPS, and nine PPS subjects. Comparisons between these three groups yielded significant differences in both ANOVA and linear trend analyses in eight (VERBI, AERT, VERT, AERBIT, VERBIT, AVBI, AVT, and AVBIT) out of nine temporal lobe abnormalities, or 88%. With this depressed group, it is notable that increased abnormalities were observed in eight out of eight measures, or 100% in the PPS group compared to PNPS and CS groups as depicted by the Duncan's range test. However, when PNPS is compared to the CS group, it is only 75%. Most strikingly, scrutiny of the data reveals highly significant ANOVA and linear trends in three important evoked potential measures (AVBI, AVT, and AVBIT), sub-categories of the evoked potential files previously defined, where p=0.0000001 (AVBIT), the strongest finding in the entire data set.

Figure 4C:
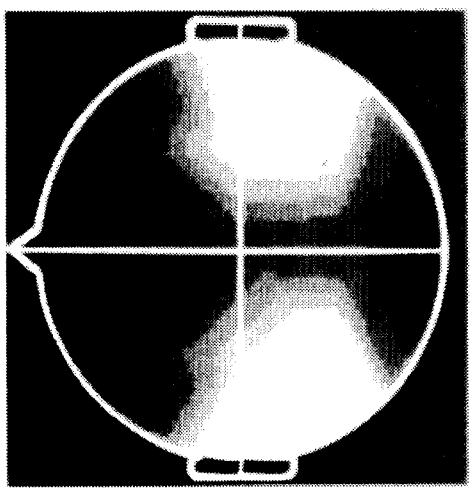
FIG. 4C. This is a characteristic BEAM™ of the EVER in a polysubstance abuser with unipolar depression, with a left and right bitemporal excess negative to 2.78 SD (minimum) (maximum −0.27) appears bright white. This map is also characteristic of patients with a history of violence. The rating for this particular map is 4.78. While this bitemporal excess negativity was not typically found in non-polysubstance abusing unipolar depressed patients, it was especially characteristic in those matched unipolar-depressed (and other psychiatric disorder) patients abusing alcohol and cocaine. This typical map occurred more significantly in severe alcohol abusers than in cocaine abusers.
Figure 4B:
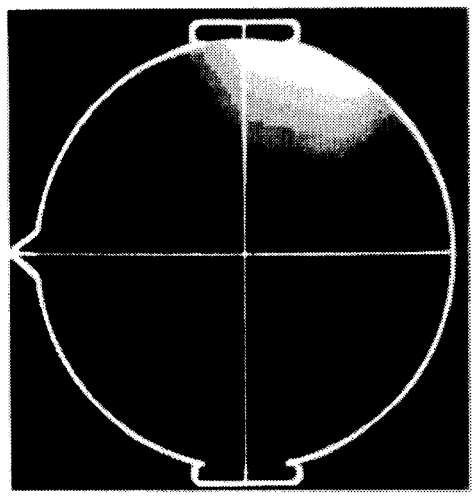
FIG. 4B. This is a characteristic brain electrical activity map of the EVER in a psychiatrically-ill patient with unipolar depression, with a right temporal excess negativity to 2.90 DS (minimum) (maximum 0.27) as shown by a bright white. The right temporal abnormality exhibited by the light white-grey area is typical of individuals with depression, i.e., mood swings, palpitations, anxiety, and stress. The rating for this particular map is 3.90. This right temporal excess negativity is also found in brain maps of polysubstance abusers with unipolar depression (and other psychiatric disorders) more significantly than controls and approximately equal (sometimes slightly more or less) to that observed in unipolar depressed (and other psychiatric disorders) patients not abusing psychoactive drugs (e.g., alcohol, cocaine).
Figure 4B:
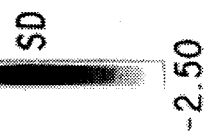
Figure 4A:
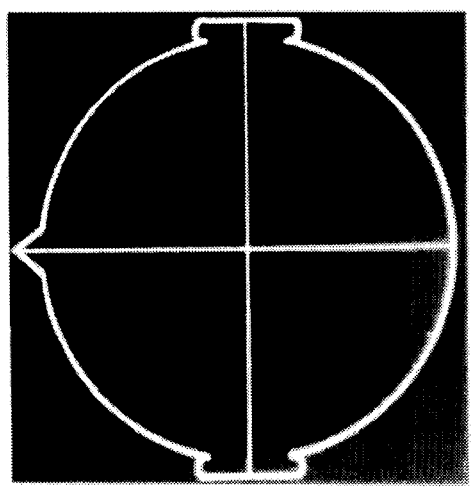
FIG. 4A. Significant probability topographic map (SPM) of the EVER in a typical normal subject. On visual inspection, a homogenous light-dark electrically stable brain electrical activity map is seen. Standard deviation maximum (0.34) and minimum (−1.00) are shown here, and the SPM is not significantly different from the standardized BEAM™ controls. Since there is no defect, the brain map rating is zero.

FIG. 4A is a significant probability topographic map (SPM) of the VER in a typical normal subject. On visual inspection, a homogenous light-dark electrically stable brain electrical activity map is seen. Standard deviation (SD) maximum (0.34) and minimum (−1.00) are shown here as SPM, and our control group is not significantly different from the standardized BEAM™ controls. Since there is no defect, the brain electrical activity map of the VER in a single psychiatrically-ill patient with unipolar depression, with a right temporal excess negativity to 2.90 SD appears bright white. The right temporal abnormality exhibited by the light grey area is typical of individuals with depression, i.e., mood swings, palpitations, anxiety, and stress, with or without polysubstance abuse (FIG. 4B). The rating for this particular map is 3.90. FIG. 4C shows a characteristic brain electrical activity map of the EVER in a polysubstance abuser with unipolar depression, with a left and right temporal excess negative to 2.78 SD appears bright white to grey. The rating for this particular map is 4.78. This map is also characteristic

TABLE 13

INCREASED TEMPORAL LOBE ABNORMALITIES IN UNIPOLAR DEPRESSED
DRUG ABUSING SUBJECTS COMPARED TO DEPRESSED SUBJECTS AND NORMAL CONTROLS

| PARAMETER TESTED | CONTROL GROUP (a) Mean ± S.E. | PSYCHIATRIC GROUP (b) Mean ± S.E. | POLYSUBSTANCE ABUSE GROUP (c) Mean ± S.E. |
|---|---|---|---|
| AER BITEMPORAL | 49.5 ± 0 | 53.87 ± 4.37 | 55.33 ± 5.43 |
| VER BITEMPORAL | 38.0 ± 0 | 58.08 ± 1.27 | 75.11 ± 4.78 |
| AER TEMPORAL | 5.81 ± 3.31 | 56.75 ± 6.917 | 74.94 ± 10.41 |
| VER TEMPORAL | 38.22 ± 4.22 | 60.33 ± 8.18 | 67.44 ± 9.36 |
| AER BITEMPORAL & TEMPORAL | 41.59 ± 3.094 | 55.00 ± 7.038 | 70.83 ± 10.39 |
| VER BITEMPORAL & TEMPORAL | 32.28 ± 3.28 | 59.54 ± 8.26 | 76.056 ± 9.85 |
| AER & VER BITEMPORAL | 35.0 ± 0 | 55.79 ± 7.53 | 77.16 ± 8.44 |

TABLE 13-continued

| | | | |
|---|---|---|---|
| AER & VER TEMPORAL | 34.28 ± 4.76 | 54.08 ± 8.7 | 84.83 ± 5.11 |
| AER & VER BITEMPORAL & TEMPORAL | 27.22 ± 3.67 | 57.42 ± 8.31 | 84.94 ± 5.25 |

| PARAMETER TESTED | ONE-TAILED ANOVA p VALUE | WEIGHTED LINEAR TREND p VALUE | PAIRED COMPARISONS OF MEANS DUNCAN RANGE TEST OF 0.05 |
|---|---|---|---|
| AER BITEMPORAL | .275 | .2274 | NS |
| VER BITEMPORAL | .0002 | .0001 | 1 < 2, 3 |
| AER TEMPORAL | .0064 | .0039 | 1 < 3 |
| VER TEMPORAL | .004 | .0022 | 1 < 2, 3 |
| AER BITEMPORAL & TEMPORAL | .0057 | .0030 | 1 < 3 |
| VER BITEMPORAL & TEMPORAL | .0001 | .000005 | 1 < 2, 3 |
| AER & VER BITEMPORAL | .00003 | .0000006 | 1 < 2, 3 & 2 < 3 |
| AER & VER TEMPORAL | .00002 | .0000005 | 1 < 2, 3 & 2 < 3 |
| AER & VER BITEMPORAL & TEMPORAL | .0000001 | .00000007 | 1 < 2, 3 & 2 < 3 |

(a) The number of subjects utilized in this study included: 16 non-psychiatrically diagnosed controls, 12 total psychiatrically depressed subjects; 9 combined most severe alcoholic and predominant cocaine abusing subjects.
(b) Denotes pairs or groups significantly different designated as control = 1; psychiatric = 2; and combined most-severe alcoholic and cocaine groups = 3 of patients with a history of polysubstance abuse with or without depression and violence (Braverman, 1993).

EXAMPLE 4

PROLONGED P300 LATENCY IN A NEUROPSYCHIATRIC POPULATION WITH THE $D_2$ DOPAMINE RECEPTOR A1 ALLELE

A. METHODS

1. Subjects

For this study, a total of 155 psychiatrically-ill patients with and without comorbid drug or alcohol abuse categorized as follows: Dysthymia [27.1%]; Generalized anxiety disorder [8.4%]; Unipolar [24.5%]; Bipolar [12.9%]; Schizophrenia [5.2%]; Attention deficit disorder [21.9%]; Chemical dependent [18.1%]; were selected for both genotyping and brain electrical activity mapping. The demographic breakdown of our sample base is illustrated in Tables 14 and 15.

TABLE 14

GENOTYPE DISTRIBUTION OF THE TaqI A ALLELES OF THE $D_2$ DOPAMINE RECEPTOR GENE AS A FUNCTION OF DEMOGRAPHIC CHARACTERISTICS

| GROUP BY GENOTYPE | NO. | GENDER[1] M | GENDER[1] F | PERCENT M | PERCENT F | Mean Age[2] ± S.D. |
|---|---|---|---|---|---|---|
| A2/A2 | 106 | 50 | 56 | 47.2 | 52.8 | 44.76 ± 16.81 |
| A1/A2 | 43 | 21 | 22 | 48.8 | 51.2 | 40.35 ± 14.32 |
| A1/A1 | 6 | 2 | 4 | 33.0 | 67.0 | 52.83 ± 15.93 |

[1]Pearson chi square, p = 0.776
[2]Analysis of variance, p = 0.124

TABLE 15

DIAGNOSTIC CHARACTERISTICS OF A PSYCHIATRICALLY-ILL POPULATION UTILIZED IN THIS STUDY

| TYPE OF DIAGNOSIS | (%) |
|---|---|
| Dysthymia | 27.1 |
| Generalized anxiety disorder | 8.4 |
| Unipolar | 24.5 |
| Bipolar | 12.9 |

TABLE 15-continued

DIAGNOSTIC CHARACTERISTICS OF A PSYCHIATRICALLY-ILL POPULATION UTILIZED IN THIS STUDY

| TYPE OF DIAGNOSIS | (%) |
|---|---|
| Schizophrenia | 5.2 |
| Attention deficit disorder | 21.9 |
| Chemical dependent | 18.1 |

Age and sex and psychiatric disorder were matched. The mean percent of males and the mean percent of females as related to genotypes were not statistically different (p=0.776). Sexual selection included 52.9% female, 47.1% male in our sample population. All subjects signed an approved University of Texas Health Science Center IRB consent form.

Moreover, since P3 latency changes with age (Morelli et al., 1990) age match was also performed according to genotype distribution of the A alleles of the DRD2 gene. The ages of A2/A2; A1/A2 and A1/A1 were 44.76±16.81, 40.65±14.59, 42.83±17.45 respectively. ANOVA analysis revealed no statistically significant difference in age related genotypes (p=0.1509).

2. Electrophysical Analysis

A total of 155 subjects was analyzed by a BEAM™ device describing the quantified EEG and Evoked Potential device with the database n=60 of Frank Durry, at Harvard's Children's Hospital). A 24 channel EEG recorder was utilized incorporating the standard 10/20 system of electrode placement, plus two earlobe and supraorbital electrodes. Digitized EEG was recorded in monopolar and bipolar montage for one hour. Digitized EEG and Eps were stored on optical disk of the BEAM™ Nicolet System. Although this study focuses on the P3 only, eye, EMG and EKG monitors were employed throughout the recording. Gross photic stimulation (model PS22C) and 0.5 Hz was performed. The tracing captured wakefulness and drowsiness. P3 tests were accomplished by standard auditory oddball paradigm of burst tones. P3 was analyzed at $F_z$, $C_z$ and $P_z$, and $P_{max}$ (maximum voltage regardless of electrodes) for time and voltage (differential voltage). For the P3 control group, 18 of 800 patients were selected who were a) drug and alcohol free and b) having no psychiatric disorder and/or having a medical diagnosis not related to CNS or c) were staff volunteers.

3. Genotyping

For this study, a total of 155 probands were genotyped for the TaqI A alleles of the DRD2 dopamine receptor gene. High molecular weight genomic DNA was extracted from whole blood according to the procedures described by Maniatis et al. (1982) the DNA probe, as previously used (Blum et al., 1991a, 1991b) was a 1.73-kilobase (kb) band obtained from a BamHI digest of a human genomic fragment $IhD_2G1$. The fragment includes, in part, the coding sequence of the last exon containing the seventh transmembrane domain of the DRD2 gene and part of the 16.5 kb of the 3' flanking sequence (Grandy et al., 1989a; Grandy et al., 1989b) the 1.73-kb probe was labeled using random-priming with $^{32}P[dCTP]$(Maniatis et al., 1982) to a specific activity of $1\times10^9$ counts/min per μg. The DNA samples after digestion with TaqI were hybridized with the labeled probed, as previously described (Blum et al., 1991a), to reveal the A1 (6.6 kb) and A2 (3.7 kb) alleles.

4. Statistical Analysis

An allelic association of the A1 allele with P3 latency was determined by Analysis of Variance (ANOVA). To determine any linear or quadratic trend, a polynomial trend analysis was employed and the student-Newmans-Keuls procedure was also utilized to denote pairs or groups significantly different at the 0.05 level.

The effect of allele on P3 amplitude and P3 latency were assessed by separate applications of a mixed linear model ANCOVA (SAS Institute, 1989). This type of generalized ANCOVA allows assessment of both fixed and random effects (Harville, 1977). Age was entered into the model as a covariate, after screening for homogeneity of within-group regression coefficients. A $p<0.05$ was considered statistically significant. The data is reported as adjusted (age) mean± standard error (SE)

B. RESULTS

Figure 5:
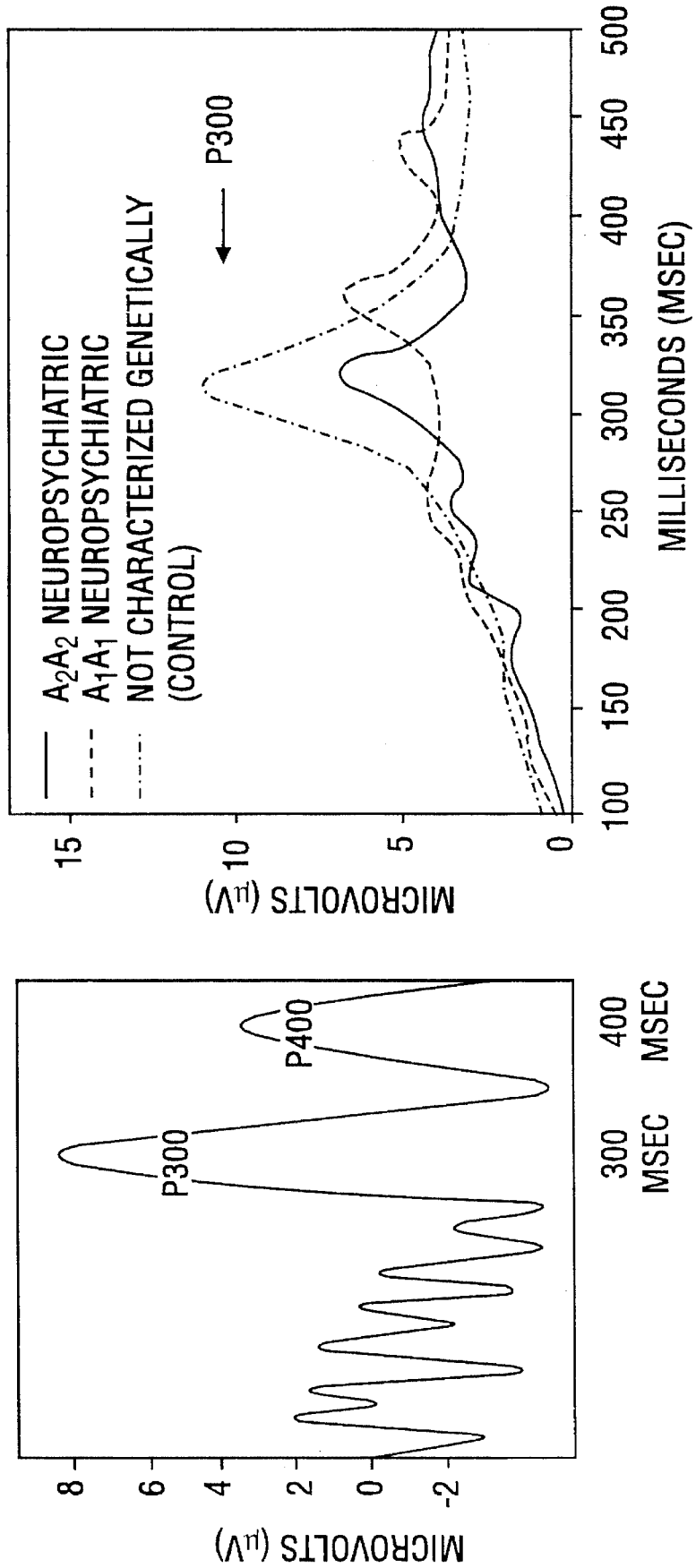
FIG. 5. Relationship of P300 amplitude and latency at $V_{pz}$ and the TaqI A DRD2 alleles in a psychiatrically-ill population. The solid line represents grand total ERP's in a DRD2 A2/A2 psychiatrically-ill patient; the dotted line represents a DRD2 A1/A1 psychiatrically-ill patient at $C_z$, and the dotted-dashed line represents a control (not genetically characterized).

For comparison purposes only, a total of 15 controls (assessed non-polysubstance abusers-psychiatrically "normal" subjects) who were not genotyped were utilized. The P3 amplitude and average P3 time in these controls were 10.9±4.4 mV and 306±27. The grand mean ERP responses of the total number of subjects with A1/A1, A1/A2, A2/A2 alleles were recorded from $F_v$, $C_z$, $P_z$, and $V_{max}$ electrode sites. Although P3 amplitude did not differ within each genotypic group tested, the P3 latency (at $P_z$) was delayed in the A1/A1 group compared to both A1/A2 and A2/A2 groups. FIG. 5 contrasts both P3 amplitude and latency in a) genetically uncharacterized controls; b) psychiatrically-ill A2/A2 genotypes; and c) psychiatrically-ill A1/A1 genotypes.

Table 16 represents the adjusted means for P3 amplitudes and latencies at $P_z$ of A1 and A2 allele subjects. Allele x age ANCOVA was conducted on P3 amplitude. Age was treated as covariate. ANCOVA results showed that there were no significant main effects of allele (except for $P_z$) and no interaction between allele and age. As expected, the covariate age was significantly related to P3 amplitude and latency as a function of different electrode placement (see Table 16).

At least in children, it seems apparent that affected sib-pair linkage analysis would strengthen the impulsive-addictive-compulsive disorder phenotype by utilizing P3 latency as a biological measure to evaluate co-segregation of the DRD2 variants in disordered families. This study also suggests an association of polymorphisms of the DRD2 gene and a biological marker previously indicated to have predictive value in vulnerability to substance abuse.

TABLE 16

RELATIONSHIP OF P300 AMPLITUDE AND LATENCY AT $V_{PZ}$ AND THE TaqI A DRD2 ALLELES IN A PSYCHIATRICALLY-ILL POPULATION

| Group by Genotype | Number of Subjects | Age Adjusted Mean Amplitude[1] (μV) ± S.E. | Age Adjusted Mean Latency[2] (msec) ± S.E. |
|---|---|---|---|
| A2/A2 | 106 | 6.61 ± 0.32 | 327.8 ± 3.08 |
| A1/A2 | 43 | 7.40 ± 0.50 | 323.05 ± 4.86 |
| A1/A1 | 6 | 7.17 ± 1.35 | 360.04 ± 13.02 |

[1]Analysis of variance, (p = .409).
[2]Analysis of variance, (p = .032).

While the allele ANCOVA results of P3 amplitude (A1/A1=7.17±1.35 uV [n=43], A1/A2=7.4±0.5 uV [n=43], A2/A2=6.614±0.32 uV [n=106]) did not reveal a main effect, in contrast, P3 latency (A1/A1=360.0±13.02 msec [n=6], A1/A2=323.05±4.86 msec [n=43], A2/A2=327.8±3.08 [n=106]) revealed a statistical significant difference (p=0.032) whereby the P3 latency was prolonged in the A1 carriers compared to probands with the A2 allele of the DRD2 gene.

A quadratic trend (p=0.01) revealed increasing P3 latency as a function of homozygosity. As shown in Table 16, the age-adjusted mean P3 latency in the A2/A2 group (n=106) was 327.8±3.08 msec compared, by ANOVA, to 360.04±13.02 msec in the A1/A1, (n=6) group (p=0.006). It appears from this data that two copies of the A1 allele induces a prolonged P3 latency compared to either one copy or none. While this data is suspect due to the fact that A1/A2 genotype was not significantly different from the A2/A2 genotype in these subjects, and the sample size of the A1/A1 genotype were quite small, other work tends to support increasing severity in homozygote A1 carriers with regard to polysubstance abuse. However in support of these findings, multiple range testing (student-Newman-Keuls procedure) revealed a significant difference between the A1/A1 genotype compared to both A1/A2 and A2/A2 genotypes in psychiatrical-ill patients with and without comorbid drug and alcohol abuse/dependence.

In support of these findings, results of independent studies suggest that individuals with two copies of the A1 allele are much more likely to develop severe alcoholism than those who have one or none (Arinami et al., 1993). Moreover, the number of receptors $B_{max}$) are more greatly reduced in probands with two copies of the A1 allele of the DRD2 gene from in those who have one or none (Noble et al., 1991b). Furthermore, Suarez et al. (1994) found that two copies of the C1 allele of the DRD2 gene was significantly more prevalent in alcoholics compared too non-alcoholics, 57% and 33% respectively ($\chi^2$=9.8 df=1, p=0.002).

EXAMPLE 5

PROLONGED P300 LATENCY IN CHILDREN WITH THE $D_2$ DOPAMINE RECEPTOR A1 ALLELE

A. METHODS

1. Subjects

Subjects were 98 10 to 14-year-old Caucasian (non-Hispanic) sons of active alcoholic (SAA) fathers, sons of recovering alcoholic (SRA) fathers, and sons of social drinking (SSD) fathers. These boys were recruited by distributing flyers to elementary and junior high schools in the Los Angeles area. Interested parents who called the UCLA Alcohol Research Center were given more detailed information over the telephone, and a brief initial screening interview was conducted with the parent who made the first contact. During this initial screening, the drinking status of the father and family history of alcoholism were obtained. In addition, information was gathered as to the son's history of a learning disability, color blindness, head injury, loss of consciousness, medical or psychiatric disorder, and alcohol and other drug use. Further information was gathered regarding the mother's drinking pattern during her pregnancy with the subject.

2. Interviews

After the initial screening, more in-depth information was obtained from potential families. During this interview, parents were asked to give a list of all known biological relatives with a history or current status of alcoholism, drug abuse, or major psychiatric disorders. Subjects were also asked to describe their present and past patterns of alcohol and drug use and, if recovering alcoholics, the period of their abstinence. To verify the parents' alcohol use history, subjects were asked to choose three individuals who could provide confidential collateral information on this issue. Furthermore, a request was made to provide copies of medical records from treatment facilities on the alcoholic fathers, if treatment for alcoholism was received by them.

The Structured Clinical Interview from the *Diagnostic and Statistical Manual III-Revised* (DSM-III-R) (SCID) (Spitzer et al., 1989) for alcohol dependence was administered to establish the presence or absence of alcoholism in the parents. The SCID was also used to determine the presence or absence of other drug abuse and psychiatric disorders, if these problems were reported by the parents.

Information regarding the son's alcohol and other drug use history was obtained briefly from his parents during the initial screening. More detailed information regarding the son's alcohol and other drug use history was gathered from a modified questionnaire (Jessor and Jessor, 1977) during the son's first appointment. In addition, the son's pediatrician was contacted for verification of his medical and psychiatric history and current status.

3. Inclusion/Exclusion Criteria

Inclusion/exclusion criteria were as follows: First, sons of alcoholics must have fathers who satisfy DSM-III-R criteria for alcohol dependence and also have at least one other first- or second-degree relative who is reported to be an alcoholic. This group may include mothers who have a history of alcoholism, but their drinking during pregnancy with their sons must not have exceeded 4 drinks/wk; second, sons of nonalcoholic social drinking fathers must have mothers who do not have a history of alcoholism and no other first-, second-, or third-degree relative who is reported to be an alcoholic. The mothers' drinking during pregnancy with their sons must not have exceeded 4 drinks/wk; third, sons were excluded if they had parents with a history of major psychiatric disorders (e.g., schizophrenia or affective disorders) unassociated with their drinking; fourth, sons must have no history of alcohol and other drug use and no current use of psychoactive medications; fifth, sons must have no history of serious head injury, significant loss of consciousness (for more than 5 min), learning disability, medical illness, or major psychiatric disorders; sixth, sons must have no hearing or visual impairment (corrected to normal vision acceptable) or color blindness; seventh, parents must be willing to allow the researchers to contact relatives or significant others to verify their past and present drinking patterns, treatment history, and the sons' medical status; eighth, sons must be willing to donate urine samples to be tested for alcohol and illicit drug levels. Subjects must also agree to have breath samples analyzed for alcohol prior to neuropsychological and neurophysiological testing.

The research protocol had the approval of the UCLA Human Subject Protection Committee. All subjects (sons and parents) gave informed consent and were monetarily compensated for their participation.

4. Testing Procedures

The boys were tested individually in the laboratory on two different sessions. In the first session, the Wechsler Intelligence Scale for Children-Revised (WISE-R) (Wechsler 1974) was administered, and Full Scale IQ was calculated. In the second session, the boys were neurophysiologically tested as described below. During each test session, breath samples were analyzed with an Alco-Senor III (Intoximeters) to verify that the subject had not recently consumed alcohol. No boy was found to have alcohol in his system. Moreover, during each of the neuropsychological and neurophysiological sessions, urine samples were collected and screened for eight difference classes of drugs, including ethanol, amphetamines, benzodiazepines, phencyclidine, barbiturates, cocaine, opiates, and tetrahydrocannabinol. None of the 98 boys tested ethanol positive or other-drug positive during any of the test sessions.

5. ERP Measurements

ERPs were recorded with an Electrocap from $R_z$, $C_z$, $P_z$, Fp1, Fp2, F7, F8, T3, T4, T5, T6, C3, C4, P3, P4, O1, and O2 sites of the international 10–20 electrode placement system referred to nosetip. In addition, vertical and horizontal channels of the electrooculogram, (EOG), P300 and $D_2$ Dopamine Receptor Alleles were recorded with a pair of bipolar montages from electrodes situated, respectively, above and below the right eye and on the two outer canthi. Data acquisition and stimulus delivery were controlled by two IBM-compatible microcomputer operating as a SCAN EEG/EP workstation (Neuroscan). Electroencephalogram (EEG) and EOG channels were amplified (band-pass= 0.1–50 Hz) and digitized at a rate of 232 Hz for 1,100 msec, beginning 100 msec prior to stimulus delivery.

Two different versions of a continuous performance task (CPT) using colored shapes were utilized. In one version ($CPT_{10}$) stimuli were circles, triangles, and squares centered on a CTX color monitor in blue, green, red, or violent against a black background for 100 msec (interstimulus interval=2 sec, 2 blocks of 150 stimuli). Each shape had a single white digit at its center. Twenty percent of the items were repetitions of the immediately preceding stimulus and were designated as targets. Since targets had to be identical to the preceding stimulus, they had to be the same on all three features-shape, color, and the identity of the digit. Since the 3 shapes, 4 colors, and 10 digits appeared equally often, the probability of a shape match among nontargets was $\frac{1}{3}$, the probability of a color match was $\frac{1}{4}$, and the probability of a digit match was $\frac{1}{10}$.

In the second version of the CPT ($CPT_4$), only the digits 1–4 were displayed, and a fourth shape was added (a four-lobed clover), so that the probability of a nontarget matching on any single feature was $\frac{1}{4}$. In addition, block size was increased from 150 to 160 stimuli. Otherwise, there were no differences between the two CPTs. Twenty-one subjects received only the $CPT_{10}$, 35 received only $CPT_4$, and 42 subjects received both.

Each stimulus subtended between 3.6 and 4.9 degrees of visual angle both vertically and horizontally, with the central digit subtending 1.2 degrees vertically. Subjects were trained in a practice block to make a speeded button press with the left or right index finger (counterbalanced across subjects) by pressing the left button of a three-button "mouse" pointing device (Logitech) in response to targets. Reaction times (RT) were accepted only between 200 and 1,600 msec poststimulus. Digitized EEG was stored on hard disk and digital audio tape for off-line analysis.

Separate ERP average waveforms were collected for targets and easy nontargets (nontargets not matching on any feature-shape, color, or digit). Only stimuli eliciting the correct behavioral responses (i.e., Go or NoGo) were included in the averages. EEG was corrected, by linear regression, for intrusion of vertical EOG artifact (Semlitsch et al., 1986). Trials containing uncorrectable sources of artifact were eliminated from the averages through visual inspection, without knowledge of family history group or genotype. P3 was measured in the waveform elicited by targets at the $P_z$ electrode as the point of maximum voltage between 300 and 600 ms poststimulus. The latency and amplitude (relative to prestimulus baseline) of this point were stored for statistical analysis, along with percentage of correct target presses and the associated RT. Prior to peak measurement, all averages were low-pass digitally filtered at 15 Hz.

6. DNA Analysis

Genomic DNA was extracted from the blood samples (Olds, 1986) and subsequently used as template for PCR™ (Saiki et al., 1988). The primers 5014 and 971 were used to amplify a 310-bp fragment spanning the polymorphic TaqI A site of the DRD2 gene (Grandy et al., 1989). The sequence of the 5014 primer was 5'-CCgtcg-aCCCTTCCTGAGTGT-CATCA-3'(SEQ ID NO:1); and for the 971 primer was 5'-CCgtcgaCGGCTGGCCAAGTTGTCTA-3'(SEQ ID NO:2); (lowercase letters code for SalI site). The primer sequences were synthesized by Oligos Etc. (Wilsonville, Oreg.).

Amplification was carried out in 100-µl reactions using 1 µg of genomic DNA and 2.5 units of AmpliTaq™ DNA polymerase (Perkin Elmer) in a standard reaction cocktail continuing 200 µM of each of the four dNTPs, 1 mM $MgCl_2$, and the recommended buffer provided by the manufacturer (Perkin Elmer). After an initial denaturation step at 94° C. for 5 min, DNA was amplified in three-step cycles as follows: denaturation at 94° C. for 30 sec, annealing at 58° C. for 30 sec, and extension at 72° C. for 30 sec, using the Perkin Elmer GeneAmp™ 9600 thermocycler. After 35 cycles, a final extension step at 72° C. for 5 min was used.

A 10-µl aliquot was removed and analyzed by gel electrophoresis in a 2.5% agarose gel containing ethidium bromide and was visualized under UV light. The expected 310-bp fragments were visualized with minimal background. Approximately 500 ng of the DNA was digested with 5 units of TaqI restriction enzyme (Boehringer-Mannheim Biochemical) at 65° C. for 2 h. The resulting products were analyzed by agarose gel electrophoresis as described above. The A1/A2 genotype is revealed by three fragments of 310 bp, 180 bp, and 130 bp; the A2/A2 genotype is indicated by two fragments of 180 bp and 130 bp; and the A1/A1 genotype is shown by the uncleaved 310-bp fragment.

7. Statistical Analysis

A $\chi^2$ test was used to assess whether there was a significant difference in the frequency of the A1 and the A2 allele among the three groups of sons. Possible differences in age, educational level, and IQ between group and allelic types (A1=A1/A1 or A1/A2 genotypes; A2=A2/A2 genotype only) were investigated with group (SAA, SRA, and SSD) by allele (A1 and A2) ANOVAs (SAS Institute 1989). The effect of allele, group, and their interaction on P3 amplitude, P3 latency, target accuracy, and RT were assessed by separate applications of a mixed linear model ANCOVA (SAS Institute 1992). This type of generalized ANCOVA allows assessment of both fixed and random effects (Harville 1977). Age, IQ, and CPT type were entered into the model as covariates, after screening for homogeneity of within-group regression coefficients. A $p \leq 0.05$ was considered statistically significant.

B. RESULTS

1. Characteristics of the Alcoholic and Nonalcoholic Fathers

The assignment of children to the three groups was based a priori on the father's drinking behavior. The SAA group had fathers who were nonabstaining alcoholics, the SRA group had fathers who were recovered alcoholics (4.43±0.59 years of abstinence), and the SSD group had fathers who were not alcoholic but who drank alcohol socially. The alcoholic fathers of these children, besides being differentiated on their ability or inability to abstain, showed the following characteristics. Fathers of the SAA group compared with fathers of the SRA group were slightly younger (42.6±1.0 vs. 44.7±1.1 years of age) and had a lower annual income ($50,700±9,000 vs. $58,300±6,000). They also began to consume alcohol earlier in their lives (15.7±0.6 vs. 16.5±0.5 years), were more frequently drug dependent (40.6% vs. 25.0), and had more first-degree alcoholic relatives (1.83±0.26 vs. 1.26±0.16). None of these differences achieved statistical significance.

However, fathers of the SAA group compared with fathers of the SRA group had a significantly greater number of medical, legal, and social problems associated with their drinking (0.88±0.15 vs. 0.47±0.11, p=0.03).

Fathers of the SSD group were 46.9±1.1 years old, had an annual income of $73,600±6,800 and began to consume alcohol when they were 19.1±0.5 years of age. Fathers of the SSD group were significantly older than fathers of the SAA group but not older than fathers of the SRA group (p[2,95] =3.85, p=0.02). They began to consume alcohol at a significantly later age than either fathers of the SRA or SAA groups (p[2,95]=10.50, p=0.0001). However, the three groups of fathers did not significantly differ on income. None of the fathers of the SSD group had a history of drug dependence or problems associated with their drinking or had any alcoholic relatives.

2. DRD2 Genotypes of the Children

Table 17 presents TaqI A DRD2 genotypes of the children in the SAA, SRA, and SSD groups. In the SAA group, A1 allele frequency was 0.313 compared with 0.139 and 0.133 in the SRA and SSD groups, respectively. A significant difference in A1 allele frequency was found among these three groups ($\chi^2$=8.56, p=0.01). Further, while the frequency of the A1 allele was very similar in the SRA and SSD groups, the frequency of this allele in the SAA group was significantly higher when compared with either the SRA group $\chi^2$=5.94, p=0.02) or with the SSD group ($\chi^2$=5.69, p=0.02).

TABLE 17

TaqI A DRD2 GENOTYPES AND ALLELIC FREQUENCY IN SONS OF
ACTIVE ALCOHOLIC, RECOVERED ALCOHOLIC,
AND SOCIAL DRINKING FATHERS

| GROUP (n) | No. WITH GENOTYPE | | | ALLELIC FREQUENCY | | SIGNIFICANCE |
|---|---|---|---|---|---|---|
| | A1/A1 | A1/A2 | A2/A2 | A1 | A2 | |
| SAA (32) . . . | 3 | 14 | 15 | .313 | .687 | $\underline{X}^2 = 8.56; p = .01$ |
| SRA (36) . . . | 1 | 8 | 27 | .139 | .861 | |
| SSD (30) . . . | 0 | 8 | 22 | .133 | .867 | |

SAA = Sons of active alcoholic fathers
SRA = Sons of recovering alcoholic fathers
SSD = Sons of social drinking fathers 3. Age, Education Level, and IQ of the Children The relationship of age, education level, and IQ to TaqI A DRD2 alleles in the three groups of boys is shown in Table 18. No significant differences in age and educational level were found among boys carrying the A1 or A2 allele or among the different groups (SAA, SRA, and SSD). There were also no significant interaction effects between allele (A1 and A2) and group (SAA, SRA, and SSD) on these two variables. There was a significant difference in IQ among the three groups of boys (F[2,92]=3.42, p=0.04). However, there was no significant difference in IQ among boys of different allele types and no significant interaction between allele and group on this variable.

was most prominent at $P_z$; subsequently for this initial study, analyses were confined to this site.

Table 19 presents the adjusted means for target P3 amplitudes and latencies at $P_z$ of A1 and A2 allele subjects for each of the three groups of boys. An allele X group (2×3) ANCOVA was conducted on P3 amplitude. Age, IQ, and CPT type were treated as covariates because (a) age has been previously shown to affect P3 characteristics (Chourchesne 1984), (b) there were significant differences in IQ among the three groups, and (c) two types of CPT were used. ANCOVA results showed that there were no significant main effects of allele (A1=29.8±1.2 μV, A2=28.2±0.9 μV; p =0.28) or group (SAA=27.1±1.2 μV, SRA=29.3±1.3 μV, SSD=30.6±1.4 μV;

TABLE 18

RELATIONSHIP OF AGE, EDUCATION LEVEL, AND IQ TO TaqI A DRD2 ALLELES IN SONS
OF ACTIVE ALCOHOLIC, RECOVERED ALCOHOLIC, AND SOCIAL DRINKING FATHERS

| MEASURE (mean) | SAA | | SRA | | SSD | |
|---|---|---|---|---|---|---|
| | A1 (n = 17) | A2 (n = 15) | A1 (n = 9) | A2 (n = 27) | A1 (n =-8) | A2 (n = 22) |
| Age in years (12.5 ± 0.1) . . . | 12.4 ± 0.3 | 12.5 ± 0.3 | 12.9 ± 0.4 | 12.1 ± 0.2 | 12.5 ± 0.4 | 12.8 ± 0.2 |
| Education level (5.5 ± 0.1) . . . | 5.3 ± 0.3 | 5.6 ± 0.4 | 6.1 ± 0.4 | 5.0 ± 0.3 | 6.1 ± 0.6 | 5.8 ± 0.2 |
| IQ (112.5 ± 1.3) . . . | 105.8 ± 2.7 | 111.7 ± 3.2 | 119.2 ± 5.6 | 111.6 ± 2.3 | 119.0 ± 4.8 | 114.3 ± 2.3 |

NOTE-A1 allele includes A1/A2 and A1/A1 genotypes. A2 allele includes A2/A2 genotype only. Values represent mean ± SEM.

4. ERP Profiles of the Children

The grand mean ERP responses of the total number of boys with A1 and A2 alleles were recorded from $F_z$, $C_z$, $P_z$, 01, and 02 electrode sites. The results demonstrated that P3 p=0.18) and no interaction between allele and group (p=0.13). None of the three covariates were significantly related to P3 amplitude.

TABLE 19

RELATIONSHIP OF TARGET P300 AMPLITUDE, LATENCY AT $P_z$,
PERCENT CORRECT RESPONSES, AND RESPONSE TIME TO TaqI A DRD2
ALLELES IN SONS OF ACTIVE ALCOHOLIC, RECOVERED ALCOHOLIC,
AND SOCIAL DRINKING FATHERS

| GROUP | AMPLITUDE (μV) | | LATENCY (msec) | | % CORRECT RESPONSES | | RESPONSE TIME (msec) | |
|---|---|---|---|---|---|---|---|---|
| | A1 | A2 | A1 | A2 | A1 | A2 | A1 | A2 |
| SAA[a] . . . | 26.3 ± 1.7 | 27.9 ± 1.8 | 437 ± 15 | 382 ± 17 | 88.2 ± 2.2 | 86.4 ± 2.3 | 658 ± 26 | 580 ± 27 |
| SRA[b] . . . | 32.2 ± 2.3 | 26.4 ± 1.3 | 468 ± 12 | 422 ± 12 | 90.8 ± 3.0 | 91.1 ± 1.6 | 660 ± 35 | 663 ± 19 |

TABLE 19-continued

RELATIONSHIP OF TARGET P300 AMPLITUDE, LATENCY AT $P_z$, PERCENT CORRECT RESPONSES, AND RESPONSE TIME TO TaqI A DRD2 ALLELES IN SONS OF ACTIVE ALCOHOLIC, RECOVERED ALCOHOLIC, AND SOCIAL DRINKING FATHERS

| GROUP | AMPLITUDE (μV) | | LATENCY (msec) | | % CORRECT RESPONSES | | RESPONSE TIME (msec) | |
|---|---|---|---|---|---|---|---|---|
| | A1 | A2 | A1 | A2 | A1 | A2 | A1 | A2 |
| SSD[c] ... | 31.0 ± 2.5 | 30.2 ± 1.5 | 460 ± 23 | 432 ± 14 | 91.2 ± 2.8 | 91.2 ± 1.9 | 621 ± 34 | 653 ± 23 |
| Mean[d] ... | 29.8 ± 1.2 | 28.2 ± 0.9 | 455 ± 12 | 412 ± 8 | 90.1 ± 1.5 | 89.6 ± 1.1 | 646 ± 18 | 632 ± 13 |

NOTE-A1 allele includes A1/A2 and A1/A1 genotypes; A2 allele includes A2/A2 genotype only. Values represent ANCOVA adjusted mean ± SEM (see text).
[a]N = 32; A1 = 17; A1 = 15.
[b]N = 36; A1 = 9' A2 = 27.
[c]N = 30; A1 = 8; A2 = 22.
[d]N = 98; A1 = 34; A2 = 64.
SAA = Sons of active alcoholic fathers
SRA = Sons of recovering alcoholic fathers
SSD = Sons of social drinking fathers In contrast, allele X group (2×3) ANCOVA results of P3 latency showed a large main effect of allele (A1=455 ±12 ms, A2 =412±8 ms; p=0.004) and a suggestive effect of groups (SAA=409±11 ms, SRA=445±12, SSD=446±13; p=0.059). Whereas Pe latency difference between A1 and A2 allele subjects was greater in the SAA (55 ms) and SRA (46 ms) groups than in the SSD (28 ms) groups, there was no significant interaction between allele and group (p=0.74). The covariate IQ, but not age or CPT type, was significantly and positively related to P3 latency (p=0.01).

In sum, after correcting for variations associated with age, IQ, and CPT type, neither allele nor group had a significant effect on P3 amplitude. However, the presence of the A1 allele was significantly associated with prolonged P3 latency across the three groups, and sons of active alcoholics tended to have reduced P3 latency, regardless of genotype.

5. Accuracy and Reaction Times of the Children to Targets

Table 20 also presents the effects of the variables on the accuracy and RT associated with response to targets on the CPT. Two separate allele X group (2×3) ANCOVAs were conducted on these two behavioral measures. No significant effects of allele (p=0.79), group (p=0.19), or their interaction (p=0.88) were found on the accuracy of target identification, although IQ was found to be significantly and positively related to accuracy (p=0.54), group (p=0.31), or their interaction (p=0.13), nor was it related to any of the three covariates.

In sum, although IQ was related to the accuracy of target identification, after correcting for variations associated with age, IQ, and CPT type, there were no significant effects of allele, group, or their interaction on the behavioral measures of accuracy and RT.

EXAMPLE 6

D₂ DOPAMINE RECEPTOR GENE AND COMPULSIVE OVEREATING

A. METHODS

1. Subjects

Female and male obese subjects were recruited to participate in a long-term dexfenfluramine weight reduction study at the Cathedral Hill Obesity Clinic in San Francisco, Calif. Subjects had to be between 18–65 years of age and in good general physical and mental health. Institutional Review Board approval was obtained for this study, and informed consent was signed by the subjects after the nature of the procedures and maintenance of confidentiality were explained to them.

Inclusion criteria for the present study was a BMI (weight [kg]/height [M]$^2$)≧28.0 for women and men, which is above the recommended National Center for Health Statistics levels (27.3 for women and 27.8 for men) for obesity (National Institutes of Health Consensus Development Panel on the Health Implications of Obesity, 1985). Exclusion criteria were: pregnant or lactating women or women of child-bearing potential who were not using medically accepted means of contraception; obesity of endocrine origin (e.g., Cushing's disorder, Stein-Leventhal, or hypothyroidism syndromes); and history of anorexia nervosa, bulimia, alcoholism, or drug abuse.

At the first visit, to ensure eligibility, subjects were screened with medical history and physical examination, and informed consent was obtained from all the participants. Subjects were weighed in light clothing without shoes to the nearest 0.1 kg and their heights were recorded. Waist circumference was measured at the level of the umbilicus, using a measuring tape with the subject in mid-expiratory position. Hip circumference was recorded over the widest part of the hip region, and the waist-hip ratio (waist/hip× 100) was calculated. After a 5-minute rest, blood pressure (measured with a mercury sphygmomanometer on the right arm) and pulse were determined as part of a general physical examination.

Venous blood was obtained after an overnight fast for routine chemical as well as lipid (cholesterol, high-density lipoprotein [HDL]-and low-density lipoprotein [LDL]-cholesterol, and triglycerides) analysis. A sample of blood (10 ml) in tubes containing ethylenediaminetetraacetic acid (EDTA) was also collected for molecular genetic analysis.

Through interview, history of anorexia nervosa, bulimia, alcoholism, and drug abuse was noted. Furthermore, through administration of questionnaires, family (mother's and father's) history of obesity, the participants' onset of obesity (childhood [before puberty], adolescent [after puberty], and adulthood [after age 18]), and their food preference (carbohydrates, proteins, fats, or foods in general) were also obtained. Food preference was further validated by personal interview with each patient wherein the three categories of foods (carbohydrates, proteins, and fats) and examples of types of each (e.g., carbohydrates: sweets and starches) were clearly delineated. The fourth choice, food in general, was indicated if the patient liked all three food categories.

2. DNA Analysis

Genomic DNA was extracted from the blood sample (Old, 1986) and subsequently used as template for the polymerase chain reaction (PCR™) (Saiki et al., 1988). The primers 5014 and 971 were used to amplify a 310 bp fragment spanning the polymorphic TaqI A site of the DRD2 gene (Grandy et al., 1989a). The sequence for the 5014 primer was 5'-CCgtcgaCCCTTCCTGAGTGTCATCA-3'(SEQ ID NO:1) and for the 971 primer was 5'-CCgtcgaCGGCTGGC-CAAGTTGTCTA-3'(SEQ ID NO:2) (lowercase letters code for SalI site). The primer sequences were synthesized by Oligos Etc. Inc. (Wilsonville, Oreg.).

Amplification was carried out in 100-µl reactions using 1 µg of genomic DNA and 2.5 units of AmpliTaq™ DNA polymerase (Perkin Elmer) in a standard reaction cocktail containing 200 µM of each of the four dNTPs, 1.5 mM $MgCl_2$, and the recommended buffer provided by the manufacturer (Perkin Elmer). After an initial denaturation step at 94° C. for 5 min, DNA was amplified in three-step cycles as follows: denaturation at 94° for 30 sec, annealing at 58° C. for 30 sec, and extension at 72° C. for 30 sec using the Perking Elmer GeneAmp™ 9600 thermocycler. After 35 cycles, a final extension step at 72° C. for 5 min was used.

Figure 6:
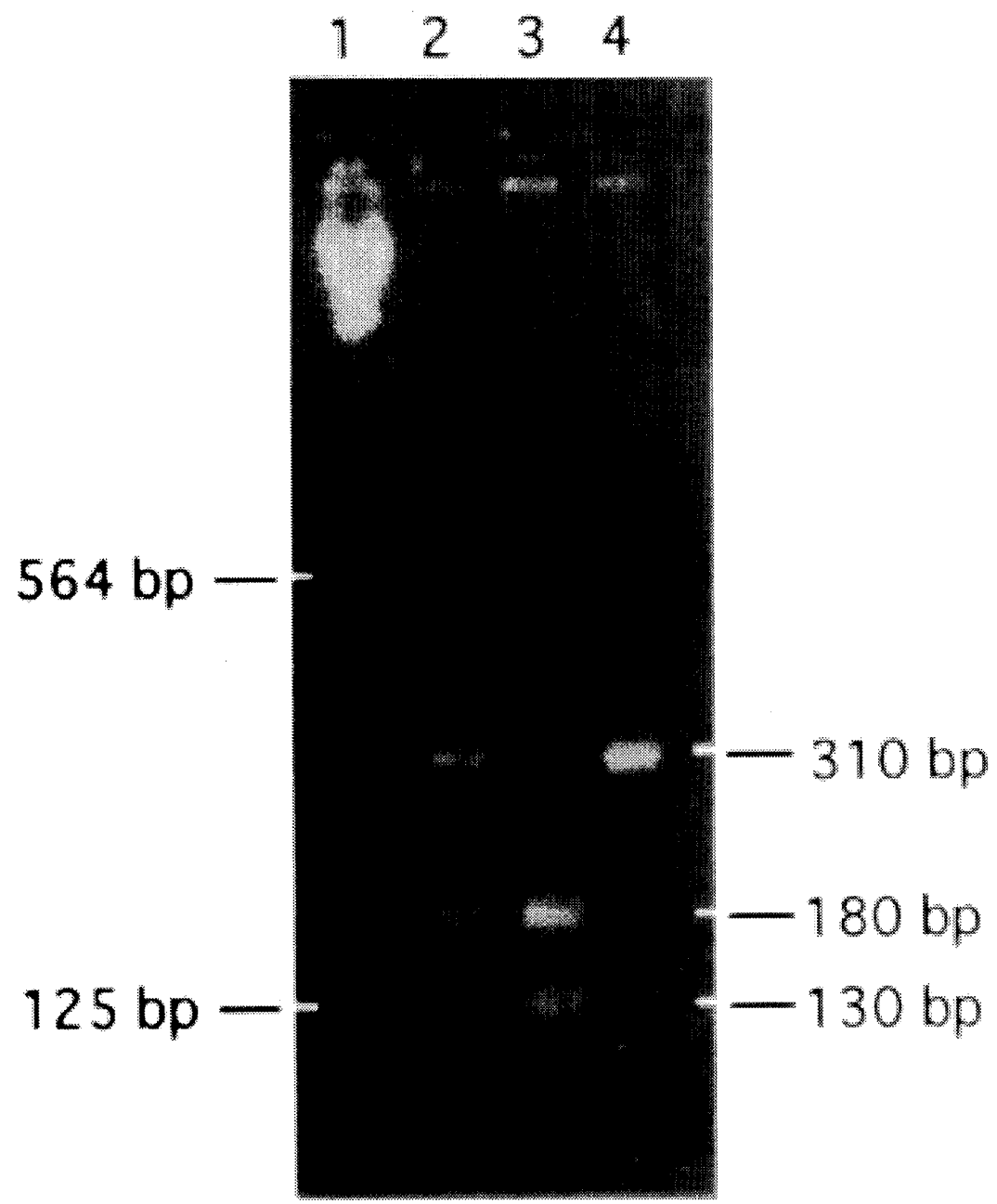
FIG. 6. Identification of $D_2$ dopamine receptor mutation by allele-specific PCR™. Lane 1, size marker (DNA cleaved with the restriction enzyme HindIII); lane 2, A1/A2 genotype (310 bp, 180 bp, 130 bp); lane 3, A2/A2 genotype (180 bp, 130 bp); lane 4, A1/A1 genotype (310 bp).

A 10-µl aliquot was removed and analyzed by gel electrophoresis in a 2.5% agarose gel containing ethidium bromide and visualized under ultraviolet (UV) light. The expected 310 bp fragments were visualized with minimal background. Approximately 500 ng of the DNA was digested with 5 units of TaqI restrictions enzyme (Boehringer-Mannheim Biochemical) At 65° C. for 2 hr. The resulting products were analyzed by agarose gel electrophoresis as before. Allelic data were obtained on all but one subject (no PCR™ product). The A1/A2 genotype is indicated by two fragments: 180 bp and 130 bp; and the A1/A1 genotype is shown by the uncleaved 310 fragment (FIG. 6).

3. Statistical Analysis

Demographic, clinical laboratory, interview, and questionnaire data were coded and entered into a computer data base. DRD2 allelic prevalence, obtained by personnel blinded to the aforementioned information, was also coded and the two data sets were merged for analyses. t tests were used to compare interval data, and chi-square statistic with Yates' correction for continuity (Siegel, 1956), as appropriate, was used for group comparisons of ordinal and nominal values. A Chi-square linear trend analysis (Chochran, 1954) was used to test if increasing risk factors for obesity are associated with A1 allelic prevalence. A two-tailed p value of 0.05 was considered statistically significant.

B. RESULTS

Of a total of 80 patients who volunteered for the study, 7 were excluded from analysis: a man with a history of alcoholism, five women with a BMI<28.0, and a subject for whom no PCR™ product was obtained. Parental history of obesity was unknown in 3 subjects, onset of obesity was not available in 1 subject, and food preference data were available in only 47 subjects. The age (mean±SE) of the 73 obese individuals was 37.2±1.2 years. Age of the 33 subjects the $A1^+$allele (A1/A2 and A1/A1 genotypes) was 37.7± 1.6 years, and 36.8±1.9 years for the 40 subjects carrying the $A1^-$allele (A2/A2 genotype). The age difference between $A1^+$and $A1^+$allelic individuals was not significant (p=0.75).

The sample consisted of 57 women and 16 men. Of the 57 women, 24 had the $A1^+$allele, whereas 33 had the $A1^-$allele. Of the 16 men, 9 had the $A1^+$allele, whereas 7 had the $A1^-$allele. The difference in allelic distribution between the sexes, as expected (the DRD2 gene is localized on chromosome 11), was not significant ($\chi^2$=0.52, p=0.47).

The present sample consisted of 42 non-Hispanic Caucasians of European descent, 10 Hispanics, 12 blacks, and 9 others (2 Asians, 2 Native Americans, 2 Filipinos, 2 Samoans, and 1 of mixed race), a distribution that roughly approximates the prevalence of these groups in the United States. Their TaqI A DRD2 genotypes are shown in Table 20. There was no significant difference in A1/A1, A1/A2, and A2/A2 genotypes among the present four groups of obese subjects studied ($\chi^2 \cong 8.50$, p=0.20).

TABLE 20

TagI A $D_2$ DOPAMINE RECEPTOR GENOTYPES IN OBESE SUBJECTS

| GROUP | GENOTYPES | | |
|---|---|---|---|
| | A1/A1 | A1/A2 | A2/A2 |
| Non-Hispanic Caucasian | 2 | 13 | 27 |
| Hispanic (n = 10) | 2 | 3 | 5 |
| Black (n-12) | 1 | 8 | 3 |
| Other (n = 9)[a] | 1 | 3 | 5 |
| Total (n = 73) | 6 | 27 | 40 |

[a]Consisted of 2 Asians, 2 Native Americans, 2 Filipinos, 2 Samoans, and 1 mixed race.

The relationship of 10 cardiovascular risk factors to DRD2 allelic prevalence in the obese subjects is shown in Table 21. None of the measured factors was significantly differentiated by their DRD2 allelic association. However, with the exception of triglyceride levels, all nine other risk factors were slightly worse in the $A1^+$compared with the $A1^{31}$ allelic subjects.

TABLE 21

CARDIOVASCULAR RISK FACTORS IN OBESE SUBJECTS AND THEIR RELATIONSHIP TO TaqI A $D_2$ DOPAMINE RECEPTOR ALLELES

| MEASURE | TOTAL SUBJECTS (n = 73) | A1⁻ SUBJECTS (n = 33) | A1⁻ SUBJECTS (n = 40) | PROBABILITY (TWO-TAIL) |
|---|---|---|---|---|
| Body mass index (kg/m²) | 35.1 ± 0.5 | 35.3 ± 0.8 | 34.9 ± 0.6 | .70 |
| Waist/hip × 100 | 82.2 ± 1.1 | 82.9 ± 1.7 | 81.7 ± 1.5 | .60 |
| Cholesterol (mg/dl) | 198 ± 5 | 202 ± 7 | 194 ± 7.3 | .41 |
| Triglycerides (mg/dl) | 133 ± 8 | 132 ± 11 | 134 ± 12 | .89 |
| HDL-Chol (mg/dl) | 55.2 ± 1.5 | 54.2 ± 2.1 | 56.1 ± 2.2 | .54 |
| LDL Chol (mg/dl) | 120 ± 6 | 121 ± 6 | 119 ± 9 | .80 |
| Cholesterol/HDL-Chol | 3.72 ± 0.12 | 3.90 ± 0.20 | 3.60 ± 0.15 | .25 |

TABLE 21-continued

CARDIOVASCULAR RISK FACTORS IN OBESE SUBJECTS AND THEIR
RELATIONSHIP TO TaqI A $D_2$ DOPAMINE RECEPTOR ALLELES

| MEASURE | TOTAL SUBJECTS (n = 73) | A1⁻ SUBJECTS (n = 33) | A1⁻ SUBJECTS (n = 40) | PROBABILITY (TWO-TAIL) |
|---|---|---|---|---|
| LDL-Chol/HDL-Chol | 2.28 ± 0.13 | 2.36 ± 0.16 | 2.22 ± 0.19 | .60 |
| B.P. systolic (Mm) | 125 ± 2 | 126 ± 2 | 124 ± 2 | .50 |
| B.P. diastolic (mm) | 83.0 ± 1.6 | 84.8 ± 1.5 | 81.6 ± 1.4 | .11 |

Note. Values represent mean ± SE. HDL-Chol = high-density lipoprotein cholesterol; LDL-chol = low-density lipoprotein cholesterol; B.P. = blood pressure.

The BMI of the A2/A2, A1/A2, and A1/A1 genotypes (mean±SE) were: 34.9±0.6 (n=40), 34.8±1.0 (n=27), and 37.5±1.5 (n=6), respectively. The waist-hip ratio of the A2/A2, A1/A2, and A1/A1 genotypes (mean±SE) were 81.7±1.5 (n=40), 82.4±1.9 (n=27), and 85.0±3.7 (n=6), respectively. Although the A1 homozygotes displayed higher values in these two measures compared with the A2 homozygotes and the heterozygotes, the differences between the relatively few A1 homozygotes and the other two genotypes were not statistically significant.

The relationship of DRD2 alleles to parental history of obesity in the present subjects is presented in Table 22. In obese subjects whose fathers and mothers were not obese, 31.0% carried the A1⁺allele. A1⁺allelic prevalence was 43.5% and 51.5% in subjects whose fathers and mothers, respectively, were obese. In subjects whose fathers and/or mothers were obese, 53.7% displayed the A1⁺allele; the difference in A1⁺allelic prevalence between this group and the group with negative parental history of obesity approached but did not achieve statistical significance ($\chi^2$= 2.67, p=0.10).

Table 22 also shows the relationship of DRD2 alleles to the age of onset of obesity. Subjects whose onset of obesity occurred when they were children, adolescents, and adults, respectively, had the following progressive increase in A1⁺ allelic prevalence: 25 0%, 365% and 56.4%, with the A1⁺allelic prevalence being significantly higher ($\chi^2$=4.41, p=0.04) in adult-onset than in child-onset obesity. Moreover, when the relationship of age of obesity onset to A1⁺allelic prevalence was ascertained using the Mantel-Haenszel test for linear association (Cochran, 1954), increasing age of onset was positively and significantly associated to A1⁺allelic classification ($\chi^2$=5.42, p=0.02).

The relationship of food preference of obese subjects to their DRD2 allelic distribution is further shown in Table 22. Comparison made in allelic prevalence between subjects who prefer carbohydrates and subjects who prefer other foods (fats, proteins, or food in general) showed that 64.3% of the carbohydrate preferred carried the A1⁺allele, whereas 21.1% of the subjects who preferred other foods carried this allele ($\chi^2$=6.85, p=0.009).

Figure 7:
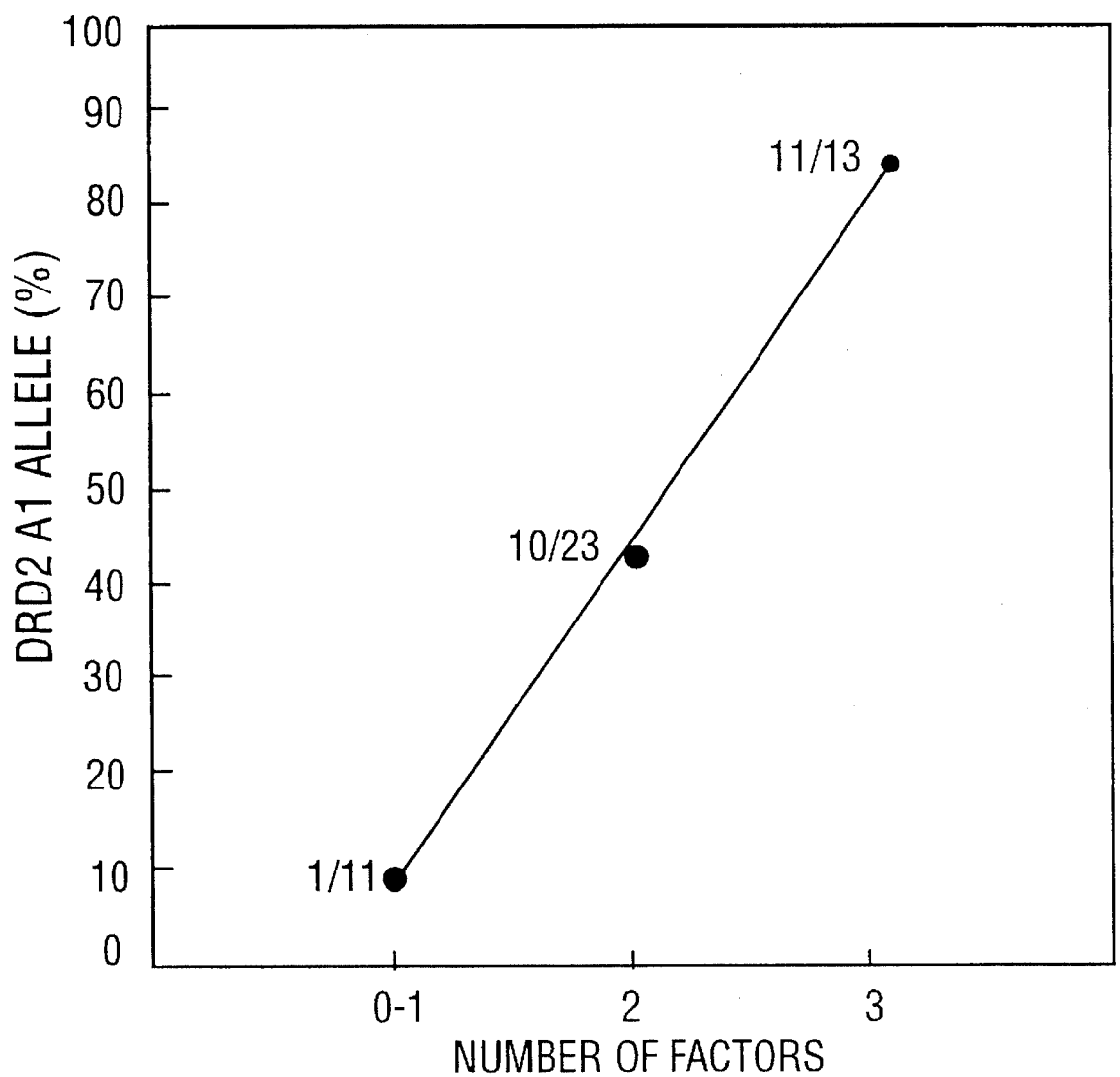
FIG. 7. $D_2$ dopamine receptor A1 allele as a function of phenotypic factors in obese subjects. The factors include: parental history of obesity (presence of a least one obese parent), adolescent- or adult-onset of obesity, and carbohydrate preference. Linear trend analysis shows that increasing factor scores are positively and significantly associated with the prevalence of the $D_2$ dopamine receptor A1 allele ($\chi^2=13.5$, df=1, p=0.0002).

Next, a determination was made of the relationship of the three phenotypic factors shown in Table 22 to A1⁺allelic prevalence. Factor scores on each obese subject were obtained by assigning a score of 1 for the presence of each of the following: parental history of obesity (father and/or mother obese), onset of obesity (adolescent or adult), and food preference (carbohydrate preferred). Thus, scores ranging from 0–3 were obtained depending on the number of these factors present in each subject. Because there were only 2 subjects in the 0-factor group, their allelic data were combined with the subjects in the 1-factor group. A1⁺allelic prevalence in these various factor score categories is shown in FIG. 7. The A1⁺allele contributed to 9.1% in 0–1 factor group, 43.5% in the 2-factor group, and 84.6% in the 3-factor group.

A significant difference in allelic prevalence was found among these three factor groups ($\chi^2$=13.9, p=0.001). Furthermore, when the relationship of factor score to A1⁺allelic prevalence was determined using a linear association test (Cochran, 1954), increasing factor score was positively and significantly related to A1⁺allelic classification ($\chi^2$=13.5, p=0.0002).

TABLE 22

RELATIONSHIP OF TaqI A DRD2 ALLELES TO PARENTAL
HISTORY, ONSET OF OBESITY, AND FOOD PREFERENCE

| BACKGROUND CHARACTERISTICS | A1⁻ | A1⁻ | % A1⁻ | SIGNIFICANCE |
|---|---|---|---|---|
| Parental history of obesity[a] | | | | |
| Neither fathers nor mothers obese | 9 | 20 | 31.0 | — |
| Fathers obese | 10 | 13 | 43.5 | $X^2$ = 0.40, p = .53 |
| Mothers obese | 17 | 16 | 51.5 | $X^2$ = 1.88, p = .17 |
| Fathers and/or mothers obese | 22 | 19 | 53.7 | $X^2$ = 2.67, p = .10 |
| Onset of obesity[b]: Child | 5 | 15 | 25.0 | — |
| Adolescent | 5 | 8 | 36.5 | $X^2$ = 0.19, p = .66 |
| Adult | 22 | 17 | 56.4 | $X^2$ = 4.07, p = .04 |
| Food preference: Carbohydrates | 18 | 10 | 64.3 | — |
| Other[c] | 4 | 15 | 21.1 | $X^2$ = 6.85, p = .009 |

[a]Comparison with neither fathers nor mothers obese. [b]Comparison with child-onset obesity. [c]Other includes proteins, fats, or food in general.

EXAMPLE 7

INCREASED PREVALENCE OF THE TaqI A1 ALLELE OF THE DOPAMINE $D_2$ RECEPTOR GENE IN OBESITY WITH COMORBID POLYSUBSTANCE ABUSE

A. METHODS

1. Subjects

Female and male obese subjects were recruited to participate in this gene study at the PATH Clinic, Princeton, N.J. Subjects had to be between the ages of 18 and 65 years. University of Texas Health Science Center Institutional Review Board approval was obtained for this study, and informed consent was signed by the subjects after the nature of the procedure and maintenance of confidentiality were explained to them.

Inclusion criterion was a body mass index (weight [kg]/height[M]$^2 \geq 28.0$) for women and men which is above the recommended National Center for Health Statistics levels for obesity (27.3 for females and 27.8 for males) (National Institute of Health Consensus Development Panel of the Health Implications of Obesity, 1985).

Exclusion criteria were: non-caucasians and pregnant or lactating women. The abuse of psychoactive drugs and/or alcohol or parental or familial alcoholism were not considered exclusion criteria in the present study. Through interview, history of anorexia nervosa, bulimia, alcoholism, and drug abuse was noted. Furthermore, through administration of questionnaires, family history (mother and father) of alcoholism and drug dependence, and food preference (carbohydrates, proteins, fats, or food in general) were also obtained.

2. Genetic Analyses

For this study, a total of 41 caucasian obese subjects were genotyped for the TaqI A1 alleles of the DRD2 gene. High molecular weight genomic DNA was extracted from whole blood according to the standard procedures. The DNA probe used was a 1.73 kilobase (kb) band obtained from a BamHI digest of a human genomic fragment ihD$_2$G1. The fragment includes, in part, the coding sequence of the last exon containing the seventh transmembrane domain of the DRD2 gene and part of the 16.5 kb of the three flanking sequence.

The 1.73 kb probe was labeled using random-priming with $^{32}$P[dCTP] to a specific activity of $1\times10^9$ counts/min per μg. The DNA samples after digestion with TaqI were hybridized with the labeled probe to reveal the A1 (6.6 kb) and A2 (3.7 kb) alleles. Moreover, for statistical comparison a total of 286 healthy caucasian males and females similarly genotyped derived from the literature were utilized as controls in the present investigation.

3. Statistical Analyses

Demographic, clinical, laboratory, interview, and questionnaire data were coded and entered into a computer data base. DRD2 allelic prevalence, obtained by staff blinded to the aforementioned information, was also coded, and the two data sets were merged for analysis. T-tests were used to compare interval data and Chi-square statistic with Yates' correction for continuity was used for group comparisons of ordinal and nominal values. A Chi-square linear trend analysis was used to test if comorbid polysubstance abuse increased the prevalence of the $D_2$ A1 allele. A two-tailed p value of 0.05 was considered statistically significant.

B. RESULTS

Of a total of 41 obese subjects (see Table 23), the age (mean±SE) was 48.8±1.99 years. Age of the 21 subjects carrying the A1$^+$allele (A1/A2 and A1/A1 genotypes) was 46.62±3.15 years and 47±2.46 years for the remaining 20 probands carrying the A1 allele (A2/A2 genotype).

The age difference between A1$^+$and A1$^{31}$ allelic individuals was not significant (p=0.92). The demographic breakdown included 26 females and 14 males. Of the 26 females, 10 had the A1$^+$ allele, whereas 16 had the A1$^-$allele. Of the 15 males, 11 had the A1$^+$allele, while 4 had the A$^-$allele. The difference in allelic distribution between gender was not significant ($\chi^2$=4.63, p=0.031).

While the BMI of the 41 subjects was 32.45±1.05, the BMI of the A2/A2, A1/A2, and A1/A1 genotypes (mean±S.E.) were 33.15±0.929 (n=20); 32.41±2.25 (n=17); and 29.12±2.02 (n=4); respectively. The differences between these three genotypes with regard to BMI were not statistically significant.

The genotypic distribution of the $D_2$ A1 and $D_2$ A2 alleles in the 286 literature controls, 32 obese subjects without comorbid polysubstance abuse and 10 obese subjects with comorbid polysubstance abuse is presented in Table 23.

TABLE 23

GENOTYPE DISTRIBUTION OF $D_2$ DOPAMINE RECEPTOR GENE IN CONTROLS AND OBESE SUBJECTS WITH AND WITHOUT COMORBID POLYSUBSTANCE ABUSE

| Group | N | % Genotype $D_2$ A1 | % Genotype $D_2$ A2 |
|---|---|---|---|
| Controls | 286 | 19.5 | 80.5 |
| Obese subjects without polysubstance abuse | 32 | 40.6 | 59.4 |
| Obese subjects with polysubstance abuse | 9 | 88.9 | 11.1 |

The $D_2$ A1 allele was present in 19.5% of these subjects compared to 80.5% of $D_2$ A2 carriers in this population. In the 41 obese subjects, the $D_2$ A1 allele was present in 51.22%, whereas the $D_2$ A2 allele was observed in 48.78% of the cases. A Chi-square (Yates) analysis revealed a strong association of the $D_2$ A1 allele in the obese subjects compared to the literature controls ($\chi^2$=33.55, df=1, p=<1×10$^{-7}$;OR=7.29 [+3.41–15.67]).

Figure 8:
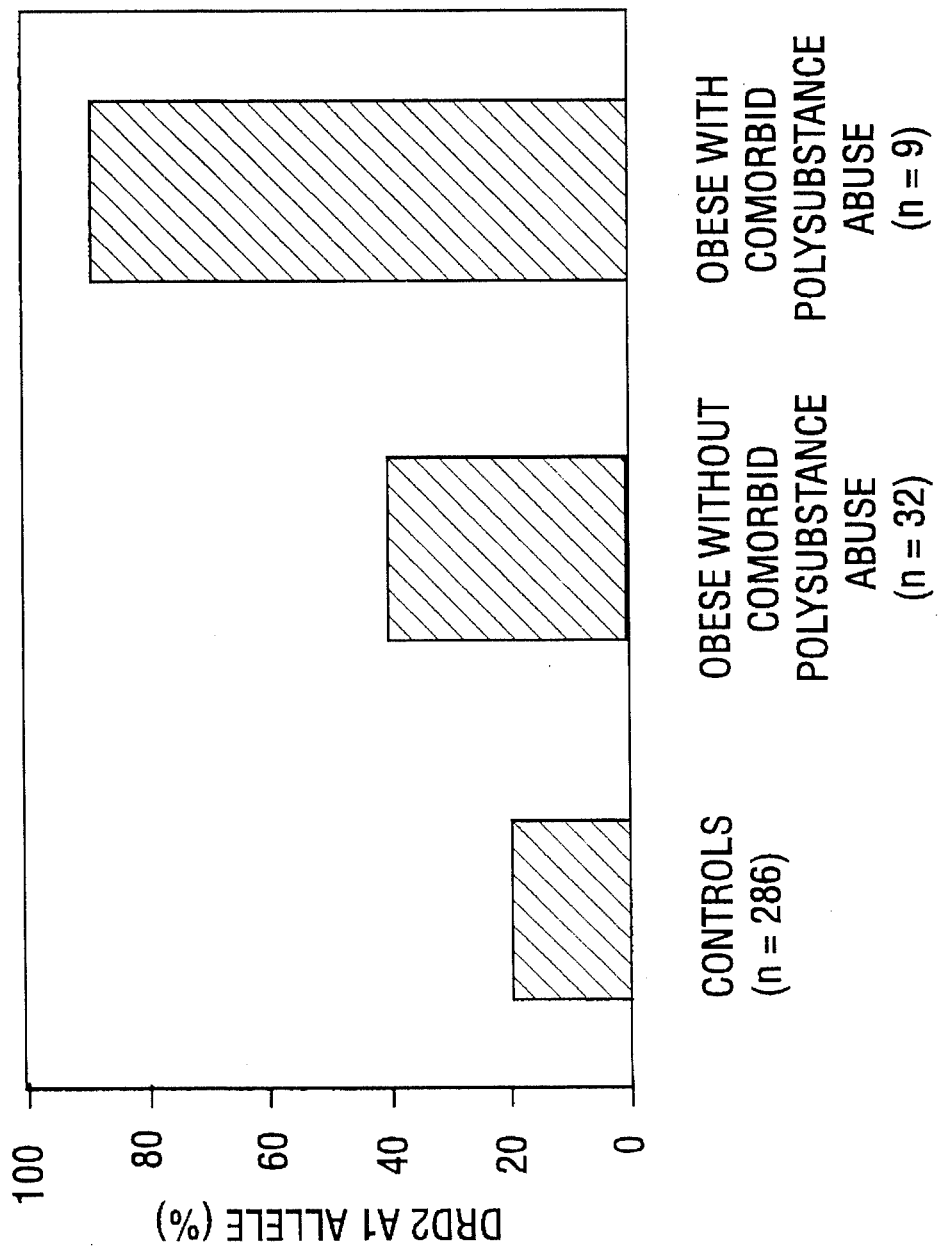
FIG. 8. DRD2 A1 allele as a function of increasing polysubstance in controls and obese subjects. Linear Trend Analysis shows a progressive increase in $A1^+$ allelic prevalence: controls<obese without polysubstance<obese subjects with polysubstance abuse, with the $A1^+$ allelic prevalence being significantly higher in the comorbid polysubstance abusing group. ($\chi^2=47.2$, df=1, p<0.00001).

Furthermore, it was found that in the nine obese subjects possessing comorbid polysubstance abuse, the prevalence of the $D_2$ A1 allele significantly increased compared to obese subjects without comorbid polysubstance abuse ($D_2$ A1%=40.62) Eight out of these nine subjects possessed the $D_2$ A1 allele, or 90% (Yates $\chi^2$=47.76, df=1, p=0.029). Finally, when comparing the 286 controls, 32 obese subjects without comorbid polysubstance abuse, and the nine obese subjects with amorbid polysubstance abuse, it was found the following progressive increase in A1$^+$allelic prevalence: 20.0%, 40.6%, and 88.9% with the A1$^+$allelic prevalence being significantly higher ($\chi^2$=47.22, df=1, p<0.0001) in the comorbid polysubstance abusing group (see FIG. 8).

As previously indicated, there is growing evidence that heredity factors are involved in obesity. Certainly, the present data further confirms an association of the TaqI A1$^+$allele of the DRD2 gene and obesity. These data are in full agreement with others (Comings et al., 1993; Noble et al., 1994), and the finding of increased prevalence of the $D_2$ A1 allele in obese subjects with comorbid polysubstance abuse extends the previous work and further characterizes the general involvement of DRD2 polymorphisms in addictive behaviors. The pathological basis for these molecular genetic findings in obesity is yet unclear.

However, it has been suggested that the apparent relationship between increased expression of overeating and the prevalence of the A1 allele is that either the mutation causing the TaqI A1 polymorphism or a mutation in linkage disequilibrium with the TaqI A1 polymorphism is associated with a decrease in the function of the DRD2 gene (Rajput-Williams et al., 1988). Evidence for such an effect has come from a study (Noble et al., 1991) showing a significant decrease in the number of $D_2$ dopamine receptor binding sites in brains of individuals carrying the A1 allele compared to those that did not.

While the present results must be approached with caution and further studies are required to render a broad generalization of involvement of RFLPs of the DRD2 gene and subsets of obesity, especially when comorbid polysubstance abuse is present, it could suggest that the presence of the $D_2$ A1 allele confirms increased risk for not only obesity but other related addictive behaviors.

EXAMPLE 8

$D_2$ DOPAMINE RECEPTOR GENE AND CIGARETTE SMOKING

A. METHODS

1. Subjects

A sample of 354 Caucasian (non-Hispanic) subjects was recruited from two United States cites: Reno, Nev. (n=286), and Los Angeles, Calif. (n=68). Through the administration of questionnaires, smoking behavior was ascertained. Subjects were considered to be smokers if they had consumed 100 cigarettes or more in their lifetime. In the present sample, 57 were current smokers, and 115 were past smokers and 182 were nonsmokers. Of these subjects, 190 were males and 164 were females.

2. Genetic Analyses

A blood sample was obtained from each subject. Genomic DNA was extracted and subsequently used as a template for the polymerase chain reaction. Two primers were used to amplify a 310 bp fragment spanning the polymorphic TaqI A site of the DRD2 gene (Grandy, et al., 1989a, 1989b). The 310 bp fragment obtained from each subject was digested with TaqI restriction enzyme and the products were separated by agarose gel electrophoresis and visualized with ethidium bromide. Three potential fragments were obtained. The A1/A2 genotype is revealed by three fragments: 310 bp, 180 bp and 130 bp; the A2/A2 genotype is indicated by two fragments: 180 bp and 130 bp: and the A1/A1 genotype is shown by the uncleaved 310 bp fragment.

B. RESULTS

1. Distribution of DRD2 genotypes

The distribution of DRD2 genotypes in the three groups of subjects studied was as follows—current smokers: A1/A1, (n=5); A1/A2, (n=21); and A2/A2, (n=31); past smokers: A1/A1, (n=5); A1/A2, (n=41); and A2/A2, (n=69); nonsmokers: A1/A1, (n=6); A1/A2, (n=45); and A2/A2, (n=131). Allelic distribution was not differentiated either by gender or age in this sample.

2. Presence of the A1 allele

Figure 9:
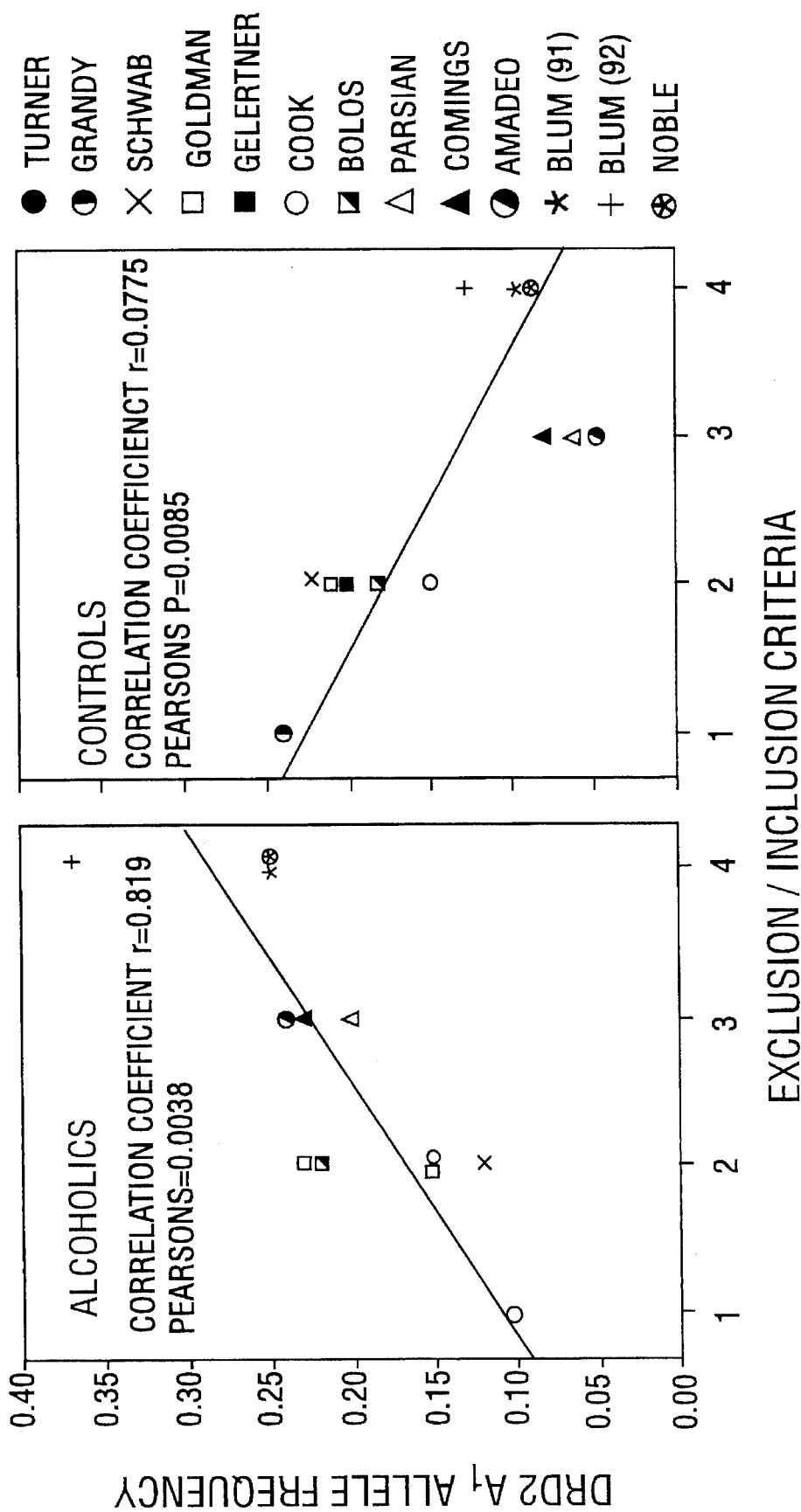
FIG. 9. The ratio of A1 allele (A1/A1 and A1/A2 genotypes) to A2 allele (A2/A2 genotype) in nonsmokers, past smokers and current smokers. *Significantly higher in past smokers compared to nonsmokers ($\chi^2=4.07$, p=0.044, odds ratio=1.71). **Significantly higher in current smokers compared to nonsmokers ($\chi^2=5.37$, p=0.021, odds ratio=2.15). Smokers (past and current combined) had a significantly higher prevalence of the A1 allele than nonsmokers ($\chi^2=6.87$, p=0.009, odds ratio=1.85).

FIG. 9 shows the ratio of the presence of the A1 allele (A1/A1+A1/A2 genotypes) to the absence of this allele (A2/A2 genotype) in current and past smokers and in nonsmokers. Analysis of the data showed that DRD2 allelic prevalence was different among these three groups ($\chi^2$=8.00, df=2, p=0.018). Specifically, the A1 allele occurred in a larger proportion of current smokers compared to nonsmokers ($\chi^2$=5.37, p=0.021, odds ratio=2.15). The incidence of the A1 allele was also higher in past smokers compared to nonsmokers ($\chi^2$=4.07, p=0.044, odds ratio=1.71).

Furthermore, smokers (past and current combined) had a significantly higher incidence of the A1 allele compared to nonsmokers ($\chi^2$=6.87, p=0.009, odds ratio=1.85). Linear trend analysis (Cochran, 1954) of A1 allelic incidence in the nonsmoker, past smoker and current smoker groups respectively showed that as smoking severity increased, so did the incidence of the A1 allele ($\chi^2$=7.69, df=1, p=0.006).

EXAMPLE 9

THE $D_2$ DOPAMINE RECEPTOR GENE AS A PREDICTOR OF REWARD DEFICIENCY SYNDROME: BAYES' THEOREM

A. RESULTS

1. Bayes' Theorem As A Predictive Model

Bayes' Theorem is standard in the field of medicine to predict the likelihood that a particular event (defect) such as possessing the TaqI A1 allele of the DRD2 gene will result in an another event (disorder) such as having abnormal drug and alcohol seeking behavior. Table 3 includes the predictive value of addictive behavioral prevalence in carriers of the A1 allele of the DRD2 gene utilizing Bayes' Theorem.

According to Bayes' rule, the predictive value positive(PV+) of a screening test is the probability that a person has disorder, given that the test is positive:

Pr(disorder/test$^+$)

The predictive value negative (PV–) of a screening test is the probability that a person does not have disorder given that the test is negative:

Pr(no disorder/test$^-$)

In this mathematical model, the sensitivity of a symptom (or set of symptoms or screening test) is the probability that the symptom is present given that the person has disorder. The specificity of a symptom (or set of symptoms or screening test) is the probability that the symptom is not present given that a person does not have disorder. A false negative is defined as a person who tests out negative but who is actually positive. A false positive is defined as a person who tests out as a positive but who is actually negative.

In order to calculate Bayes' theorem the following formula was used:

$$\text{predictive value} = \frac{(\text{prevalence})(\text{sensitivity})}{(\text{prevalence})(\text{sensitivity})(1-\text{prevalence})(1-\text{specificity})}$$

To calculate the specificity, very well-characterized accessed controls were screened for alcohol, drug and tobacco use (in some samples [see Table 24]). To date no study has carefully utilized rigid exclusion criterion to assess controls. Moreover, to calculate the sensitivity of alcoholism, cocaine dependence, polysubstance abuse, smoking, overeating, ADHD, Tourette's Syndrome and pathological gambling, proband genotyping was used from studies where the probands were characterized for chronicity or severity of the disorder (see Table 24).

The predictive value of a positive test result is defined as the percentage of positive result that are true positives when the test is applied to a population containing both healthy and disordered subjects (Galen and Gambino, 1975). Common sense would suggest that the predictive value of a test is dependent on the positivity of the test in disorder and its negativity in health (Uhl et al., 1993). With this in mind, interpretation of these data suggest that a positive result from the TaqI A1 allelic genotype is very predictive, since it was found that $PV^+ = 0.744$ or 74%. However, a negative result from the TaqI A1 genotype is not predicted, since it was found that $PV^- = 0.548$ or 54.8%. It is noteworthy that the low negative predictive value is due to the lack of specificity since control assessment for all exact studies have not utilized rigid inclusion/exclusion criterion and is quite heterogeneous. As a number of related impulsive-addictive-impulsive behaviors are excluded in controls and the prevalence of IACD is more accurately defined, the negative predictive value will significantly increase.

Figure 10:
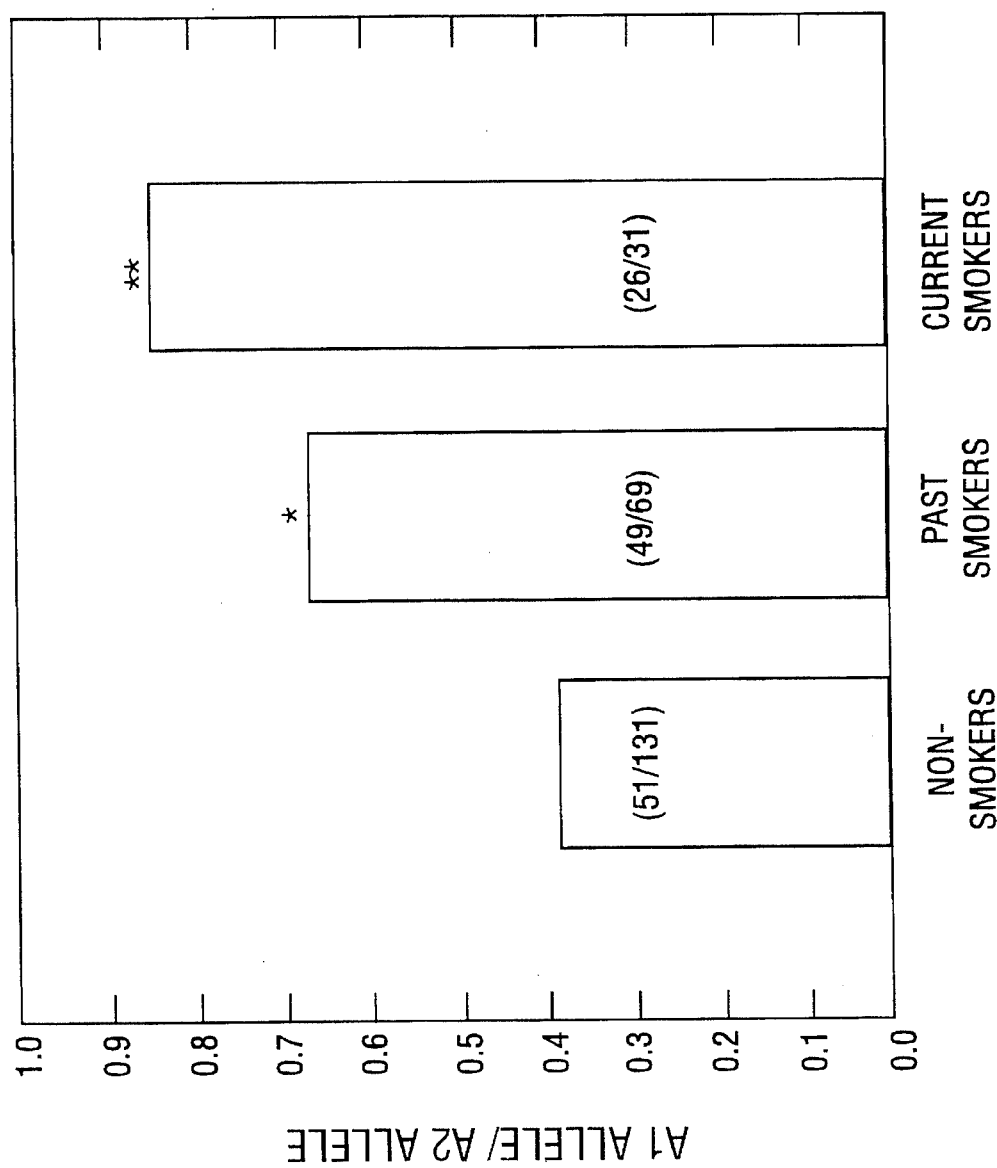
FIG. 10. DRD2 TaqI A1 allele frequency as a function of inclusion/exclusion criteria in both alcoholics and controls. (These data are derived from: Blum, et al., 1990; Blum and Payne, 1991; Bolos, et al., 1990; Gelernter, et al., 1991; Comings, et al., 1991; Parsian, et al., 1991; Cook, et al., 1992; Schwab, et al., 1991; Goldman, et al., 1992; Grandy, et al., 1989b; Noble, et al., 1993a; Amadeo, et al., 1993; and Turner, et al., 1992).

Finally, an analysis of the pooled data utilizing the above referenced studies (see Table 3) related to RDS or IACD resulted in an odds ratio of 3.53 (95% confidence limits [2.56–4.87]) with a p value less than 0.01 indicating a similarly strong positive correlation of the DRD2 gene variant and this disorder (Yates $\chi^2 = 68.38$, df=1, $p<1\times10^{-7}$). A graphical summary of the relationship between DRD2 A1 allele frequency and inclusion/exclusion criteria in various studies involving alcoholics shows a dramatic difference when compared to control subjects (FIG. 10).

2. DNA Testing To Predict High Risk

Utilizing logistic regression modeling, especially in the case of cocaine dependent probands, the prevalence of the variants of the DRD2 gene increased with at least three behavioral risk factors: parental alcoholism; utilization of potent drug forms; early deviant behavior (Noble et al., 1993). Specifically, the prevalence of the A1 allele in individuals carrying the three risk factors was observed in seven out of eight probands or 87%. A similar pattern of high risk factors in terms of prevalence of the A1 allele in obesity was observed and included parental obesity, adolescent- or adult-onset of obesity and carbohydrate bingeing (Noble, 1993). Specifically, the prevalence of the A1 allele in those probands carrying these three risk factors was observed in eleven out of thirteen obese subjects or 85%. Moreover, co-morbid substance abuse with obesity yields a $D_2$ A1 allelic prevalence of 88.9% (Blum et al., 1994).

in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following literature citations as well as those cited above are incorporated in pertinent part by reference herein for the reasons cited in the above text.

Abraham, H. D., and Duffy, F. H. (1991). Computed EEG abnormalities in panic disorder with and without premorbid drug abuse. *Biol Psychiatry*, 29(7):687–90.

Amadeo, S., Abbar, M., Fourcade, M. L., Waksman, G., Leroux, M. G., Madec, A., Selin, M., Champiat, J-Claude, Brethome, A., Lucclaire, Y., Castelnau, D., Venisse, J-L, Mallet, J. (1993). $D_2$ dopamine receptor gene and alcoholism. *J. Psychiat. Res.*, 27:173–179.

American Psychiatric Association Task Force. (1991). Quantitative electroencephalography: a report on the present state of computerized EEG techniques. *Am. J. Psychiatry*, 148(7):961–4.

Arinami, T., Itokawa, M., Komiyama, T., Mitsushio, H., Mori, H., Mifune, H., Hamaguchi, H., Toru, M. (1993). Association between severity of alcoholism and the A1 Allele of the dopamine $D_2$ receptor gene Taq1 a RFLP in Japanese. *Biol. Psychiatry*, 33:108–114.

Ballenger, J. C., and Post, R. M. (1980). Carbamazepine in manic-depressive illness: a new treatment. *Am. J. Psychiatry*, 137(7):782–90.

Ballenger, J. C., Goodwin, F. K., Major, L. F., Brown, G. L. (1979). Alcohol and central serotonin metabolism in man. *Arch. Gen. Psychiatry.*, 36: 224–227.

Banki, C. (1981). Factors influencing monamine metabolites and tryptophan in patients with alcohol dependence. *J. Neural. Transm.*, 50:98–101.

TABLE 24

ASSOCIATION OF THE A1 ALLELE OF DRD2 WITH ALCOHOLISM IN NINE INDEPENDENT STUDIES OF CAUCASIANS

| Source | Alcoholics[a] | | | Controls[b] | | | Odds Ratio |
|---|---|---|---|---|---|---|---|
| | A1 | A2 | % A1 | A1 | A2 | % A1 | |
| Blum et al., 1990 | 14 | 8 | 63.6 | 4 | 20 | 16.7 | 8.75 |
| Bolos et al., 1990 | 15 | 25 | 37.5 | 38 | 89 | 29.9 | 1.41 |
| Parsian et al., 1991 | 13 | 19 | 40.6 | 3 | 22 | 12.0 | 5.02 |
| Comings et al., 1991 | 44 | 60 | 42.3 | 24 | 84 | 22.2 | 2.57 |
| Gelernter et al., 1991 | 19 | 25 | 43.2 | 24 | 44 | 35.3 | 1.39 |
| Blum et al., 1991 | 42 | 47 | 47.2 | 6 | 25 | 19.4 | 3.72 |
| Turner et al., 1992 | 9 | 38 | 19.1 | — | — | — | — |
| Amadeo et al., 1992 | 21 | 28 | 42.9 | 7 | 36 | 16.3 | 3.86 |
| Noble et al., 1994 | 34 | 30 | 53.1 | 21 | 48 | 30.4 | 2.59 |
| All sources (n = 986) | 211 | 280 | 43.0 | 127 | 368 | 25.7 | 2.18[c] |

[a] Include both less severe and severe alcoholics
[b] Includes both nonalcoholics and subjects drawn from the general population (alcoholics not excluded)
[c] Yates $\chi^2$ corrected for continuity = 32.0, 95% confidence interval = 1.65–2.88, $p < 10^{-7}$. (Noble, 1993).

While the compositions and methods of this invention have been described in terms of preferred embodiments, it will be apparent to those of skill in the art that variations may be applied to the composition, methods and in the steps or Baptist, T., et al. (1987). Long term administration of some antipsychotic drugs increases body weight and feeding in rats. Are $D_2$ dopamine receptors involved? *Pharmacol. Biochem. Behav.*, 27:399–405.

Begleiter, H., and Porjesz, B. (1988). Potential biological markers in individuals at high risk for developing alcoholism (Review). *Alcohol Clin. Exp. Res.*, 12(4):488–93.

Begleiter, H., and Porjesz, B. (1990). Neurological processes in individuals at risk for alcoholism. *Alcohol*, 25(2–3):251–6.

Begleiter, H., et al. (1984). Event-related brain potentials in boys at risk for alcoholism. *Science* 225:1493–1496.

Begleiter, H., Porjesz, B., Rawlings, R., Eckardt, M. (1987). Auditory recovery function and P3 in boys at risk for alcoholism. *Alcohol*, 4:315–322.

Berman, S. M., Whipple, S. C., Fitch, R. J., Noble, E. P. (1993). P3 in young boys as a predictor of adolescent substance use. *Alcohol*, 10:69–76.

Bernad, P. G. (1989). EEG and pesticides. *Clin. Electroencephalogr,* 20(2):9–10.

Blom, J. L., and Anneveldt, M. (1982). An electrode cap tested. *Electroencephalogr. Clin. Neurophysiol.*, 54(5):591–4.

Blom, J. L., and Mechelse, K. (1980). The EEG profile. In Lechner, H., and Aranibar, A., (Eds.). *EEG and Clinical Neurophysiology, Excerpta Medica, Int. Congr. Ser.* 526:338–46, Amsterdam.

Blum, K. (1989). A commentary of neurotransmitter restoration as a common mode of treatment for alcohol, cocaine and opiate abuse. *Integrative Psychiatry* 6:199–204.

Blum, K., and Kozlowski, G. P. (1990). Ethanol and neuromodulator interactions: a cascade model of reward. In Oliat, H., Parvez, S., and Parvez, H., (Eds.). *Progressive Alcohol Research*, pp. 131–147.

Blum, K., and Payne, J. E. (1991). Alcohol and the Addictive Brain. Free Press, New York.

Blum, K., et al. (1972). Synergy of ethanol and putative neurotransmitters: glycine and serine. *Science*, 176(332):292–294.

Blum, K., et al. (1973). Synergy of ethanol and alcohol-like metabolites: tryptophol and 3,4-dihydroxyphenyl-ethanol, *Pharmacology*, 9:294–299.

Blum, K., et al. (1977). Alcohol and opiates: a review of common neurochemical and behavioral mechanisms. In Blum, K., (Ed.) *Alcohol and Opiates: Neurochemical and Behavioral Mechanisms*. Academic Press, New York, p. 203.

Blum, K., et al. (1988). Reduction of both drug hunger and withdrawal against advice rate of cocaine abusers in a 30-day inpatient treatment program by the neuronutrient Tropamine. *Cur. Ther. Res.*, 43(6):1204–1214.

Blum, K., et al. (1989a). Enkephalinase inhibition and precursor amino acid loading improves inpatient treatment of alcohol and polydrug abusers: double-blind placebo-controlled study of the nutritional adjunct SAAVE. *Alcohol*, 5:481–493.

Blum, K., et al. (1989b). Ethanol ingestive behavior as a function of central neurotransmission (Review). *Experientia.*, 45:444–452.

Blum, K., et al. (1990). Allelic association of human dopamine $D_2$ receptor gene in alcoholism. *J. Amer. Med. Assoc.*, 263:2055–2060.

Blum, K., et al. (1991). Association of the A1 Allele of the $D_2$ dopamine receptor gene with severe alcoholism. *Alcohol*, 8:409–416.

Blum, K., et al. (1993). Genetic predisposition in alcoholism: association of the $D_2$ dopamine receptor TaqI B1 RFLP with severe alcoholism. *Alcohol*, 10:59–67.

Blum, K., et al. (1994a). Association between cocaine dependence and polymorphisms of the dopamine $D_2$ receptor gene. (In preparation).

Blum, K., et al. (1994). $DRD_2$ allele and P300 Abnormalities in obesity, *Annu. Meet. Amer. Soc. Hum. Genet.*, Montreal, Canada.

Blum, K., et al. (1994c). Multiple-independent meta-analyses confirm association of RFLPs at the dopamine $D_2$ receptor gene locus and compulsive disorder: review of exant linkage and association studies. (Manuscript submitted).

Blum, K., et al. (1994). Prolonged P300 latency in a neuropsychiatric population with the $D_2$ dopamine receptor A1 allele, *Annu. Meet. Amer. Psych. Electrophys. Assoc.*, Philadelphia, Pa.

Blum, K., et al. (1995). Dopamine $D_2$ receptor gene variants: association and linkage studies. *Pharmacogenetics*, (In press).

Bohman, M., Sigvardsson, S., and Cloninger, C. R. (1981). Maternal inheritance of alcohol abuse: cross-fostering analysis of adopted women. *Archiv. Gen. Psychiat.* 38:965–969.

Boja, J. W., and Kuhar, M. J. (1989). [$^3$H]cocaine binding and inhibition of [$^3$H]dopamine uptake is similar in both rat striatum and nucleus accumbens. *Eur. J. of Pharm.*, 173:215–217.

Bolos, A. M., Dean, M., Lucas-Derse, S., Ramsburg, M., Brown, G. L., and Goldman, D. (1990). Population and pedigree studies reveal a lack of association between the dopamine $D_2$ receptor gene and alcoholism. *JAMA*, 264:3156–3160.

Bond, M. (1986). Defense style questionnaire. In Vaillant, G. E. (Ed.). *Emperical Studies of Ego Mechanisms of Defense*. American Psychiatric Press, Washington, D.C.

Bond, M., Gardner, S. T., Christian, J., and Sigal, J. J. (1983). Empirical study of self-rated defense styles. Arch. Gen. *Psychiatry* 40:333–338.

Bouchard, C., et al. (1988). Inheritance of the amount and distribution of human body fat. *Int. J. Obesity*, 12:205–215.

Bouchard, C., et al. (1990). The response to long-term overfeeding in identical twins. *N. Eng. J. Med.*, 322:1477–1482.

Braverman, E. R. (1987). Pharmacology of acute and chronic amino acid supplementation: clinical implications. In Essman, W. B., (Ed.). *Nutrients and Brain Function*. Karger, Flushing, N.Y., pp. 176–185.

Braverman, E. R. (1990a). Brain electrical activity mapping in treatment resistant schizophrenics. *J. Orthomol. Med.*, 5(1):46–48.

Braverman, E. R. (1990b). Brain mapping: a short guide to interpretation, philosophy and future. *J. Orthomol. Med.*, 5:4.

Braverman, E. R. (1993). Brain electrical activity mapping (BEAM) in patients who commit violent crimes: are bitemporal abnormalities a characteristic? *J. Orthomol. Med.*, 8(3):54–6.

Braverman, E. R., and Blum, K. (1994). Polysubstance abuse exacerbates brain electrophysiological deficits in a psychiatrically-ill population. (Manuscript submitted).

Braverman, E. R., et al. (1990a). A commentary on brain mapping in 60 substance abusers: can the potential for drug abuse be predicted and prevented by treatment? *Cur. Ther. Res.*, 48(4):569–585.

Braverman, E. R., et al. (1990b). Modification of P300 amplitude and other electrophysiological parameters of drug abuse by cranial electrical stimulation. *Cur. Ther. Res.*, 48:586–596.

Braverman, E. R., et al. (1994) P300 (P3) abnormalities in obesity. American Psychiatric Electroencephalographic Association, Philadelphia, Pa. (Manuscript submitted).

Bray, G. A. (1981). The inheritance of corpulence. In Cioffi, L. A., Jaes, W. P. T., and Van Italie, T. B. (Eds.), *The body weight regulatory system: normal and disturbed mechanisms*. Raven Press, New York, pp. 61–64

Bray, G. A., et al. (Eds.) (1990). Obesity: towards a molecular approach. UCLA symposium on molecular and cellular biology (New Series, Vol.132). Wiley-Liss, New York.

Brazell, M. P., et al. (1990). Acute administration of nicotine increases the in vivo extracellular levels of dopamine, 3,4-dihydroxyphenylacetic acid and ascorbic acid preferentially in the nucleus accumbens of the rat: Comparison with caudate-putamen. *Neuropsychopharmacology*, 29:1177–1185.

Brown, W., et al. (1983). Exponential electrophysiological aging: P300 latency. *Electroencephalogr. Clin. Neurophysiol.*, 55:277–285.

Bunzow, J. R., et al. (1988). Cloning and expression of a rat $D_2$ dopamine receptor cDNA. *Nature* (London), 336:783–787.

Buschbaum, M., and Wender, P. (1973). Average evoked responses in normal and minimally brain dysfunctioned children treated with amphetamine. *Arch. Gen. Psychiatry*, 29(6):764–70.

Cadaviera, F., et al. (1991). Multimodality exploration of event-related potentials in chronic alcoholics. *Alcohol Clin. Exp. Res.*, 15(4):607–11.

Caffey, E. M., Jr. (1961). Experiences with large scale interhospital cooperative research in chemotherapy. *Amer. J. Psychiatry*, 117:713–719.

Carenzie, A., et al. (1980) On the enzymatic degradation of enkephalins: pharmacological implications. In Costa, E., and Trabucci, M., (Eds.). *Neural Peptides and Neural Communication*. Raven Press, New York, pp. 237–246.

Christensen, L., et al. (1991). Dietary alteration of somatic symptoms and regional brain electrical activity. *Biol. Psychiatry*, 29(7):679–892.

Christian, J. C., et al. (1994). Associations of dopamine $D_2$ polymorphisms with brain electrophysiology. *Alcoholism*, 18(2):178.

Chu, N. S. (1979). Carbamazepine: prevention of alcohol withdrawal seizures. *Neurology*, 29(10):1397–1407.

Ciesielski, K. T., et al. (1985). Long term impairment in chronic alcoholics: N2-P3 cognitive potentials in a template-matching memory task. *Alcohol Alcohol.*, 20:402–408.

Clark, P. B. S., and Pert, A. (1985). *Brain Res.*, 348:355–358.

Clark, P. B. S. (1949) In CIBA Foundation Symposium. The biology of nicotine dependence. John Wiley and Sons, New York, pp. 153–162.

Cloninger, C. R. (1983). Genetic and environmental factors in the development of alcoholism. *J. Psychiat. Treat. Eval.* 5:487–496.

Cloninger, C. R. (1987). Neurogenetic adaptive mechanisms in alcoholism. *Science*, 236:410–416.

Cloninger, C. R. (1991). $D_2$ dopamine receptor gene is associated but not linked with alcoholism. *JAMA*, 266:1833–1834.

Cochran, W. G. (1954). Some methods for strengthening the common $\chi^2$ test. *Biometrics*, 10:417–451.

Cohen, H. L., et al. (1991). EEG characteristics in males at risk for alcoholism. *Alc. Clin. Exp. Res.*, 15(5):858–861.

Comings, D. E. (1992). The $D_2$ dopamine receptor and Tourette's Syndrome, *JAMA*, 267:652.

Comings, D. E. (1995). The role of the $D_2$ dopamine receptor gene variants in nueropsychiatric disorders. In Blum, K., and Noble, E. P. (Eds): *Handbook of Psychoneurogenetics*. CRC Press, Boca Raton, Fla., (In press).

Comings, D. E., et al. (1991). Dopamine $D_2$ receptor (DRD$_2$) as a major gene in obesity. *Amer. J. Human Genet.*, 51(Suppl):A211.

Comings, D. E., et al. (1991). The dopamine $D_2$ receptor locus as a modifying gene in neuropsychiatric disorders. *JAMA*, 266:1793–1800.

Comings, D. E., et al. (1993). Association between Tourette's syndrome and homozygosity at the dopoamine D3 receptor gene. *Lancet*, 341:906.

Comings, D. E., et al. (1993). The dopamine $D_2$ receptor (DRD2) as a major gene in obesity and height. *Biochem. Med. Metab. Biol.* 50:176–185.

Comings, D. E., et al. (1994). Pathological Gambling: Molecular Genetic Aspects, Presented at 4th International Conference on Gambling and Risk Taking, May 31-June 3, Las Vegas, Nev.

Comings, D. E., et al. (1994). The dopamine $D_2$ receptor gene: a genetic risk factor in polysubstance abuse. Drug Alcohol Depend. (In press).

Commuzzie, A. G., et al. (1993). Segregation analysis of fat mass and fat free mass. *Genet. Epidem.*, 10:340–341.

Conneally, P. M. (1991). Association between the $D_2$ domain receptor gene and alcoholism: A continuing controversy. *Arch. Gen. Psych.*, 48:664–666; Correction, *Arch. Gen. Psych.*, 48:757–759.

Conover, W. J., and Iman, R. (1981). Transformations as a bridge between parametric and nonparametric statistics. *Amer. Stat.*, 35(3) .

Cook, B. L., Wang, Z. W., Crowe, R. R., Hauser, R., and Freimer, M. (1992). Alcoholism and the $D_2$ receptor gene. *Alcohol Clin. Exp. Res.* 4:89–116.

Cook, C. C., et al. (1994). Linkage analysis confirms a genetic effect at the $D_2$ dopamine receptor locus in heavy drinking and alcoholism. *Neuropsychogenetics*, (In press).

Cook, C. C. H., Brett, P., Curtis, D., Holmes, D., and Gurling, H. M. D. (1993). Linkage analysis confirms a genetic effect at the $D_2$ dopamine receptor locus in heavy drinking and alcoholism. *Psych. Genet.*, 3:130.

Cortes, R. (1989). Dopamine receptors in human brain: autoradiographic distribution of $D_1$ and $D_2$ sites in Parkinson syndrome of different etiology. *Brain Res.*, 483:30–38.

Cotton, N. S. (1979). The familial incidence of alcoholism. *J. Stud. Alcohol.* 40:89–96.

Courchesne, E. (1984). Cognitive components of the event-related brain potential: changes associated with development. In Gaillard, A. W. K., and Rite, W. (Eds.). *Tutorials in ERP research: endogeneous components*. North Holland, Amsterdam, pp. 329–344.

Courchesne, E., et al. (1975). Stimulus novelty, task relevance and the visual evoked potential in man. *Electroencephalogr. Clin. Neurophysiol.*, 39:131–143.

Crowe, R. R. (1993). Candidate genes in psychiatry: an epidemiological perspective. *Am. J. Med. Gen. (Neuropsychiatric Genetics)* 48:74–77.

Damsa, G., et al. (1989). Lack of tolerance to nicotine induced dopamine release in the nucleus accumbens. *Eur. J. Pharmacol.*, 168:363–368.

Daniels, E. K., et al. (1988). Patterns of thought disorder associated with right cortical damage, schizophrenia, and mania. *Amer. J. Psychiatry*, 145(8):944–9.

Defrance, J. F., et al. (1994). Enkephalinase-inhibition and precursor amino acid loading enhances attention processing and P300 in healthy humans. *Annu. Meet. Amer. Psych. Electrophys. Assoc.*, Philadelphia, Penn.

deToldeo-Morrell, L., et al. (1991). A 'stress' test for memory dysfunction. Electrophysiological manifestations of early Alzheimer's disorder. *Arch. Neurol.*, 48(6):605–9.

Devor, E. J. (1992). The $D_2$ dopamine receptor and Tourette's syndrome. *JAMA* 267:651–652.

DiChiara, G., and Imperato, A. (1988a). Drugs abused by humans preferentially increase synaptic dopamine concentrations in the mesolimbic system of freely moving rats. *Proc. Natl. Acad. Sci. USA*, 85:5274–5278.

DiChiara, G., and Imperto, A. (1988b). Opposite effects of μ and κ opiate agonists on dopamine release in the nucleus accumbens and in the dorsal caudate of freely moving rats. *J. Pharmacol. Exp. Ther.*, 244:1067–1080.

DiChiara, G., Imperato, A. (1988c). Drugs abused by humans preferentially increase synaptic dopamine concentrations in the mesolimbic system of freely moving rats. *Proc. Natl. Acad. Sci. USA*, 85:5274–5278.

Dinwiddie, S. H., et al. (1992). Psychiatric comorbidity and suicidality among intravenous drug users. *J. Clin. Psychiatry*, 53(10):364–9.

Donchin, E. (1984). Dissociation between electrophysiology and behavior-a disaster or a challenge? In Donchin, E. (Ed.) Cognitive psychophysiology: event-related potentials and the study of cognition. LEA, Hillsdale, N.J., pp. 107–118.

Doss, F. W. (1979). The effects of antipsychotic drugs on body weight: A retrospective review. *J. Clin. Psychiatry*, 40:528/53–530/55.

Duffy, F. H., et al. (1984a). Age-related differences in brain electrical activity of healthy subjects. *Ann. Neurol.*, 16(4):430–8.

Duffy, F. H., et al. (1984b). Brain electrical activity in patients with presenile and senile dementia of the Alzheimer type. *Ann. Neuro.*, 16:439–448.

Dyr, W., et al. (1993). Effects of $D_1$ and $D_2$ dopamine receptor agents on ethanol consumption in the high-alcohol drinking (HAD) line or rats. *Alcohol*, 10:207–212.

Ehlers, C. L., and Schuckit, M. A. (1990). EEG fast frequency activity in the sons of alcoholics. *Biol. Psychiatry*, 27(6):632–41.

Elmasian, R., Neville, H., Woods, D., Schuckit, M., Bloom, F. E. (1982). Event-related brain potentials are different in individuals at high and low risk for developing alcoholism. *Proc. Natl. Acad. Sci.* USA, 79:7900–7903.

Epstein, C.M., et al. (1989). EEG mean frequencies are sensitive indices of phenylalanine effects on normal brain. *Electroencephalogr. Clin. Neurophysiol.*, 72(2):133–9.

Flanagan, S.D., Noble, E.P., Blum, K., MacMurray, J., Comings, D., Ritchie, T., Sheridan, P. J., Lopatin, Go, and Gysin, R. (1992). Evidence for a third physiologically distinct allele at the dopamine $D_2$ receptor locus (DRD2), *Annu. Meet. Amer. Psychopath. Meet.*, New York.

Friedman, D., et al. (1975). The late positive component (P300) and information processing in sentences. *Electroencephalogr. Clin. Neurophysiol.*, 38:255–262.

Friedman, J. M., et al. (1991). Genetic analysis of complex disorders. Molecular mapping of obesity genes in mice and humans. *Ann. N. Y. Acad. Sci.*, 630:100–115.

Fukuda, M., et al. (1992). Shortening of N1 and P3 latencies in event-related potentials observed coincidentally with clinical improvement during nootropic medication in a demented patient: specific effect of nicergoline. *Jpn. J. Psychiatry Neurol.*, 46(4):919–25.

Fumeron, F., et al. (1988). Association of apolipoprotein E4 allele with hypertriglyceridemia in obesity. *Clinical Genetics*, 34, 258–264.

Galen, R. S., and Gambino, R. (1975). Beyond Normality: *The Predictive Value And The Efficiency Of Medical Diagnosis, Wyley Biomedical Publications*, New York.

Garber, H. J., et al. (1989). Clinical use of topographic brain electrical activity mapping in psychiatry. *J. Clin. Psych.*, 50(6):205–11.

Gejman, P. V., Ram, A., Gelernter, J., et al. (1994) No structural mutation in the dopamine $D_2$ receptor gene in alcoholism or schizophrenia: Analysis using denaturing gradient gel electrophoresis. *JAMA*, 271: 204–208.

Gelernter, J., et al. (1993). The A1 allele at the $D_2$ dopamine receptor gene and alcoholism: a reappraisal. *JAMA* 269:1673–1677.

Gelernter, J., et al. (1993). No association between DRD2 dopamine receptor alleles and cocaine abuse. *Ann. Meet., Coil. Prob. Drug Depend.*, San Francisco, Calif.

Gelernter, J., et al. (1991). No association between an allele at the $D_2$ dopamine receptor gene (DRD2) and alcoholism. *JAMA*, 266:1801–1807.

Gelernter, J., et al. (1990). Gilles de la Tourette syndrome is not linked to D2-dopamine receptor. *Arch. Gen. Psychiatry*, 47:1073–1077.

Geller, I., et al. (1972). The effects of low-dose combinations of D-amphetamine and cocaine on experimentally induced conflict in the rat. *Cur. Ther. Res.*, 14(4):220–224.

George, S. R., et al. (1993). Polymorphism of the D4 dopamine receptor alleles in chronic alcoholism, *Biochem. Biophysic. Res. Comm.*, 196:107–114.

Gerez, M., and Tello, A. (1992). Clinical significance of focal topographic changes in the electroencephalogram (EEG) and evoked potentials (EP) of psychiatric patients. *Brain Topogr.*, 5(1):3–10.

Gershon, E. S., and Rieder, R. O. (1992). Major disorders of mind and brain. *Scientific American* 267:126–133.

Goldman, D., Brown, G. L., Albaugh, B., Robin, R., Goodson, S., Trunzo, M., Akhtar, L., Lucas-Derse, S., Long, J., Linnoila, M., and Dean, M. (1993). DRD2 dopamine receptor genotype, linkage disequilibrium, and alcoholism in American indians and other populations. *Alcohol. Clin. Exp. Res.*, 17:199–204.

Goldman, D., Dean, M., Brown, G. L., Bolos, A. M., Tokola, R., Virkkunen, M., and Linnoila, M. (1992). $D_2$ dopamine receptor genotype and cerebrospinal fluid homovanillic acid, 5-hydroxyindoleacetic acid and 3-methoxy-4-hydroxyphenylglycol in alcoholics in Finland and the United States. *Acta Psychiatr.* Scand., 86:351–357.

Gomer, F. E., et al. (1976). Evoked potential correlates of visual item recognition during memory-scanning tasks. *Physiol. Psychol.*, 4:61–65.

Goodin, D., et al. (1978a). Age-related variations in evoked potentials to auditory stimuli in normal human subjects. *Electroencephalogr. Clin. Neurophysiol.*, 44:447–478.

Goodin, D., et al. (1978b). Long latency components of the auditory evoked-potential in dementia. *Brain*, 101:635–648.

Goodwin, D. W., Schulsinger, F., Hermansen, L., Guz, S. B., and Winkur, G. (1973). Alcohol problems in adoptees raised apart from alcoholic biological parents. *Arch. Gen. Psychiat.* 28:238–243.

Gordis, E., Tabakoff, B., Goldman, D., and Berg, K. (1990). Finding the gene(s) for alcoholism. *JAMA*, 263:2094–2095.

Grandy, D. K., et al. (1989a). Cloning of the cDNA and gene for human $D_2$ dopamine receptor. *Proc. Natl. Acad. Sci. USA*, 86:9762–9766.

Grandy, D. K., et al. (1989b). The human dopamine $D_2$ receptor gene is located on chromosome 11 at q22–q23 and identifies a TaqI RFLP. *Am. J. Human Genet.*, 45:778–785.

Green, M., and Krontiris, T. G. (1993). Alleleic variations of reporter gene activation by the HRAS1 minisatellite. *Genomics* 17:429–434.

Halikas, J. A., et al. (1992). Treatment of crack cocaine use with carbamazepine. *Am. J. Drug Alcohol Abuse*, 18(1):45–56.

Halliday, R., et al. (1976). Averaged evoked potential predictors of clinical improvement in hyperactive children treated with methylphenidate: an initial study and replication. *Psychophysiology*, 13(5):429–40.

Hannah, M. C., et al. (1985). Twin concordance for a binary trait. II. Nested analysis of ever-smoking and ex-smoking traits and unnested analysis of a "committed smoking" trait. *Am. J. Hum. Genet.*, 37:153–165.

Hansch, E. C., et al. (1982). Cognition in Parkinson disorder: an event-related potential perspective. *Ann. Neurol.*, 11:599–607.

Harville, D. A. (1977). Maximum likelihood approaches to variance component estimation and to related problem. *J. Am. Stat. Assoc.*, 72:320–338.

Hauge, X. Y., Grandy, D. K., Eubanks, J. H., Evans, G. A., Civelli, O., and Litt, M. (1991). Detection and characterization of additional DNA polymorphisms in the dopamine $D_2$ receptor gene. *Genomics*, 10:527–530.

Heffner, T. G., et al. (1980). Feeding increases dopamine metabolism in the rat brain. *Science*, 208:1168–1170.

Heller, R. F., et al. (1988). Lifestyle factors in monozygotic and dizygotic twins. *Genet. Epidemiol.*, 5:311–321.

Hernandez, L., and Hoebel, G. B. (1988). Feeding and hypothalamic stimulation increase of dopamine turnover in the accumbens. *Physiology and Behavior*, 44:599–606.

Hernandez, L., et al. (1988). Microdialysis in the nucleus accumbens during feeding or drugs of abuse: amphetamine, cocaine, and phencyclidine. In Kalivas, P. W., and Nemeroff, C. B., (Eds.). *The Mesocorticolimbic Dopamine System. Anny, N. Y. Acad. Sci.*, 537:508–511.

Hill, S. Y., Armstrong, J., Steinhauer, S. R., Baughman, T., Zubin, J. (1987). Static ataxia as a psychobiological marker for alcoholism. *Alcoholism* (N.Y.) 11:345–348.

Hill, S. Y., et al. (1988). Event-related potentials as markers for alcoholism risk in high density families. *Alcohol Clin. Exp. Res.*, 12:545–554.

Hill, S. Y., et al. (1990). Event-related potential characteristics in children of alcoholic from high density families. *Alcohol Clin. Exp. Res.*, 14:6–16.

Hill, S. Y., Goodwin, D. W., Cadoret, R., Osterland, C. K., and Doner, S. M. (1975). Association and linkage between alcoholism and eleven serological markers. *J. Stud. Alcohol*, 36:981–992.

Hoebel, B. G. (1985). Brain neurotransmitters in food and drug reward. *Amer. J. Clin. Nutrit.*, 42:1133–1150.

Hoebel, B. G., et al. (1989). Microdialysis studies of brain norepinephrine, serotonin and dopamine release during ingestive behavior. Theoretical and clinical implications. *Ann. N. Y. Acad. Sci.*, 575:171–191.

Holmes, T. H., and Rahe, R. H. (1967). The social readjustment rating scale. *J. Psychosomatic. Res.*, 11(2):213–18.

Howard, L., and Polich, J. (1985). P300 latency and memory span development. *Dev. Psychol.*, 21:283–289.

Hughes, J. R. (1986). Genetics of smoking: a brief review. *Behav. Ther.*, 17:335–345.

Imperato, A., and DiChiara, G. (1986). Preferential stimulation of dopamine release in the nucleus accumbens of freely moving rats by ethanol. *J. Pharm. Exp. Ther.*, 239:219–228.

Imperato, A., et al. (1986). Nicotine preferentially stimulates dopamine release in the limbic system of freely moving rats. *Eur. J. Pharm.*, 132:337–338.

Itil, T. M., et al. (1987). CEEG dynamic brain mapping: a new method to evaluate brain function in different psychological and drug conditions: symposium electric and magnetic activity of the CNS; research and clinical application in aerospace medicine. Advisory Group for Aerospace Research and Development.

Izenwasser, S., et al. (1990). Comparison of the effects of cocaine and other inhibitors of dopamine uptake in rat striatum, nucleus accumbens, olfactory tubercle, and medial prefrontal cortex. *Brain Res.*, 520:303–309.

Jacobson, S. A., et al. (1993). Conventional and quantitative EEG in the diagnosis of delirium among the elderly. *J. Neurol. Neurosurg. Psychiatry*, 56(2):153–8.

Jellinek, E. M. (1960). The disorder concept of alcoholism. Hillhouse, New Haven.

Jessor, R., and Jessor, S. L. (1977). Problem behavior and psychosocial development: a longitudinal study of youth. Academic Press, New York.

Johnson, R. Jr., (1993). On the neural generators of the P300 component of the event-related potential. *Psychophysiology*, 30:90–97.

Kalss, D. D., and Sharborough, F. W. (1981). Electroencephalography. In Aronson, E., Auger, R. G., Bastron, J. S., et al., (Eds.). Clinical examination in neurology. Mayo Clinic and Mayo Foundation, 5th Ed. W. B. Saunders, Philadelphia, pp. 278–99.

Karp, R. W. (1992). $D_2$ or not $D_2$. *Alcohol. Clin. Exp. Res.*, 16:786–787.

Karson, C. N., et al. (1987). Computed electroencephalographic activity mapping in schizophrenia. The resting state reconsidered. *Arch. Gen. Psychiatry*, 44:514–517.

Kendler, K. S., Heath, A. C., Neale, M. C., Kessler, R. C., and Eaves, L. T. (1992). A population-based twin study of alcoholism in women. *JAMA*, 268:1882–1887.

Kidd, K. K. (1993). Associations of disorder with genetic markers: Deja vu all over again. *Am. J. Med. Gen.*, (*Neuropsychiatric Genetics*) 48:71–83.

Kirby, A. W., et al. (1986). Cholinergic effects on the visual evoked potential. *Evoked Potential*, 26:296–306.

Knight, R. T., et al. (1989). Contributions of temporal-parietal junction to the human auditory P3. *Brain Res.*, 502:109–116.

Knoll, O., et al. (1984). EEG indicates aluminum load in long term hemodialysis patients. *Trace Elements Med.*, 1:54–58.

Kocher, Greg, (1994). Researcher: Addictions symptoms of larger disease. *Messenger-Enquirer*, Owensboro, Ky., 120(224):1B.

Koeller, D. M., Horowitz, J. A., Casey, J. L., Klausner, R. D., and Harford, J. B. (1991). Translation and the stability of mRNAs encoding the transferrin receptor and c-fos. *Proc. Natl Acad. Sci. USA*, 88:7778–7782.

Koob, G. F. (1992). Drugs of abuse: anatomy, pharmacology and function of reward pathways. *Trends Pharmacol. Sci.*, 13:177–184.

Koob, G. F., and Bloom, F. E. (1988). Cellular and molecular mechanisms of drug dependence. *Science*, 242:715–723.

Koob, G. F., et al. (1987). Neurochemical substrates for opiate reinforcement. In Fisher, S., Raskin, A., Uhlenhuth, E. H., (Eds.). Aspects. Oxford University Press, New York, pp. 80–108.

Kowell, A. (1993) A referring physician's view of neurological assessment. Fifth Annual International PET Conference. McClean, Va.

Krontiris, T. G., Devlin, B., Karp, D. D., Robert, N. J., and Risch, N. (1993). An association between the risk of cancer and mutations in the Hras1 minisatellite locus. *New Eng. J. Med.* 329:517–523.

Krontiris, T. G., DiMartino, N. A., Colb, M., and Parkinson, D. R. (1985). Unique allelic restriction fragments of the human Ha-ras locus in leukocyte and tumor DNAs of cancer patients. *Nature* 313:369–374.

Kugler, C. F., et al. (1992). Visual event-related P300 potentials in early portosystemic encephalopathy. *Gastroenterology*, 103(1):302–10.

Kutas, M., et al. (1977). Augmenting mental chronometry: the P300 as a measure of stimulus evaluation time. *Science*, 197:792–795.

Lake, R. A., Wotton, D., Owen, M. J. (1990). A 3' transcriptional enhancer regulates tissue-specific expression of the $CD_2$ gene. *EMBO J.*, 9:3129–3136.

Lamarine, R. J. (1988). Alcohol abuse among native americans *J. Comm. Health*, 13:143–155.

Laskarzewski, P. M., et al. (1983). Familial obesity and leanness. *Int. J. Obesity*, 7:505–527.

Larkin, C. A., and Mandell, W. (1993). Depression as an antecedent of frequency of intravenous drug use in an urban, nontreatment sample. *Int. J. Addictions*, 28(14):1601–12.

LeMoal, M., Simon, H. (1991). Mesocorticolimbic dopaminergic network: Functional and regulatory roles. *Physiol. Rev.* 71:155–234.

Lester, M. L., et al. (1986). Protective effects of zinc and calcium against heavy metal impairment of children's cognitive function. *Nutrit. Behav.*, 3:145–61.

Levy and Kunitz (1974). *In Indian Drinking: Navajo Practices and Anglo-American Theories*, John Wiley & Sons, New York.

Macdonald, A., and Stunkard, A. J. (1990). *Engl. J. Med.*, 322:1530.

Maier, W., et al. (1993). Alcoholism and panic disorder: co-occurrence and co-transmission in families. *Eur. Arch. Clin. Neuroses*, 243:205–11.

Mangan, G. L., and Golding, J. F. (1984). The psychopharmacology of smoking. Cambridge, N.Y.

Maniatis, T., et al. (1982). Molecular cloning: a laboratory manual, Cold Spring Harbor Press, Cold Spring Harbor, N.Y.

Marascuilo, L. A., and McSweeney, M. Nonparametric and distribution from methods for the social sources. Brooks/Cole Publ. Co., Monterrey, Calif.

Marks, J. (1990). Dissecting the complex disorders, *Science*, 247:1540–1542.

Maurer, K., et al. (1988). Topographic mapping of EEG and auditory evoked P300 in neuropsychopharmacology (topographic pharmaco-EEG and pharmaco-AEP 300). *Pharmacopsychiatry*, 21(6):338–42.

Maurer, K., et al. (1990). P3 topography in psychiatry and psychopharmacology. *Brain Topogr.*, 3(1):79–84.

McBride, N. J., et al. (1993). Densities of dopamine $D_2$ receptors are reduced in CNS regions of alcohol-preferring P rats. *Alcohol*, 10(5):387–90.

McNamara, M. E. (1991). Advances in EEG-based diagnostic technologies. In Stoudemire, A., and Fogel, B. S., (Eds.). *Med. Psych. Practice*. Vol. 1. American Psychiatric Press, Washington, DC pp. 163–89.

Messenheimer, J. A., et al. (1992). Event-related potentials in human immunodeficiency virus infection. *Arch. Neurol.*, 49(4):396–400.

Miller, N. S., and Hoffmann, N. G. (1994). Depression associated with alcohol/other drug addiction. *J. Addic.*, 13(2).

Moises, H. W., Gnnnnnnnnelernter, J., Giuffra, L. A., et al. (1989). Dopamine $D_2$ receptor gene excluded in *Schizophrenia First World Conference on Psychiatric Genetics*, Cambridge, U.K., August 3–5.

Moore, D. D., Marks, A. R., Buckley, D. I., Kapler, G., Payvar, F., Goodman, H. M. (1985). The first intron of the human growth hormone gene contains a binding site for glucocorticoid receptor. *Proc. Natl. Acad. Sci. USA*, 82: 699–702.

Morelli, M., et al. (1990). Quantative autoradiographical analysis of the age-related modulation of central dopamine $D_1$ and $D_2$. *Neuroscience*, 36:403–410.

Morrow, L. A., et al. (1992). Delay in P300 latency in patients with organic solvent exposure. *Arch. Neurol.*, 49(3):315–20.

Morstyn, R., et al. (1983). Altered P300 topography in schizophrenia. *Arch. Gen. Psychiatry*, 40(7):729–34.

Myers, R. D., and Veale, W. L. (1968). Alcohol preference in the rat: reduction following depletion of bran serotonin. *Science*, 160,1469–1471.

Myers, R. M., Fischer, S. G., Lerman, L. S., and Maniatis, T. (1985). Nearly all single base substitutions in DNA fragments joined to a GC-clamp can be detected by denaturing gradient gel electrophoresis. *Nucl. Acids Res.*, 13:3131–3145.

National Institutes of Health Consensus Development Panel on the Health Implications of Obesity. (1985). Health implications of obesity. *Ann. Int. Med.*, 103:1073–1077.

Naylor, J. A., Green, P. M., Rizza, C. R., and Giannelli, U. K. (1992). Factor VIII gene explains all cases of haemophilia A. *Lancet*, 340:1066–1067.

Neiswanger, K., Hill, S. Y., and Kaplan, B. B. (1993). Association between alcoholism and the TaqI A RFLP of the dopamine $D_2$ receptor gene in the absence of linkage. *Psych. Genet.*, 3:130.

Neshige, R., et al. (1988). Auditory long latency event-related potentials in Alzheimer's disorder and multi-infarct dementia. *J. Neurol. Neurosurg. Psychiatry*, 51:1120–1125.

Neshige, R., et al. (1991). Event-related brain potentials as indicators of visual recognition and detection of criminals by their use. *Forensic Sci. Int.*, 51(1):95–103.

Newton, M. P., et al. (1989). Cognitive event-related potentials in multiple sclerosis. *Brain*, 112:1637–1660.

Nobilio, D., et al. (1990). Effect of levo-acetyl-carnitine on P300 potential. *Curt. Ther. Res.*, 47:267–77.

Noble, E. P. (1993a). The $D_2$ dopamine receptor gene: A review of association studies in alcoholism. *Behav. Genetics*, 23:117–127.

Noble, E. P. (1993b). The genetic transmission of alcoholism: implications for prevention. *Drug Alcohol Rev.*, 12:283–290.

Noble, E. P., and Blum, K. (1991). The dopamine $D_2$ receptor gene and alcoholism. *JAMA*, 265:2667.

Noble, E. P., and Blum, K. (1993). Alcohol and the $D_2$ dopamine receptor gene. *JAMA*, 270:1547.

Noble, E. P., et al. (1994) Prolonged P300 latency in children with the $D_2$ dopamine receptor A1 allele. *Am. J. Hum. Genet.* (In press).

Noble, E. P., et al. (1993). Allelic association of the $D_2$ dopamine receptor gene with cocaine dependence. *Drug Alcohol Depend.* 33:271–285.

Noble, E. P., et al. (1991). Allelic association of the $D_2$ dopamine receptor gene with receptor-binding characteristics in alcoholism. *Arch. Gen. Psychiatry*, 48:648–654.

Noble, E. P., et al. (1993). $D_2$ dopamine receptor TaqI A alleles in medically ill alcoholic and non-alcoholic patients. *J. Neurochem.*, 61:Suppl. A.

Noble, E. P., et al. (1994b). $D_2$ dopamine receptor gene and cigarette smoking. *Medic Hypothesis*, 42:257–260.

Noble, E. P., et al. (1994e). $D_2$ dopamine receptor gene and obesity, *Int. J. Eating Disorders*, (In press).

Noble, E. P., Syndulko, K., Fitch, R. J., Ritchie, T., Bohlman, M. C. Guth, P., Sheridan, P. J., Montgomery, A., Heinzmann, C. Sparkes, R. S., and Blum, K. (1994). $D_2$ receptor TaqI A alleles in alcoholic and nonalcoholic patients. *Alcohol Alcohol.*, (In press).

Noldy, N. E., et al. (1990). Quantitative EEG and P300 in cocaine withdrawal. *Brain Topography*, 3(1):262–263.

O'Connor, S., et al. (1986). Correlates of increased risk for alcoholism in young men. *Prog. Neuropsychophamacol. Biol. Psychiatry*, 10:211–218.

O'Donnell, B. F., et al. (1987). Evoked potential changes and neuropsychological performance in Parkinson's disorder. *Biol. Psychol.*, 24:23–37.

O'Hara, B. F., Smith, S. S., Bird, G., Persico, A., Suarez, B., Cutting, G. R., and Uhl, G. R. (1993). Dopamine $D_2$ receptor RFLPs, Haplotypes and their association with substance use in black and caucasian research volunteers. *Hum. Hered.*, 209–218.

Olds, J. (1956). Pleasure centers in the brain. *Scientific American*, 195: 5–116.

Olds, J. M. (1986). Fetal DNA analysis. In Davies, E. K., (Ed.). *Human genetic disorder: a practical approach*. IRL Press, Oxford, pp 1–17.

Papanicolaou, A. C., et al. (1984). Evoked potential correlates of posttraumatic amnesia after closed head injury. *Neurosurgery*, 6:676–678.

Parsian, A., Todd, R. D., Devor, E. J., O'Malley, K. L., Suarez, B. K., Reich, T., Cloninger, C. R. (1991). Alcoholism and alleles of the Human $D_2$ dopamine receptor locus. *Arch. Gen. Psych.*, 48:655–663.

Parsian, A., Todd, R. D., O'Malley, K. L., Suarez, B. K., Cloninger, C. R. (1992). Association and linkage studies of new human dopamine $D_2$ receptor polymorphisms (RFLPS) in alcoholism. *Clin. Neuropharm.*, 15 Suppl 1: Pt B.

Parsons, O. A., et al. (1990). Relationships between neuropsychological test performance and event-related potentials in alcoholic and nonalcoholic samples. *Alcohol Clin. Exp. Res.*, 14(5):746–55.

Pato, C. N., Macciardi, F., Pato, M. T., Verga, M. and Kennedy, J. L. (1993). Review of the putative association of dopamine $D_2$ receptor and alcoholism: a meta analysis. *Am. J. Med. Gen. (Neuropsychiatric Genetics)*, 48: 78–82.

Peniston, E. G., and Kulkosky, P. J. (1989). Alpha-theta brainwave training and beta-endorphin levels in alcoholics. *Alcohol Clin. Exp. Res.*, 13(2):271–9.

Pert, A., and Clark, P. B. S. (1987). *Adv. Behav. Biol.*, 31:169–188.

Pfefferbaum, A., et al. (1979). Event-related potential changes in chronic alcoholics. *Electroencephalogr. Clin. Neurophysiol.*, 47:637–647.

Pfefferbaum, A., et al. (1987). Late event-related potential changes in alcoholics. *Alcohol*, 4:275–281.

Pfefferbaum, A., et al. (1991). Event-related potentials in alcoholic men: P3 amplitude reflects family history but not alcohol consumption. *Alcohol Clin. Exp. Res.*, 15(5):839–50.

Pickens, R. W., Svikis, D. S., McGue, M., Lykken, D. T., Heaton, Heaton, L. L., and Clayton, P. J. (1991). Heterogeneity in the Inheritance of Alcoholism. *Arch. Gen. Psychiatry*, 48:19–28.

Picton, T. W., et al. (1984). The effects of age on human event-related potentials. *Psychophysiology*, 21:312–326.

Plomin, R. (1990). The role of inheritance behavior. *Science*, 248:183–188.

Pockberger, H., et al. (1984). Computer-assisted EEG topography as a tool in the evaluation of actions of psychoactive drugs in patients. *Neuropsychobiology*, 12(2–3):183–7.

Polich, J. (1984). P300 latency reflects personal drinking history. *Psychophysiology*, 21:592–593.

Polich, J. (1986). Normal variation of P300 from auditory stimuli. *Electroencephalogr. Clin. Neurophysiol.*, 21:592–593.

Polich, J. (1988). Event-related brain potentials in individuals at high and low risk for developing alcoholism. *Alcohol Clin. Exp. Res.*, 12:368–373.

Polich, J., and Bloom, F. E. (1987). P300 from normals and adult children of alcoholics. *Alcohol*, 4:301–305.

Polich, J., and Burns, T. (1987). P300 from identical twins. *Neuropsychologia*, 25:299–304.

Polich, J., et al. (1983). P300 latency correlates with digit span, *Psychophysiology*, 20:665–669.

Polich, J., et al. (1988). P300 and the risk for alcoholism: family history, task difficulty and gender. *Alcohol Clin. Exp. Res.*, 12:248–254.

Polich, J., et al. (1994). Meta-analysis of P300 amplitude from individuals at risk for alcoholism. *Psychol. Bull.*, (In press).

Pollock, V. E., et al. (1983). EEG identification of subgroups of mean at risk for alcoholism. *Arch. Gen. Psychiatry*, 40(8):857–61.

Posner, M. I., et al. (1988). Asymmetrics in hemispheric control of attention in schizophrenia. *Arch. Gen. Psych.*, 45:814–821.

Post, R. M., et al. (1989). Anticonvulsants as adjuncts to neuroleptics in the treatment of schizoaffective and schizophrenic patients. Clin Use of Anticonvulsants in Psychiatric Disorders. *Demos Publications*, 153.

Post, R. M., et al. (1989). Anticonvulsants in the treatment of aggression and dyscontrol. Clin Use of Anticonvulsants in Psychiatric Disorders. *Demos Publications*, 165.

Post, R. M., et al. (1989). Use of anticonvulsants in the treatment of manic-depressive illness. Clin Use of Anticonvulsants in Psychiatric Disorders. *Demos Publications*, 113–153.

Pouloit, M. C., et al. (1990). Apolipoprotein E polymorphism alters the association between body fatness and plasma lipoproteins in women. *J. Lipid Res.*, 31:1023–1029.

Price, R. A., et al. (1990) Common major gene inheritance of extreme overweight. *Hum. Biol.*, 62:747–765.

Prichep, L. S., et al. (1976). Evoked potentials in hyperkinetic and normal children under certainty and uncertainty: A placebo and Methylphenidate study. *J. Electrophysiology*, 13:419–428.

Projesz, B., et al. (1987). N2 component of the event-related brain potential in abstinent alcoholics. *Electroencephalogr. Clin. Neurophysiol.*, 66(2):121–31.

Propping, P., Nöthen, M. M., Fimmers, R., and Baur, M. P. (1993). Linkage versus association studies in complex disorders. *Psychiat. Genet*.3:136 (Abst.).

Rajput-Williams, J., et al. (1988). Variation of apolipoprotein-B gene is associated with obesity, high blood cholesterol levels, and increased risk of coronary heart disorder. *Lancet*, ii:1442–1446.

Rastinejad, F., and Blau, H. M. (1993). Genetic complementation reveals a novel regulatory role for 3' untranslated regions in growth and differentiation. *Cell*, 72:903–917.

Ritter, W., and Vaughan, H. G., Jr. (1969). Averaged evoked responses in vigilance and discrimination: a reassessment. *Science*, 164:326–328.

Rockstroh, B., et al. (1991). Effects of the anticonvulsants benzodiazepine clonazepam on event-related brain potentials in humans. *Electroencephalogr. Clin. Neurophysiol.*, 78(2):142–9.

Rogers, T. D., and Deary, I. (1991). The P300 component of the auditory event-related potential in monozygotic and dizygotic twins. *Acta. Psychiar. Scan.*, 83:412–416.

Rosenthal, R. J. (1992). Pathological gambling, *Psychiatric Ann.*, 22:72–78.

Rosvold, N. E., et al. (1956). A continuous-performance test of brain damage. *J. Consulting Psychology*, 20:343–352.

Roy, A., DeJong, J., Lamparski, D., George, T., and Linnoila, M. (1991). Depression among alcoholics—relationship to clinical and cerebrospinal fluid variables. *Arch. Gen. Psych.*, 48:428–432.

Saiki, R. K., et al. (1988). Primer-directed enzymatic amplification of DNA with a thermostable DNA polymerase. *Science*, 239:487–491.

Sakar, G., and Sommer, S. S. (1991). Haplotyping by double PCR™ amplification of specific alleles. *Biotechniques*, 10:436–440.

Sandkuyl, L. A. (1989). Analysis of affected sib pairs using information from extended families. In Elston RC et al. (Eds.) Multipoint Maping and Linkage based upon affected pedigree members. Alan R. Liss, New York.

SAS Institute, SAS users guide, version 6.07, SAS Institute, NC, SAS technical report P-229, SAS/STAT software: changes and enhancements, Rel. 6.07. Cary, NC.

Scatton, B., et al. (1982). Dopamine deficiency in the cerebral cortex in Parkinson's disorder. *Neurology*, 32:1039–1040.

Schuckit, M. A., Goodwin, D. W., and Winokur, G. (1972). A study of alcoholism in half-siblings. *Amer. J. Psychiat.*, 128:1132–1136.

Schwab, S., Soyka, M., Niederecker, M., Ackenheil, M., Scherer, J., and Wildenauer, D. B. (1991). Allelic association of human $D_2$ receptor DNA polymorphism ruled out in 45 alocholics. *Am J. Hum. Genet.*, 49(Suppl.):203 (Abstract).

Scoville, B. A. (1975). Review of amphetamine-like drugs by the Food and Drug Administration: Clinical data and value judgements. In Bray, G. A., (Ed.). *Obesity in perspective* Government Printing Office, Washington, D.C., pp. 441–443.

Seeman, P., et al. (1987). Human brain dopamine receptors in children and ageing adults. *Synapse*, 1:399–404.

Sheffield, V. C., Cox, D. R., Lerman, L. S., and Myers, R. M. (1989). Attachment of a 40-base-pair G+ C-rich sequence (GC-clamp) to genomic DNA fragments by polymerase chain reaction results in improved detection of single-base changes. *Proc. Natl. Acad. Sci. USA*, 86:232–236.

Shigeta, Y., Ishii, H., Takagi, S., et al. (1980). HLA antigens as immunogenetic markers of alcoholism and alcoholic lever disorder. *Pharmacol. Biochem. Behav.*, 13(suppl 1):89–94.

Siegel, S. (1956). Nonparametric statistics for the behavioral sciences. McGraw Hill Book Co., New York, pp. 104–111.

Simerly, R. B., Swanson, L. W., and Gorski, R. A. (1985). Reversal of the sexually dimorphic distribution of serotonin-immunoreactive fibers in the medial preoptic nucleus by treatment with perinatal androgen. *Brain Res.*, 340:91–98.

Sims, E. A. H. (1990). Destiny rides again as twins overeat. *N. Eng. J. Med.*, 322:15252–1525.

Slater, E. P., Rabenau, O., Karin, M., Baxter, J., and Beato, M. (1985). Glucocorticoid receptor binding and activation of a heterologous promotor by dexamethasone by the first intron of the human growth hormone gene. *Mol. Cell. Biol.*, 5:2984–2992.

Sloan, E. P., et al. (1992). Anticholinergic drug effects on quantitative electroencephalogram, visual evoked potential, and verbal memory. *Biol. Psychiatry*, 31(6):600–6.

Smith, G. P., and Schneider, L. A. (1988). Relationship between mesolimbic dopamine function and eating behavior. *Ann. N. Y. Acad. Sci.*, 537:254–261.

Smith, S. S., et al. (1992). Genetic vulnerability to drug abuse: the $D_2$ dopamine receptor TaqI B1 restriction fragment length polymorphism appears more frequently in polysubstance abusers. *Arch. Gen. Psychiatry*, 49(9):723–7.

Smith, S. S., Gorelick, D. A., O'Hara, B. F., and Uhl, G. R. (1991). The dopamine $D_2$ receptor gene and alcoholism. *JAMA*, 265:2667–2668.

Squire, N. K., et al. (1977). Biosensory stimulation: uninferring decision-related processes from the P300 component. *J. Exp. Psychol. Hum. Percept.*, 3:299–315b.

Squires, K. C., et al. (1977). On the influence of task relevance and stimulus probability on event-related potential components. *Electroencephalogr. Clin. Neurophysiol.*, 42:1–14a.

Stanzione, P., et al. (1990). Dopaminergic pharmacolgyical manipulations in normal humans confirm the specificity of the visual (PERG-VEP) and cognitive (P300 ) electrophysiological alterations in Parkinson's disorder. *Electroencephalogr. Clin. Neurophysiol.*, 44:447–478.

Stanzione, P., et al. (1991). P300 variations in Parkinsonian patients before and during dopaminergic monotheraphy: a suggested dopamine component in P300. *Electroencephalgr. Clin. Neurphysiol.*, 80:446–453.

Stoudemire, A., et al. (1983). Interictal schizophrenia-like psychoses in temporal lobe epilepsy (Review). *Psychosomatics*, 24(4):331–3, 337–9.

Struve, F., and Straumanis, J. J. (1989). Persistent topographic quantitative EEG changes in chronic marihuana (THC) use: a replication study. *Biol. Psychiatry*, 25:29A.

Struve, F., and Straumanis, J. J. (1990). Separation of chronic marijuana (THC) users from nonusers: a discriminant function analysis using quantitative electroencephalographic variables. *Biol. Psychiatry*, 27:52A–53A.

Struve, F. A., and Straumanis, J. J. (1990). Electroencephalographic and Evoked Potentials Methods in Human Marijuana Research: Historical Review and Future Trends. *Wiley-Liss Inc.*, New York.

Stunkard, A. J. (1988). The Salmon lecture. Some perspectives on human obesity: Its causes. *Bull. N. Y. Acad. Med.*, 64:902–923.

Stunkard, A. J., et al. (1986). An adoption study of human obesity. *N. Eng. J. Med.*, 314:193–198.

Stuppaeck, C. H., et al. (1992). Carbamazepine versus oxazepam in the treatment of alcohol withdrawal: a double-blind study. *Alcohol Alcohol.*, 27(2):153–8.

Suarez, B. K., Parsian, A., Hampe, C. L., Todd, R. D., Reich, T., Cloninger, and C.R. (1994). Linkage disequilibria at the $D_2$ dopamine receptor locus (DRD2 ) in alcoholics and controls. *Genomics*, 19:12–20.

Surwillo, W. W. (1980). Corrical evoked potentials in monozygotic twins and unrelated subjects: comparisons of exogeneous and endogenous components. *Behav. Genet.*, 10:201–209.

Sutton, S., et al. (1965). Evoked potential correlates of stimulus uncertainty. *Science*, 150:1187–1188.

Swan, G. E., et al. (1990). Smoking and alcohol consumption in adult male twins: genetic heritability and shared environmental influences. *J. Substance Abuse*, 2:39–50.

Thatcher, R. W., and Fishbein, D. H. (1984). Computerized EEG, nutrition and behavior. *J. Appl. Nutrit.*, 36(2):81–92.

Tollefson, G. D. (1991). Anxiety and Alcoholism—A Serotonin Link. *Br. J. Psychiatry*, 159:34–39.

Treiman, D. M., et al. (1990). A progressive sequence of electroencephalographic changes during generalized convulsive status epilepticus. *Epilepsy Res.*, 5(1):49–60.

Trepicchio, W. L., and Krontiris, T. G. (1982). Members of the rel/NF-kB family of transcriptional regulatory factors bind the HRAS1 minisatellite DNA sequence. *Nucl. Acids Res.*, 21:977–985.

Turner, E., Ewing, J., Shilling, P., Smith, T. L., Irwin, M., Schuckit, M., Kelsoe, J. R. (1992). Lack of association between an RFLP near the $D_2$ dopamine receptor gene and severe alcoholism. *Biol. Psychiatry*, 31:285–290.

Uhl, G., Blum, K., Noble, E., and Smith, S. (1993). Substance abuse vulnerability and $D_2$ receptor genes. *Trends Neurosci.*, 16:83–88.

Uhl, G., Persico, A. L., and Smith, S. S. (1992). Current excitement with $D_2$ receptor gene alleles in substance abuse. *Arch. Gen. Psychiatry*, 49:157–160.

Uhl, G. R. (1994). Molecular and genetic studies of the targets of acute drug action, substrates for inter individual differences in vulnerability to substance abuse, and candidate mechanisms for addiction. In Chiarello, E., (Ed.). *NIDA Monographs*. (In press).

Vasile, R. G., et al. (1992). Abnormal flash visual evoked response in melancholia: a replication study. *Biol. Psychiatry*, 31:325–336.

Virkkunen, M., Linnoila, M. (1991). Serotonin in early onset, male alcoholics with violent behaviour. *Ann. Med.*, 22:327–331.

Warner, R. H., Rossett, H. L. (1975). The effects of drinking on offspring: An historical survey of the American and British literature. *J. Stud. Alcohol*, 36:1395–1420.

Weaver, J. U., et al. (1991a). An association between BclI restriction fragment length polymorphism of the glucocorticoid locus and hyperinsulinemia in obese women. *J. Molec. Endocrin.*, 9:295–300.

Weaver, J. U., et al. (1991b). Central obesity and hyperinsulinemia in women are associated with polymorphisms in the 5' flanking region of the human insulin gene. *Eur. J. Clin. Invest.*, 22:265–270.

Westermeyer, J., et al. (1994). Substance abuse and associated psychiatric disorder among 100 adolescents. *J. Addict. Disorders*, 13(1):67–89.

Whipple, S. C., Parker, E. S., and Noble, E. P. (1988). An atypical neurocognitive profile in alcoholic fathers and their sons. *J. Stud. Alcohol*, 49(3):240–4.

White, J. W., Sobnosky, M., Rogers, B. L., Walker, W. H., and Saunders, G. F. (1989). Nucleotide sequence of a transcriptional enhancer located 2.2 Kb 3' of a human placental lactogen-encoding gene. *Gene*, 84:521–522.

Wills, T. A., et al. (1994). Psychosocial predictors of early-onset substance use. *Ann. Behav. Med.*, 16:B066.

Wise, R. A. (1987). The role of reward pathways in the development of drug dependence. *Pharmacol. Ther.*, 35:227–263.

Wise, R. A., and Rompre, P. P. (1989). Brain dopamine and reward. *Ann. Rev. Psychol.*, 40:191–225.

Wong, D. F., et al. (1984). Effects of age on dopamine and serotonin receptors measured by position emmision tomography in the living human brain. *Science*, 226:1393–1396.

Wurtman, J., et al. (1987). Fenfluramine suppresses snack intake among carbohydrate cravers but not among non-carbohydrate cravers. *Int. J. Eating Disorders*, 6:687–699.

Wurtman, R. J. (1983). Food consumption, neurotransmitter synthesis, and human behavior. *Experientia.*, 44:356–369.

Wurtman, R. J. (1987). Dietary treatments that affect brain neurotransmitters. Effects on calorie and nutrient intake. *Ann. N. Y. Acad. Sci.*, 499:179–190.

Yoshida, A., Huang, I-Y, and Ikawa, M. (1984). Molecular abnormality of an inactive aldehyde dehydrogenase variant commonly found in Orientals. *Proc. Natl. Acad. Sci. USA*, 81:258–261.

Zee, R. Y. L., et al. (1992). Marked association of a RFLP for the low density lipoprotein receptor gene with obesity in essential hypertensives. *Biochem. Biophys. Res. Comm.*, 189:965–971.

Ziedonis, D. M., et al. (1994). Psychiatric comorbidity in white and African-American cocaine addicts seekingsubstance abuse treatment. *Hosp. Comm. Psychiatry*, 45(1):43.

Zonata, L. A., et al. (1987). Genetic analysis of human obesity in an Italian sample. *Hum. Hered.*, 37:129–139.

---

What is claimed is:

1. A method for determining a type of compulsive disorder in an individual comprising:

identifying an individual having at least one compulsive disorder;

obtaining DNA from said individual;

analyzing said DNA for the presence of a human dopamine $D_2$ receptor gene A1, B1 or $DRD2^{In6-Ex7}$ haplotype I allele;

wherein the presence of said human dopamine $D_2$ receptor gene A1, B1 or $DRD2^{In6-Ex7}$ haplotype I allele indicates a compulsive disorder resulting from Reward Deficiency Syndrome or impulsive-addictive-compulsive disorder and the lack of a human dopamine $D_2$ receptor gene A1, B1 or $DRD2^{In6-Ex7}$ haplotype I allele indicates a compulsive disorder having other causes.

2. The method of claim 1, wherein the individual is the child of a parent having at least one compulsive disorder, and the presence of a human dopamine $D_2$ receptor gene A1, B1 or $DRD2^{In6-Ex7}$ haplotype I allele indicates genetic susceptibility to Reward Deficiency Syndrome or impulsive-addictive-compulsive disorder.

3. The method of claim 1, wherein the individual is the child of a parent having at least one compulsive disorder, and the presence of a human dopamine $D_2$ receptor gene A1, B1 or $DRD2^{In6-Ex7}$ haplotype I allele indicates genetic susceptibility to alcoholism, severe alcoholism, drug addiction, polysubstance abuse, cocaine dependency, overeating, or smoking.

4. The method of claim 1, wherein detecting a human dopamine $D_2$ receptor gene A1, B1, or $DRD2^{In6-Ex7}$ haplotype I allele comprises:

subjecting said DNA of said subject to digestion by a restriction enzyme;

hybridizing said DNA to a labeled probe specifically binding the A1 allele of the human dopamine $D_2$ receptor, the B1 allele of the human dopamine D2 receptor, or the $DRD2^{In6-Ex7}$ haplotype I allele of the human dopamine D2 receptor;

determining the presence of said A1, B1, or $DRD2^{In6-Ex7}$ haplotype I alleles of the human dopamine $D_2$ receptor.

5. The method of claim 1, wherein the compulsive disorder of the parent is Reward Deficiency Syndrome or impulsive-addictive-compulsive disorder.

6. The method of claim 1 wherein the compulsive disorder of the parent is alcoholism, severe alcoholism, drug addiction, polysubstance abuse, cocaine dependency, overeating, or smoking.

7. A method of detecting a genetic potential susceptibility to a compulsive disorder in a human subject, comprising:

obtaining DNA from a subject; and detecting, in said DNA, a human dopamine $D_2$ receptor gene A1, B1, or $DRD2^{In6-Ex7}$ haplotype I allele, wherein said A1, B1, or $DRD2^{In6-Ex7}$ Haplotype I allele indicates a potential susceptibility to a compulsive disorder.

8. The method of claim 7, wherein detecting a human dopamine $D_2$ receptor gene A1 allele comprises:

subjecting said DNA of said subject to digestion by a restriction enzyme;

hybridizing said DNA to a labeled probe specifically binding the 6.6 kb A1 allele of the human dopamine $D_2$ receptor;

determining the presence of said A1 allele of the human dopamine $D_2$ receptor.

9. The method of claim 7, wherein detecting a human dopamine $D_2$ receptor gene B1 allele comprises:

subjecting said DNA of said subject to digestion by a restriction enzyme;

hybridizing said DNA to a labeled probe specifically binding the 4.6 kb B1 allele of the human dopamine $D_2$ receptor;

determining the presence of said B1 allele of the human dopamine $D_2$ receptor.

10. The method of claim 7, wherein said probe is a recombinant phage $\lambda$-$hD_2$G1 or a fragment thereof.

11. The method of claim 7, recombinant phage $\lambda$-$hD_2$G2 or a fragment thereof.

12. The method of claim 8 or 9, wherein the DNA is separated by electrophoresis according to size.

13. The method of claim 7, wherein the compulsive disorder is Reward Deficiency Syndrome, impulsive-addictive-compulsive disorder, or overeating.

14. The method of claim 7 wherein the compulsive disorder is tobacco abuse, cigarette smoking, or addiction to nicotine.

15. The method of claim 7, wherein the compulsive disorder is polysubstance abuse, drug addiction, or cocaine dependence.

16. The method of claim 7 wherein the compulsive disorder is alcoholism, severe alcoholism, or a DRD2$^{In6-Ex7}$ haplotype I subtype of alcoholism.

17. The method of claim 7 wherein the detecting involves RFLP or PASA.

18. The method of claim 7 wherein the compulsive disorder is Reward Deficiency Syndrome and the human dopamine D2 receptor gene allele is an A1 or B1 allele.

19. The method of claim 7 wherein the compulsive disorder is compulsive overeating or obesity and the human dopamine $D_2$ receptor gene allele is an A1 or B1 allele.

20. The method of claim 7 wherein the compulsive disorder is tobacco abuse, nicotine addiction, or cigarette smoking and the human dopamine $D_2$ receptor gene allele is an A1 or B1 allele.

21. The method of claim 7 wherein the compulsive disorder is polysubstance abuse, cocaine dependency, or drug addiction and the human dopamine D2 receptor gene allele is an A1 or B1 allele.

22. The method of claim 7 wherein the compulsive disorder is alcoholism, severe alcoholism, or a DRD$_2$$^{In6-Ex7}$ Haplotype I subtype of alcoholism, and the human dopamine D2 receptor gene allele is an A1, B1, or a DRD$_2$$^{In6-Ex7}$ Haplotype I subtype allele.

23. The method of claim 7, wherein the compulsive disorder is compulsive overeating, carbohydrate bingeing overeating, the allele is an A1 or B1 allele, and detecting said human dopamine $D_2$ receptor gene A1 or B1 allele comprises:

subjecting the DNA to digestion by TaqI restriction enzyme;

hybridizing said DNA to a labeled probe specifically binding a 6.6 kb A1 allele, or a 4.6 kb B1 allele of the human dopamine $D_2$ receptor.

24. The method of claim 7, wherein the compulsive disorder is tobacco abuse, smoking, or nicotine addiction, the allele is an A1 or B1 allele, and detecting said human dopamine $D_2$ receptor gene A1 or B1 allele comprises:

subjecting the DNA to digestion by TaqI restriction enzyme;

hybridizing said DNA to a labeled probe specifically binding a 6.6 kb A1 allele, or a 4.6 kb B1 allele of the human dopamine $D_2$ receptor.

25. The method of claim 7, wherein the compulsive disorder is compulsive overeating, or carbohydrate bingeing, the allele is an A1 or B1 allele, and detecting said human dopamine $D_2$ receptor gene A1 or B1 allele comprises:

subjecting the DNA to digestion by TaqI restriction enzyme;

hybridizing said DNA to a labeled probe specifically binding a 6.6 kb A1 allele, or a 4.6 kb B1 allele of the human dopamine $D_2$ receptor.

26. A method of detecting a genetic potential susceptibility to compulsive disorder in a human subject, comprising:

obtaining DNA from said subject;

subjecting said DNA of said subject to digestion by a restriction enzyme;

hybridizing said DNA to a labeled probe specifically binding the 6.6 kb A1 allele, or the 4.6 kb B1 allele of the human dopamine $D_2$ receptor;

determining the presence of either said A1 or B1 allele of the human dopamine $D_2$ receptor.

27. A kit for use in genetically detecting potential susceptibility to compulsive disorder in a human subject, said kit comprising:

(a) a carrier compartmentalized to receive one or more container means in close confinement therein;

(b) a first container means including a restriction enzyme capable of cleaving a human dopamine $D_2$ receptor gene; and (c) a second container means including a hybridization probe for detecting a human dopamine $D_2$ receptor gene allele whose presence indicates susceptibility to compulsive disorder.

28. The kit of claim 27, wherein the restriction enzyme is TaqI, the allele is the DRD$_2$ A1 allele, and the hybridization probe specifically binds to the A1 allele.

29. The kit of claim 27, wherein the restriction enzyme is TaqI, the allele is the DRD2 B1 allele, and the hybridization probe specifically binds to the B1 allele.

30. A kit for use in genetically detecting potential susceptibility to compulsive disorder in a human subject, said kit comprising:

a carrier compartmentalized to receive one or more container means in close confinement therein; and a first container means comprising PASA primers specifically binding dopamine $D_2$ receptor alleles characterizing susceptibility to a compulsive disorder; and a second container means comprising ingredients for PCR™ amplification of specific dopamine $D_2$ receptor gene alleles.

31. The kit of claim 30, wherein the primers are #3208 primer with the sequence GAGTCTTCAGAGGGT (SEQ ID NO:3) and #3420 primer with the sequence TGCTGTGGAGACCG (SEQ ID NO:4).

32. A method of detecting a genetic potential susceptibility to compulsive disorder in a human subject, comprising:

obtaining DNA from a human subject; subjecting said DNA of said subject to digestion by a restriction enzyme;

hybridizing said DNA to a labeled probe specifically binding the 4.6 kb B1 allele of the human dopamine $D_2$ receptor or the 6.6 kb A1 allele of the human dopamine $D_2$ receptor;

detecting in the DNA, A1 or B1 alleles.

33. The method of claim 32 wherein the probe is a fragment of recombinant phage λ-hD$_2$G1 or a fragment of recombinant phage λ-hD$_2$G2.

34. The method of claim 5, 9, 10, 13, or 32, wherein the restriction enzyme is TaqI.

* * * * *

UNITED STATES PATENT AND TRADEMARK OFFICE
CERTIFICATE OF CORRECTION

PATENT NO. : 5,550,021
DATED : August 27, 1996
INVENTOR(S) : Kenneth Blum, San Antonio, Tex.; Ernest P. Noble, Los Angeles, Calif.; Peter J. Sheridan, San Antonio, Tex.

It is certified that error appears in the above-indentified patent and that said Letters Patent is hereby corrected as shown below:

In claim 10, column 88, line 59, replace "7" with --8 or 9--.

In claim 11, column 88, line 61, replace "7" with --8 or 9--, wherein said probe is a--.

In claim 34, column 90, line 60, "claim 5, 9, 10, 13, or 32," should read --claim 4, 8, 9, 26, or 32,--.

Signed and Sealed this

Twenty-sixth Day of November 1996

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
CCGTCGACCC TTCCTGAGTG TCATCA                    26
```

( 2 ) INFORMATION FOR SEQ ID NO: 2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
CCGTCGACGG CTGGCCAAGT TGTCTA                    26
```

( 2 ) INFORMATION FOR SEQ ID NO: 3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

GAGTCTTCAC AGGGT                         15

( 2 ) INFORMATION FOR SEQ ID NO: 4:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

TGCTGTGGAG ACCG                          14